(12) United States Patent
Cao et al.

(10) Patent No.: US 11,591,287 B2
(45) Date of Patent: Feb. 28, 2023

(54) ANTIFOULING ZWITTERIONIC POLYMER COATING AND REVERSE COATING METHOD

(71) Applicant: Wayne State University, Detroit, MI (US)

(72) Inventors: Zhiqiang Cao, Troy, MI (US); Wei Wang, Detroit, MI (US)

(73) Assignee: Wayne State University, Detroit, MI (US)

( * ) Notice: Subject to any disclaimer, the term of this patent is extended or adjusted under 35 U.S.C. 154(b) by 542 days.

(21) Appl. No.: 16/619,699

(22) PCT Filed: Jun. 6, 2018

(86) PCT No.: PCT/US2018/036291
§ 371 (c)(1),
(2) Date: Dec. 5, 2019

(87) PCT Pub. No.: WO2018/226854
PCT Pub. Date: Dec. 13, 2018

(65) Prior Publication Data
US 2020/0181426 A1    Jun. 11, 2020

Related U.S. Application Data

(60) Provisional application No. 62/623,844, filed on Jan. 30, 2018, provisional application No. 62/573,431,
(Continued)

(51) Int. Cl.
*C07C 229/22*    (2006.01)
*A61K 31/337*    (2006.01)
(Continued)

(52) U.S. Cl.
CPC .......... *C07C 229/22* (2013.01); *A61K 31/337* (2013.01); *A61K 35/76* (2013.01);
(Continued)

(58) Field of Classification Search
None
See application file for complete search history.

(56) References Cited

U.S. PATENT DOCUMENTS 5,562,646 A    10/1996    Goldman et al.
5,858,746 A    1/1999    Hubbell et al.
(Continued)

FOREIGN PATENT DOCUMENTS

CN    102697755 A    10/2012
CN    105209562 A    12/2015
(Continued)

OTHER PUBLICATIONS

Nurkeev A, Z. et al., Synthesis of Cationic Water-Soluble Copolymers and Hydrogels Based on [2-Methacryloyloxy) ethyl]trimethyammonium Chloride arid 2-Hydroxyethylacrylate and Their Complex Formation with Poly(acrylic acid) Journal of Polymer Science: Part B: Polymer Physics, 44: 845-853, 2006.
(Continued)

*Primary Examiner* — Ramsey Zacharia
(74) *Attorney, Agent, or Firm* — Juhe K. Staple; Dinsmore & Shohl LLP

(57) ABSTRACT

Compositions are provided according to aspects of the present invention that include a hydrogel and a liner, wherein a surface of the hydrogel dissociably-engages a surface of the liner. Compositions are provided according to aspects of the present invention that include a hydrogel and a hydrophobic glue, wherein at least a portion of the gel network of the hydrogel is occupied by the hydrophobic glue. Reverse coating processes and articles of manufacture made by reverse coating processes are provided according to aspects of the present invention. Compositions are provided according to aspects of the present invention that include a hydrogel and a substrate, wherein: the hydrogel comprises a polymer network; the substrate comprises a surface com-
(Continued)

prising a polymer network; and the polymer network of the hydrogel and the polymer network of the surface are entangled.

13 Claims, 30 Drawing Sheets

Related U.S. Application Data filed on Oct. 17, 2017, provisional application No. 62/515,704, filed on Jun. 6, 2017.

(51) Int. Cl.
| | |
|---|---|
| A61K 35/76 | (2015.01) |
| A61K 38/28 | (2006.01) |
| A61K 39/00 | (2006.01) |
| A61K 39/39 | (2006.01) |
| A61K 47/54 | (2017.01) |
| A61K 47/58 | (2017.01) |
| A61K 47/69 | (2017.01) |
| B32B 7/12 | (2006.01) |
| B32B 27/08 | (2006.01) |
| C07C 227/16 | (2006.01) |
| C08F 120/36 | (2006.01) |
| C08G 81/02 | (2006.01) |
| C09D 5/16 | (2006.01) |
| C09D 133/14 | (2006.01) |
| C09D 133/26 | (2006.01) |
| C12N 15/86 | (2006.01) |
| A61L 27/34 | (2006.01) |
| A61L 27/52 | (2006.01) |
| A61L 29/08 | (2006.01) |
| A61L 31/10 | (2006.01) |
| A61L 31/14 | (2006.01) |
| C08F 220/36 | (2006.01) |
| C08L 33/04 | (2006.01) |

(52) U.S. Cl.
CPC ...... *A61K 38/28* (2013.01); *A61K 39/001106* (2018.08); *A61K 39/39* (2013.01); *A61K 47/543* (2017.08); *A61K 47/544* (2017.08); *A61K 47/58* (2017.08); *A61K 47/6909* (2017.08); *A61K 47/6915* (2017.08); *A61K 47/6921* (2017.08); *B32B 7/12* (2013.01); *B32B 27/08* (2013.01); *C07C 227/16* (2013.01); *C08F 120/36* (2013.01); *C08G 81/027* (2013.01); *C09D 5/1668* (2013.01); *C09D 5/1693* (2013.01); *C09D 133/14* (2013.01); *C09D 133/26* (2013.01); *B32B 2307/7145* (2013.01); *C12N 15/86* (2013.01)

(56) References Cited

U.S. PATENT DOCUMENTS

| | | | |
|---|---|---|---|
| 7,144,992 | B2 | 12/2006 | Madhyastha |
| 2006/0153775 | A1 | 7/2006 | Von Wronski et al. |
| 2011/0097277 | A1 | 4/2011 | Jiang et al. |
| 2011/0160392 | A1 | 6/2011 | Chang et al. |
| 2012/0183602 | A1 | 7/2012 | Chen et al. |
| 2012/0322939 | A1 | 12/2012 | Jiang et al. |
| 2013/0011363 | A1 | 1/2013 | Jiang et al. |
| 2013/0131214 | A1 | 5/2013 | Scales et al. |
| 2014/0271843 | A1 | 9/2014 | Ma et al. |
| 2016/0251470 | A1 | 9/2016 | Cheng et al. |
| 2017/0231940 | A1 | 8/2017 | Shah et al. |

FOREIGN PATENT DOCUMENTS

| | | |
|---|---|---|
| CN | 107519496 A | 12/2017 |
| EP | 0162764 A1 | 11/1985 |
| GB | 2071091 A | 9/1981 |
| JP | 2017028791 A | 2/2017 |
| KR | 1020150107156 A | 9/2015 |
| WO | 2000/61543 A2 | 10/2000 |
| WO | 2011/057225 A2 | 5/2011 |
| WO | 2012/024233 A2 | 2/2012 |
| WO | WO-2013/119183 A1 | 8/2013 |

OTHER PUBLICATIONS

Kou, L. et al., Dual targeting of L-carnitine-conjugated nanoparticles to OCTN2 and ATB0,+ to deliver chemotherapeutic agents for colon cancer therapy, Drug Delivery, 24(1):1338-1349, 2017.

Wang, W. et al., Superdurable Coating Fabricated from a Double-Sided Tape with Long Term "Zero" Bacterial Adhesion, Adv. Mater. 29: 1606506, 2017.

Zhang, L. et al., Zwitterionic hydrogels implanted in mice resist the foreign body reaction, Nature Biotechnology, 31(6): 553-556, May 12, 2013.

Chien, H. et al., Direct cell encapsulation in biodearable and functionalizable carboxybetaine hydrogels, Biomaterials, 33(23): 5706-5712, Apr. 11, 2012.

Lin, C. et al., Peptide-Modified Zwitterionic Porous Hydrogels for Endothelial Cell and Vascular Engineering, Bio Research Open Access, 3(6): 297-310, Dec. 2014.

Wang, L. et al., Development of a Protein Mimic with Peptide Ligands to Enhance Specific Sensing and Targeting by the Zwitterionic Surface Engineering of Poly(amido amine) Dendrimers, Advanced Materials Interfaces, 1(1): 1300059, Feb. 1, 2014.

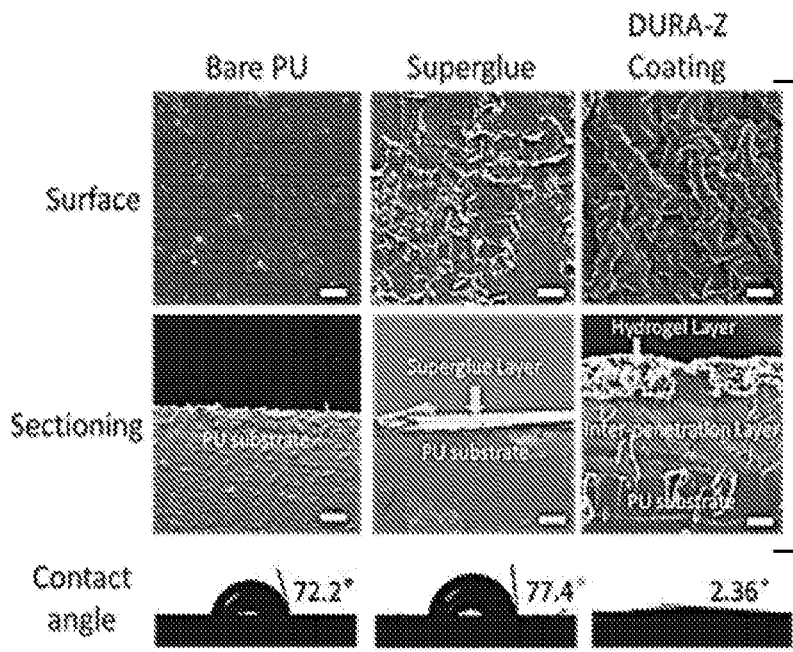
FIG. 2A
FIG. 2B
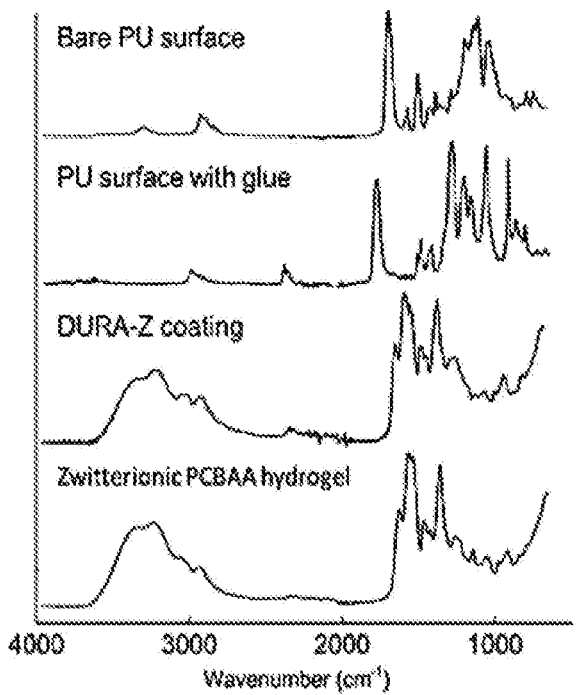
FIG. 2C

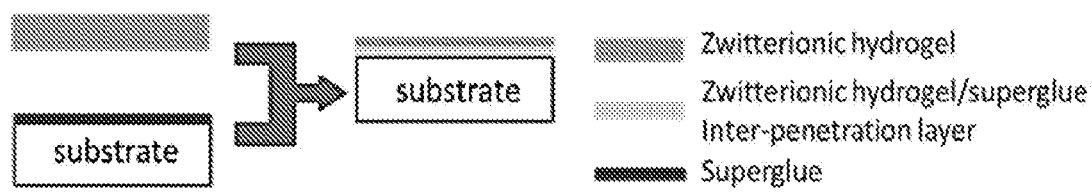
FIG. 2D
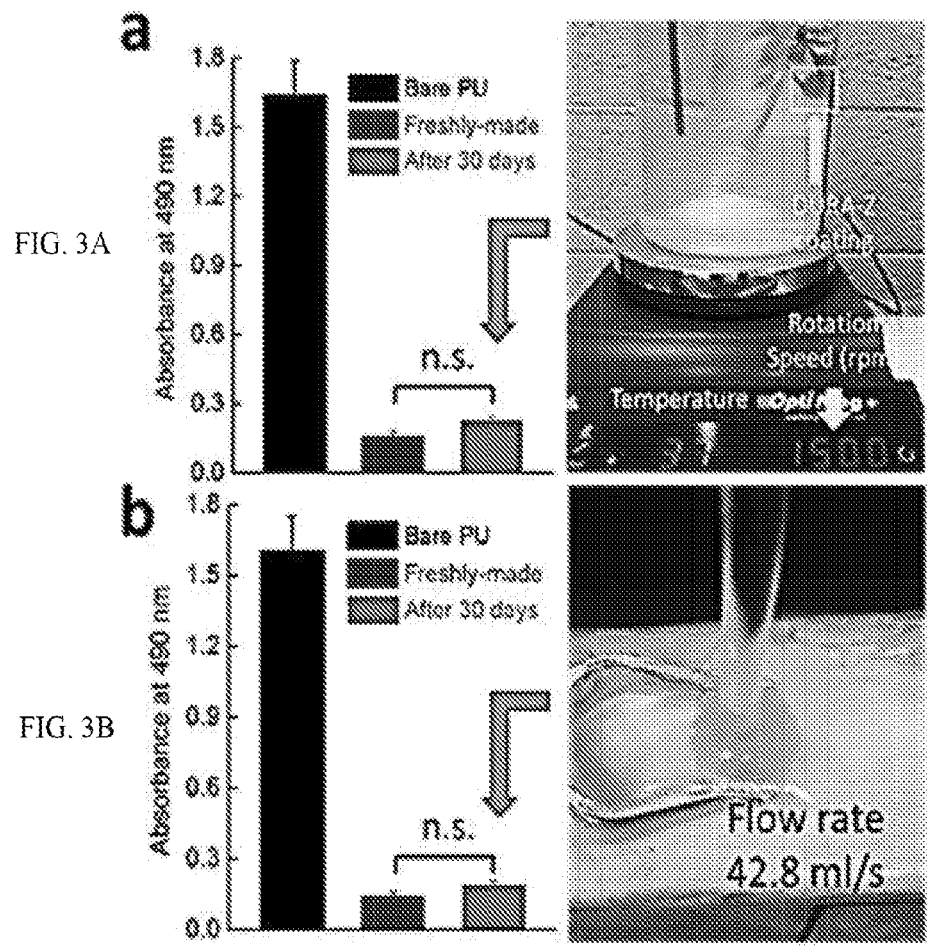
FIG. 3A
FIG. 3B

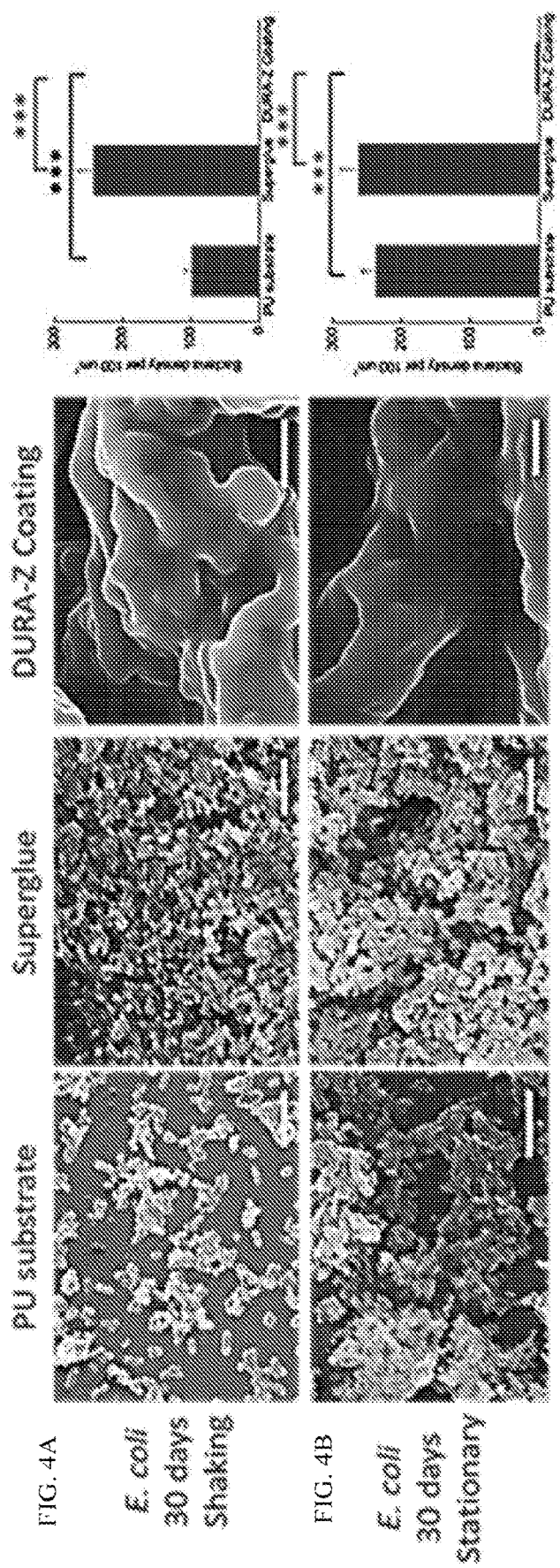
FIG. 4A  E. coli 30 days Shaking
FIG. 4B  E. coli 30 days Stationary

*S. aureus*
30 days
Shaking

*S. aureus*
30 days
Stationary

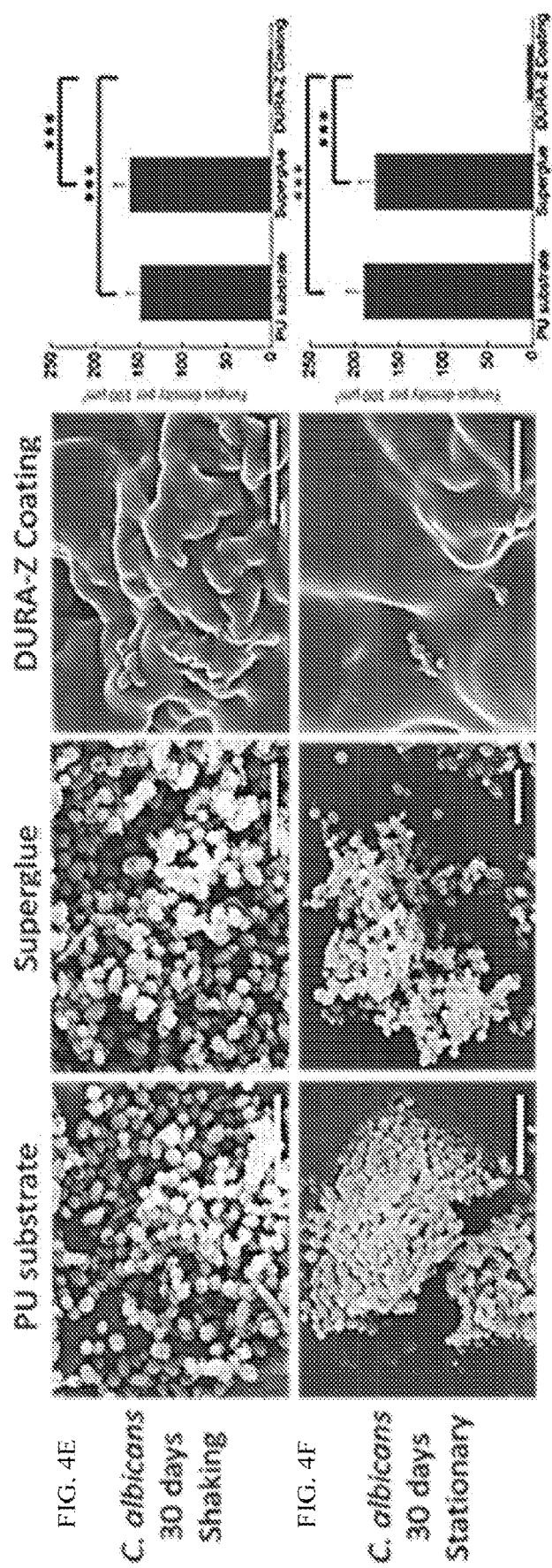
FIG. 4E C. albicans 30 days Shaking
FIG. 4F C. albicans 30 days Stationary

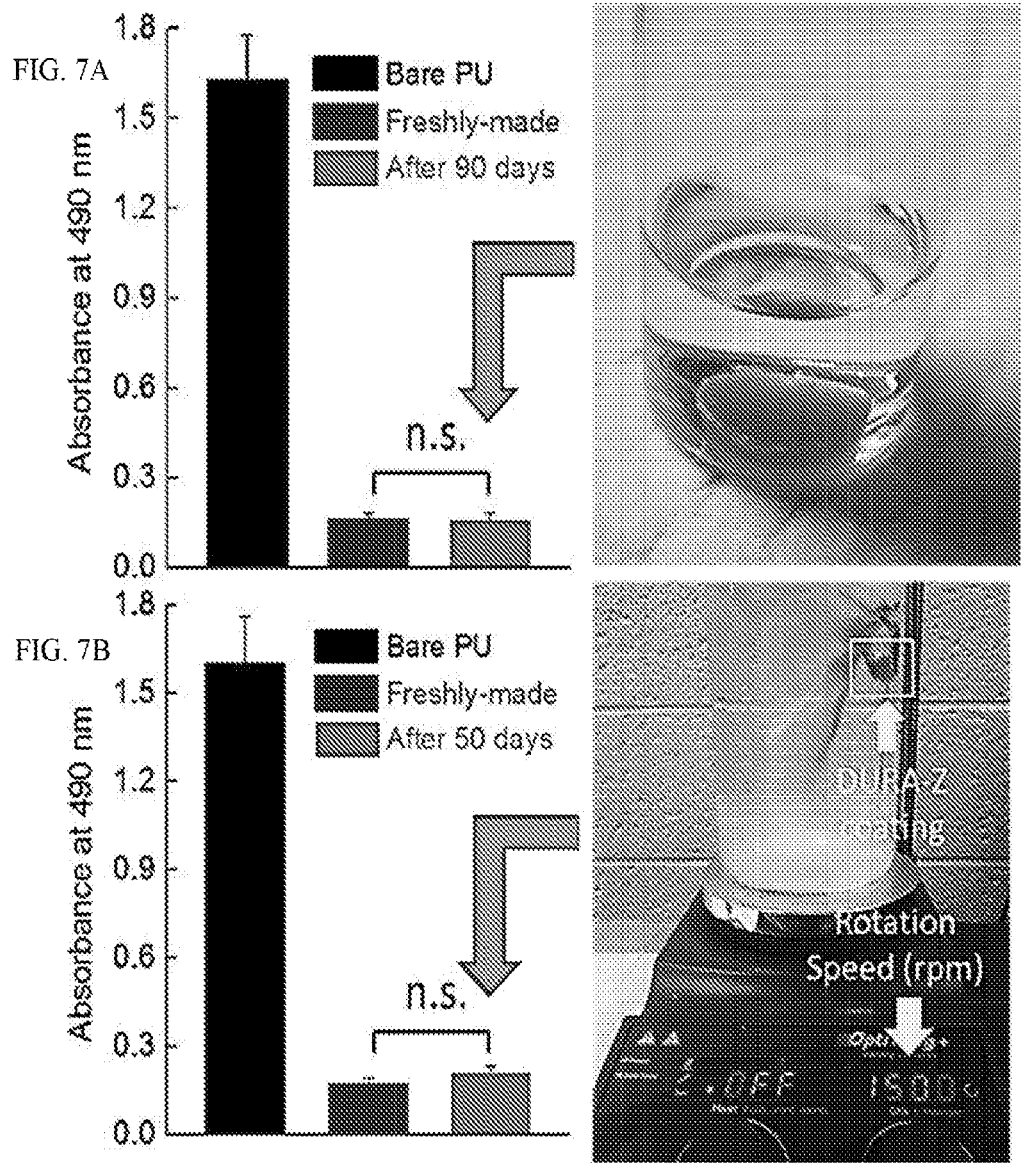

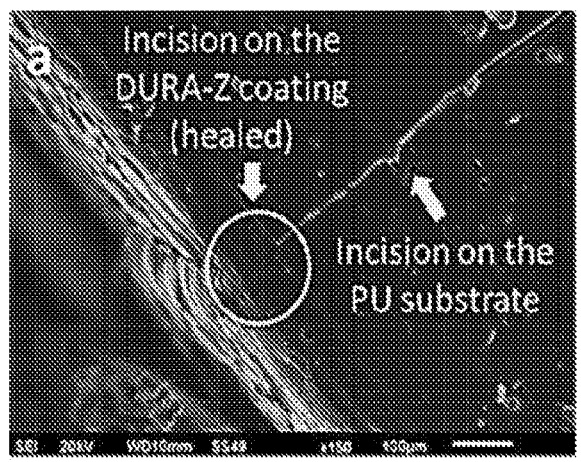
FIG. 9A
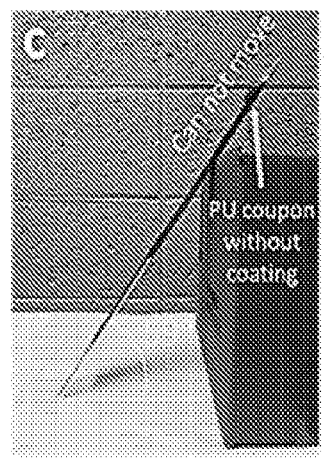
FIG. 9C
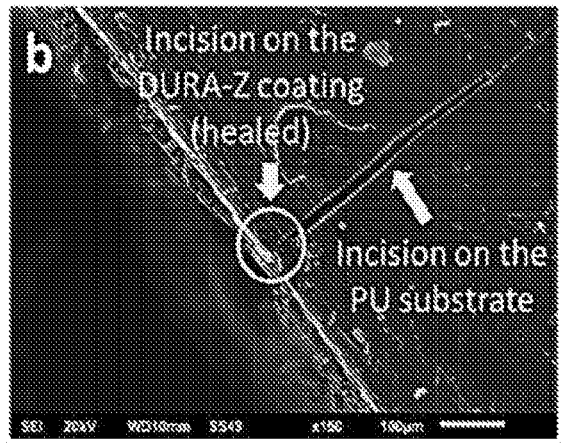
FIG. 9B
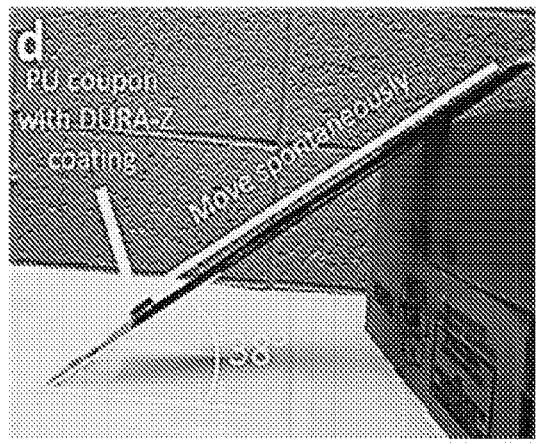
FIG. 9D

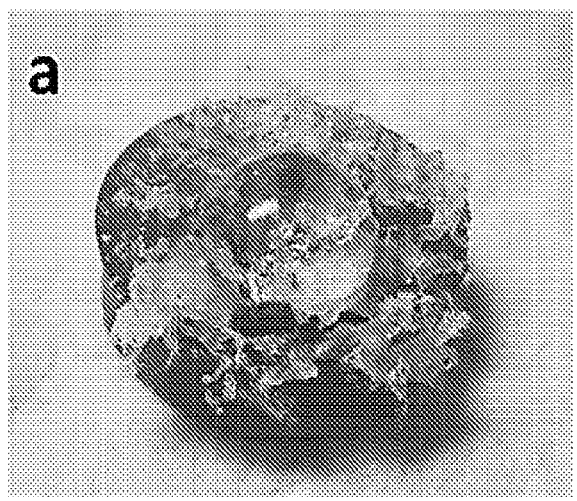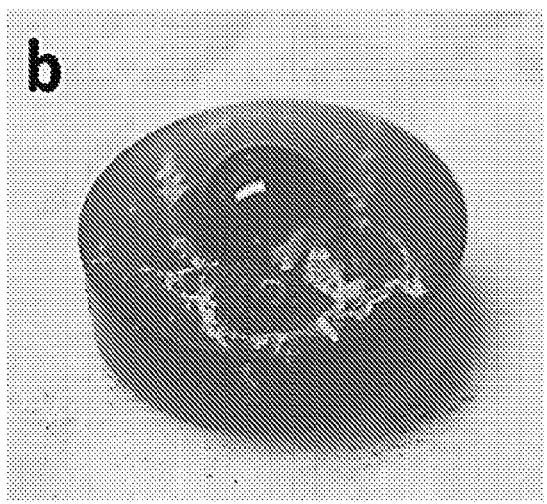
FIG. 16A  FIG. 16B
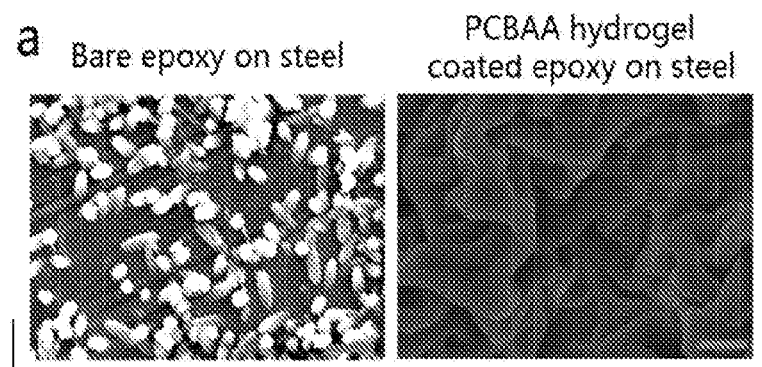
FIG. 17A
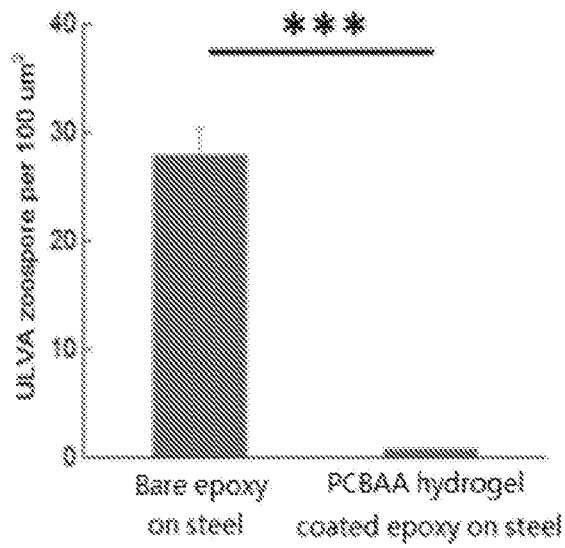
FIG. 17B

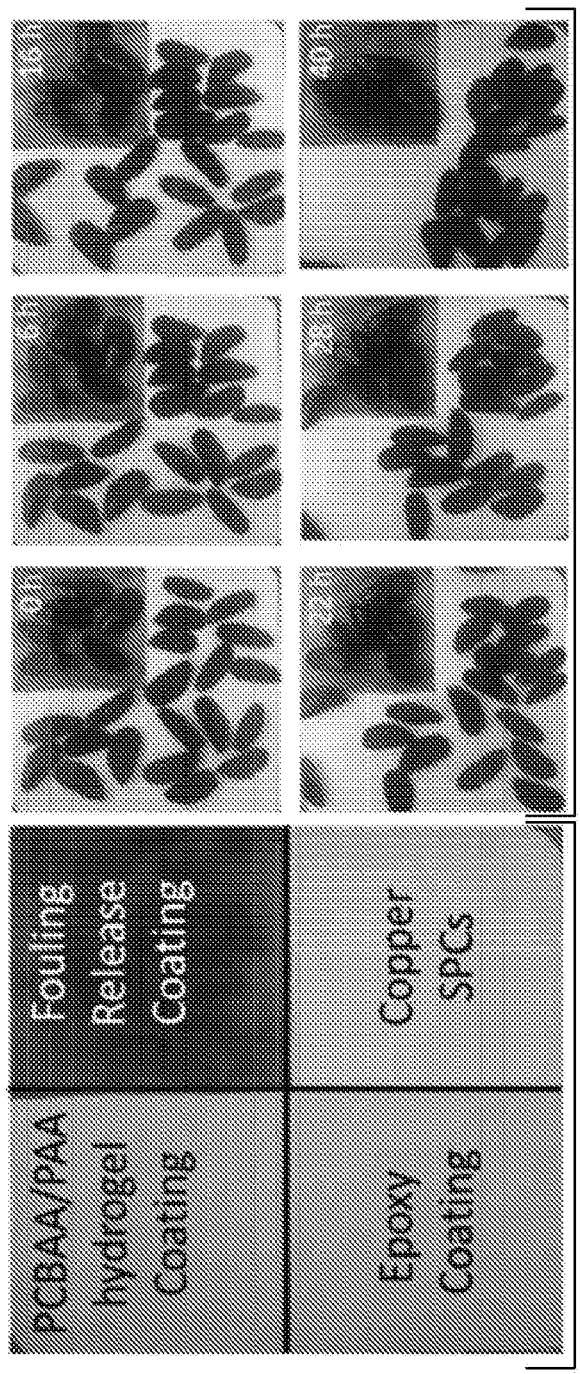
FIG. 20A
FIG. 20B
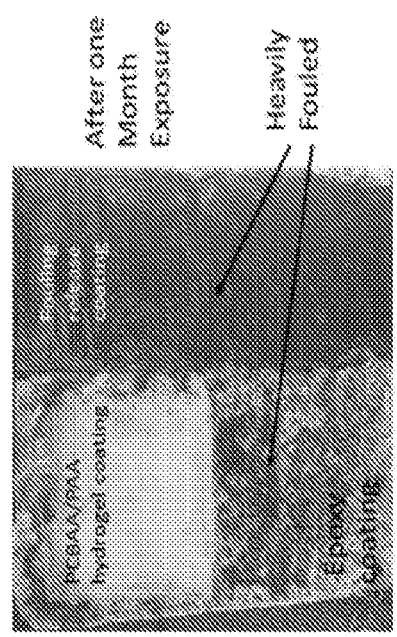
FIG. 20C

ANTIFOULING ZWITTERIONIC POLYMER COATING AND REVERSE COATING METHOD

REFERENCE TO RELATED APPLICATIONS

This application claims priority from U.S. Provisional Patent Application Ser. Nos. 62/515,704, filed Jun. 6, 2017; 62/573,431, filed Oct. 17, 2017; and 62/623,844, filed Jan. 30, 2018. The entire content of each application is incorporated herein by reference.

GOVERNMENT SPONSORSHIP

This invention was made with government support under Grant No. DMR-1410853 awarded by the National Science Foundation. The government has certain rights in the invention.

FIELD OF THE INVENTION

General aspects of the present invention relate to materials for protecting surfaces from fouling and other types of physical, chemical, and biological deterioration. According to specific aspects, hydrogel containing materials are provided for protecting surfaces from fouling and other types of degradation.

BACKGROUND OF THE INVENTION

Compositions and methods that improve the useful lifetime of surfaces and decrease the need for cleaning and maintenance of such surfaces continue to be desirable. Compositions and methods according to aspects of the present invention relate to materials including a hydrogel that can be used to protect surfaces from fouling and other types of physical, chemical, and biological deterioration.

SUMMARY OF THE INVENTION

Compositions are provided according to aspects of the present invention that include a hydrogel and a liner, wherein a surface of the hydrogel dissociably-engages a surface of the liner.

Compositions are provided according to aspects of the present invention that include a hydrogel and a hydrophobic glue, wherein at least a portion of the gel network of the hydrogel is occupied by the hydrophobic glue. For example, a polymer network of the hydrogel can be entangled with a polymer network of a hydrophobic glue.

Compositions are provided according to aspects of the present invention that include a hydrogel and a substrate, wherein: the hydrogel comprises a polymer network; the substrate comprises a surface comprising a polymer network; and the polymer network of the hydrogel and the polymer network of the surface are entangled.

Various aspects of the invention relate to medical devices and water-immersible devices that include any of the compositions described herein.

Methods for applying a hydrophilic polymer hydrogel to a surface are provided according to aspects of the present invention that include contacting the surface with a hydrophobic glue and contacting the hydrophobic glue with a hydrogel. The surface may be contacted with the hydrophobic glue before or after the hydrophobic glue is contacted with the hydrogel, or the two steps may be performed at about the same time.

Methods for making a hydrogel-coated material are provided according to aspects of the present invention that include reverse coating of a substrate.

Methods for making a hydrogel-coated material are provided according to aspects of the present invention that include a reverse coating method including: fixing a hydrogel in a desired shape; contacting the hydrogel with a flowable substrate; and curing or solidifying the substrate. Contacting the hydrogel with the flowable substrate, for example, can result in at least a portion of the flowable substrate entering the hydrogel.

According to aspects of the present invention, methods for applying a hydrophilic polymer hydrogel to a surface and reverse coating methods are performed without modification of the chemical structure of the hydrogel and/or surface to which the hydrogel is applied as a coating. For example, physical entanglement does not change the chemical structure of the hydrogel and/or surface to which the hydrogel is applied as a coating Hydrogels according to various aspects of the invention are zwitterionic hydrogels, such as zwitterionic polymer hydrogels.

Hydrogels according to various aspects of the invention include one or more of: crosslinked poly-acrylic acid, crosslinked poly(vinyl alcohol), non-crosslinked poly(vinyl alcohol), crosslinked poly(vinylpyrrolidone), non-crosslinked poly(vinylpyrrolidone), silicone-containing hydrogel, crosslinked polyacrylamide, crosslinked poly-(N-isopropyl-acrylamide), non-crosslinked poly-(N-isopropyl-acrylamide), crosslinked poly-methyl-methacrylate, poly-hydroxyethyl-methacrylate (PHEMA), crosslinked polyethylene glycol (PEG), crosslinked poly(ethylene glycol) methacrylate (PEGMA), crosslinked poly(ethylene glycol) diacrylate (PEGDA), polypropylene glycol, crosslinked zwitterionic poly-(sulfobetaine methacrylate) (PSBMA), crosslinked zwitterionic 2-methacryloyloxyethyl phosphorylcholine (PMPC), crosslinked zwitterionic poly-carboxybetaine methacrylate (PCBMA), crosslinked zwitterionic poly-carboxybetaine acrylamide (PCBAA), non-crosslinked zwitterionic PCBAA, crosslinked alginate, crosslinked chitosan, gelatin, collagen, fibrin, agarose, hyaluronic acid, cellulose, polypeptides, or a derivative of one or more of the foregoing.

BRIEF DESCRIPTION OF THE DRAWINGS

FIG. 2A shows SEM imaging on the surface and sectioning of uncoated PU, superglue and zwitterionic PCBAA hydrogel (called DURA-Z coating in FIG. 2A) coated substrates (binding composition 1) (scale bar=100 μm), FIG. 2B shows water contact angles on bare PU, superglue and zwitterionic PCBAA hydrogel coated substrates (binding composition 1), FIG. 2C shows IR spectra of bare PU surface, superglue coated PU surface, zwitterionic PCBAA hydrogel (called DURA-Z coating in FIG. 2C) coated surface (binding composition 1) and zwitterionic PCBAA hydrogel surface, and FIG. 2D schematically illustrates of the formation of a binding composition.

FIGS. 3A, 3B, 3C, and 3D show antifouling properties of the zwitterionic PCBAA coating in binding composition 1 (called DURA-Z coating in FIG. 3A) after various durability and mechanical damage tests. FIG. 3A shows results after 30 days exposure to PBS shearing under body temperature, FIG. 3B shows results after 30 days exposure to perpendicular water flush, FIG. 3C shows results after 20 cycles of abrasion test under 570 kPa, and FIG. 3D shows results after random scratch by a scalpel. The antifouling property was evaluated by the resistance of human fibrinogen binding on the surface (absorbed protein) before and after the coating being challenged. All data are presented as mean of replicates (n=3)±standard deviation. Statistical analysis: unpaired, two-tailed t-test, n.s.; no significant difference at P>0.05, meaning the great anti-fouling property was retained.

FIGS. 4A, 4B, 4C, 4D, 4E, and 4F show representative SEM images of bacteria and fungi adhesion on bare PU, superglue and zwitterionic PCBAA hydrogel coated PU substrates (binding composition 1, called DURA-Z coating in FIGS. 4A, 4B, 4C, 4D, 4E, and 4F) after 30 days of co-culture with concentrated microbes and calculated microbe adhesion density for FIG. 4A showing results after shaking condition with *E. coli*, FIG. 4B showing results after stationary condition with *E. coli*, FIG. 4C showing shaking condition with *S. aureus*, FIG. 4D showing results after stationary condition with *S. aureus*, FIG. 4E showing results after shaking conditions with *C. ablicans* and FIG. 4F showing results after stationary condition with *C. ablicans*. All data are presented as mean of biological replicates (n=6)±standard deviation. Statistical analysis: one-way ANOVA with Bonferroni multi-comparison. *; p<0.0001. Scale bar=10 μm

FIGS. 7A and 7B show antifouling property of zwitterionic PCBAA hydrogel coating in binding composition 1 after durability tests. FIG. 7A shows results after 3-month incubation in water and FIG. 7B shows results after 50 days exposure to PBS shearing at room temperature (where binding composition 1 is called DURA-Z coating in FIG. 7B). Data are presented as mean of replicates (n=3)±standard deviation. Statistical analysis: unpaired, two-tailed t-test, n.s.: no significant difference at P>0.05, meaning the great anti-fouling property was retained.

FIGS. 9A and 9B show that zwitterionic PCBAA hydrogel coating (called DURA-Z coating in FIGS. 9A and 9B) in binding composition 1 was able to heal in water after knife scratch. FIGS. 9C and 9D show that zwitterionic PCBAA hydrogel coating (called DURA-Z coating in FIG. 9D) on PU substrate (binding composition 1) was able to decrease more than 53% in friction index against sand paper (without coating: f=tan (59°)=1.664; with zwitterionic PCBAA hydrogel coating, f=tan (38°)=0.781)

FIG. 16A shows PCBAA polymer powder glued on a PU substrate and FIG. 16B shows PCBAA water solution glued on a PU substrate. The coated surface showed hydrophobic nature after incubation in water, as indicated by the non-spread water droplet.

FIG. 17A shows representative SEM images of ULVA zoospore adhesion on epoxy coated steel and PCBAA hydrogel coated epoxy on steel (binding composition 1) after 3 days of co-culture with ULVA zoospore under shaking condition.

FIG. 17B is a graph showing calculated ULVA zoospore density on epoxy on steel and PCBAA hydrogel coated epoxy on steel (binding composition 1). All data are presented as mean of biological replicates (n=6)±standard deviation. Statistical analysis: unpaired two-tailed t-test, ***: p<0.0001. scale bar=5 μm.

FIG. 20A shows coating samples for the mussel preference/walking test.

FIG. 20B shows results of 48 h mussel preference/walking test.

FIG. 20C shows results of a one-month exposure test in Lake St. Clair (PCBAA/PAA coating: free of fouling and mud).

DETAILED DESCRIPTION OF THE INVENTION

Figure 1A:
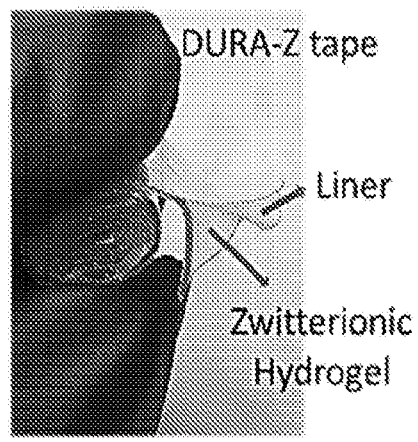
FIG. 1A shows structure of coating composition 1 (called DURA-Z tape in FIG. 1A)

According to aspects of the present invention, compositions include coating compositions, binding compositions, hydrogel-substrate compositions and reverse coated compositions. Such compositions are related, include a hydrogel and are useful as a coating on a substrate.

A coating composition preferentially refers to compositions that could be used in many different applications to coat a surface. Such coating compositions include a hydrophilic hydrogel element and a liner element, wherein a surface of the hydrophilic hydrogel element dissociably-engages a surface of the liner element, and the coating composition lacks a substrate (i.e., the material to be coated).

A binding composition preferentially refers to compositions including a hydrophobic glue and a hydrophilic hydrogel element. Binding compositions are provided according to aspects of the present invention which include a hydrophilic hydrogel element and a hydrophobic glue, wherein the hydrogel includes a hydrogel polymer network and wherein at least a portion of the hydrogel polymer network of the hydrophilic hydrogel element is occupied by the hydrophobic glue.

Binding compositions are provided according to aspects of the present invention which include a hydrophilic hydrogel element and a hydrophobic glue, wherein the hydrogel includes a hydrogel polymer network and wherein at least a portion of the hydrogel polymer network of the hydrophilic hydrogel element is occupied by the hydrophobic glue.

Binding compositions are provided according to aspects of the present invention which include a hydrophilic hydrogel element and a hydrophobic glue comprising a polymer network, wherein the hydrogel includes a hydrogel polymer network and wherein at least a portion of the hydrogel polymer network of the hydrophilic hydrogel element is entangled with the hydrophobic glue.

Binding compositions are provided according to aspects of the present invention which include a hydrophilic hydrogel element and a hydrophobic glue comprising a polymer network, wherein the hydrogel includes a hydrogel polymer network and wherein at least a portion of the hydrogel polymer network of the hydrophilic hydrogel element is entangled with the hydrophobic glue such that the hydrogel polymer network of the hydrophilic hydrogel element and the polymer network of the hydrophobic glue cannot be disentangled without breaking covalent bonds of either the polymer network of the hydrophilic hydrogel element or the polymer network of the hydrophobic glue.

A hydrogel-substrate composition is a composition including a hydrophilic hydrogel element which includes a polymer network; a substrate that includes a surface comprising a polymer network; and the polymer network of the hydrophilic hydrogel element and the polymer network of the surface are entangled, e.g., wherein the gel network of the hydrogel includes a portion of the hydrophobic glue or substrate.

Hydrophilic Hydrogel Element

A hydrophilic hydrogel element has a hydrogel surface characterized by a static water contact angle <90°. In certain embodiments, a hydrophilic hydrogel element has a hydrogel surface characterized by a static water contact angle <60°. In certain embodiments, a hydrophilic hydrogel element has a hydrogel surface characterized by a static water contact angle <30°. In certain embodiments, a hydrophilic hydrogel element has a hydrogel surface characterized by a static water contact angle <15°. In certain embodiments, a hydrophilic hydrogel element has a hydrogel surface characterized by a static water contact angle <5°.

A hydrophilic hydrogel element included in a coating composition, binding composition, and/or hydrogel-substrate composition according to aspects of the present invention can be any hydrophilic hydrogel capable of interacting with a liner element, hydrophobic glue, or substrate as described herein.

Compositions according to aspects of the present invention, including coating compositions, binding compositions, hydrogel-substrate compositions and reverse coated compositions, include a hydrophilic hydrogel element wherein the hydrophilic hydrogel element is a polymer. The hydrophilic hydrogel element typically includes a fluid such as a liquid (e.g., a hydrophilic liquid). According to aspects of the present invention the hydrophilic hydrogel includes water.

A hydrophilic hydrogel element included in a coating composition, binding composition, and/or hydrogel-substrate composition according to aspects of the present invention is or includes a zwitterionic polymer according to aspects of the present invention. The term "zwitterionic" as used herein refers to molecules that carry both positive and negative charges (e.g., negatively-charged carboxylate groups and positively-charged ammonium groups).

A hydrophilic hydrogel element included in a coating composition, binding composition, and/or hydrogel-substrate composition according to aspects of the present invention is or includes a polymer comprising repeating subunits, and the repeating subunits of the polymer are zwitterionic. The hydrophilic hydrogel element may be or include a crosslinked or non-crosslinked polymer. The hydrophilic hydrogel element may be or include a natural or synthetic polymer or network.

The hydrophilic hydrogel element may be or include one or more of: crosslinked poly-acrylic acid, crosslinked poly (vinyl alcohol), non-crosslinked poly(vinyl alcohol), crosslinked poly(vinylpyrrolidone), non-crosslinked poly(vinylpyrrolidone), silicone-containing hydrogel, crosslinked polyacrylamide, crosslinked poly-(N-isopropyl-acrylamide), non-crosslinked poly-(N-isopropyl-acrylamide), crosslinked poly-methyl-methacrylate, poly-hydroxyethyl-methacrylate (PHEMA), crosslinked polyethylene glycol (PEG), crosslinked poly(ethylene glycol) methacrylate (PEGMA), crosslinked poly(ethylene glycol) diacrylate (PEGDA), polypropylene glycol, crosslinked zwitterionic poly-(sulfobetaine methacrylate) (PSBMA), crosslinked zwitterionic 2-methacryloyloxyethyl phosphorylcholine (PMPC), crosslinked zwitterionic poly-carboxybetaine methacrylate (PCBMA), crosslinked zwitterionic poly-carboxybetaine acrylamide (PCBAA), non-crosslinked zwitterionic PCBAA, crosslinked alginate, crosslinked chitosan, gelatin, collagen, fibrin, agarose, hyaluronic acid, cellulose, polypeptides, or a derivative of one or more of the foregoing.

The hydrophilic hydrogel element may be or include a polymer having a structure of formula I:

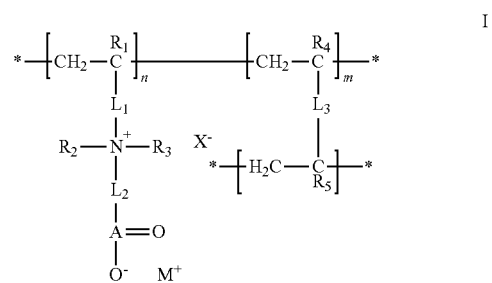

where $R_1$, $R_2$, $R_3$, $R_4$, and $R_5$ are each independently selected from hydrogen, alkyl, and aryl groups; $L_1$ is a linker that covalently couples a cationic center to the polymer backbone; $L_2$ is a linker that covalently couples the cationic center to an anionic group; $A(=O)O^-$ is the anionic group; A is C, S, SO, P, or PO; $X^-$ is a counter ion associated with the cationic center; $M^+$ is a metal ion, an ammonium ion, or an organic ion; $L_3$ is a linker that covalently couples two polymer backbones; n is an integer in the range of 2 to about 100,000; m is a positive non-zero integer; and m/n is in the range of 0.1%-99.9%.

The hydrophilic hydrogel element may be or include a polymer having a structure of formula I where $R_1$, $R_4$, and $R_5$ are each independently selected from the group consisting of hydrogen, fluorine, trifluoromethyl, $C_1$-$C_6$ alkyl, and $C_6$-$C_{12}$ aryl groups; $R_2$ and $R_3$ are independently selected from the group consisting of alkyl and aryl, or taken together with the nitrogen to which they are attached form a cationic center, $L_1$ is a linker that covalently couples the cationic center [N$^+$(R$_2$)(R$_3$)] to a polymer backbone [—(CH$_2$—CR$_1$)$_n$—]; and L$_2$ is a linker that covalently couples an anionic center [A(=O)—O$^-$] to the cationic center.

The structure of formula I, in certain embodiments, is a polymerization product of: a) zwitterionic carboxybetaine monomers, zwitterionic sulfobetaine monomers, and/or zwitterionic phosphobetaine monomers, or a combination of two or more thereof with b) crosslinkers.

A zwitterionic monomer according to aspects of the present invention is selected from the group consisting of: a sulfobetaine acrylate, a sulfobetaine acrylamide, a sulfobetaine vinyl compound, a carboxybetaine acrylate, a carboxybetaine acrylamide, a carboxybetaine vinyl compound, a phosphobetaine acrylate, a phosphobetaine acrylamide, a phosphobetaine vinyl compound; and a mixture of any two or more thereof.

A zwitterionic monomer according to aspects of the present invention is selected from the group consisting of: CBAA, CBMA, [2-(methacryloyloxy)ethyl]dimethyl-(3-sulfopropyl)ammonium hydroxide (SBMA), 2-methacryloyloxyethyl phosphorylcholine (MPC); and a mixture of any two or more thereof.

The hydrophilic hydrogel element according to aspects of the present invention includes a zwitterionic polymer having a plurality of repeating units selected from the group consisting of: a sulfobetaine acrylate, a sulfobetaine methacrylate, a sulfobetaine acrylamide, a sulfobetaine methacrylamide, a sulfobetaine vinyl compound, a carboxybetaine acrylate, a carboxybetaine methacrylate, a carboxybetaine acrylamide, a carboxybetaine methacrylamide, a carboxybetaine vinyl compound, a phosphobetaine acrylate, a phosphobetaine methacrylate, a phosphobetaine acrylamide, a phosphobetaine methacrylamide, a phosphobetaine vinyl compound; and a mixture of any two or more thereof.

A hydrophilic hydrogel element according to aspects of the present invention includes a zwitterionic polymer selected from the group consisting of: a sulfobetaine acrylate polymer, a sulfobetaine methacrylate polymer, a sulfobetaine acrylamide polymer, a sulfobetaine methacrylamide polymer, a sulfobetaine vinyl polymer, a carboxybetaine acrylate polymer, a carboxybetaine methacrylate polymer, a carboxybetaine acrylamide polymer, a carboxybetaine methacrylamide polymer, a carboxybetaine vinyl polymer, a phosphobetaine acrylate polymer, a phosphobetaine methacrylate polymer, a phosphobetaine acrylamide polymer, a phosphobetaine methacrylamide polymer, a phosphobetaine vinyl polymer; a polymer comprising of two or more zwitterionic repeating units selected from the group consisting of: a sulfobetaine acrylate, a sulfobetaine methacrylate, a sulfobetaine acrylamide, a sulfobetaine methacrylamide, a sulfobetaine vinyl compound, a carboxybetaine acrylate, a carboxybetaine methacrylate, a carboxybetaine acrylamide, a carboxybetaine methacrylamide, a carboxybetaine vinyl compound, a phosphobetaine acrylate, a phosphobetaine methacrylate, a phosphobetaine acrylamide, a phosphobetaine methacrylamide, a phosphobetaine vinyl compound; and a mixture of any two or more zwitterionic polymers thereof.

A hydrophilic hydrogel element according to aspects of the present invention includes a zwitterionic polymer selected from the group consisting of: PCBAA, PCBMA, PSBMA, PMPC, and a mixture of any two or more thereof.

The hydrophilic hydrogel element may be or include a polymer having a structure of formula II:

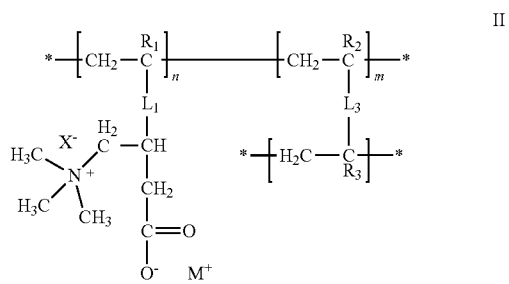

where R$_1$, R$_2$, and R$_3$ are each independently selected from hydrogen, alkyl, and aryl groups; L$_1$, is a linker that covalently couples the polymer sidechain to the polymer backbone; X$^-$ is a counter ion associated with the cationic center; M$^+$ is a metal ion, an ammonium ion, or an organic ion; L$_3$ is a linker that covalently couples two polymer backbones; n is an integer in the range of 2 to about 100,000; m is a positive non-zero integer; and m/n is in the range of 0.1%-99.9%.

The hydrophilic hydrogel element may be or include a polymer having a structure of formula II where R$_1$, R$_2$, and R$_3$ are each independently selected from the group consisting of hydrogen, fluorine, trifluoromethyl, C$_1$-C$_6$ alkyl, and C$_6$-C$_{12}$ aryl groups; L$_1$ is —C(=O)O—(CH$_2$)$_z$— or —C(=O)NH—(CH$_2$)$_z$—; and z is an integer from 1 to 20.

The structure of formula II, in certain embodiments, is a polymerization product of zwitterionic carnitine derived monomers with crosslinkers.

A zwitterionic carnitine derived monomer according to aspects of the present invention is selected from the group consisting of: a carnitine derived acrylate, a carnitine derived acrylamide, a carnitine derived vinyl compound; and a mixture of any two or more thereof.

A zwitterionic carnitine derived monomer according to aspects of the present invention is selected from the group consisting of L-carnitine acrylate monomer.

The hydrophilic hydrogel element may be or include a polymer having a structure of formula III:

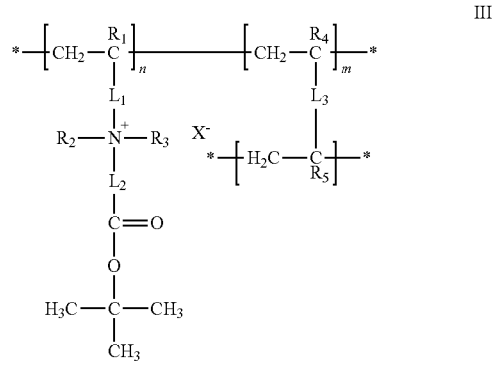

where R$_1$, R$_2$, R$_3$, R$_4$, and R$_5$ are each independently selected from hydrogen, alkyl, and aryl groups; L$_1$ is a linker that covalently couples a cationic center to the polymer backbone; L$_2$ is a linker that covalently couples the cationic center to an anionic group; X$^-$ is a counter ion associated with the cationic center; L$_3$ is a linker that covalently couples two polymer backbones; n is an integer in the range of 2 to about 100,000; m is a positive non-zero integer; and m/n is in the range of 0.1%-99.9%.

The hydrophilic hydrogel element may be or include a polymer having a structure of formula III, where $R_1$, $R_4$, and $R_5$ are each independently selected from the group consisting of hydrogen, fluorine, trifluoromethyl, $C_1$-$C_6$ alkyl, and $C_6$-$C_{12}$ aryl groups; $R_2$ and $R_3$ are independently selected from the group consisting of alkyl and aryl, or taken together with the nitrogen to which they are attached form a cationic center; $L_1$ is a linker that covalently couples the cationic center [$N^+(R_2)(R_3)$] to a polymer backbone [—($CH_2$—$CR_1)_n$—]; and $L_2$ is a linker that covalently couples an anionic center [$C(=O)$—$O^-$] to the cationic center.

The structure of formula III is a polymerization product of zwitterionic carboxybetaine ester monomers with crosslinkers, A zwitterionic carboxybetaine ester monomer according to aspects of the present invention is selected from the group consisting of: a carboxybetaine ester acrylate, a carboxybetaine ester acrylamide, a carboxybetaine ester vinyl compound; and a mixture of any two or more thereof.

A zwitterionic carnitine derived monomer according to aspects of the present invention is selected from the group consisting of CBAA-tBu monomer.

A crosslinker reacted with a monomer to form the structure of formula I, II, or III, in certain embodiments, according to aspects of the present invention is a polyreactive crosslinking agent. According to particular aspects, a crosslinker reacted with a zwitterionic monomer, a zwitterionic carnitine derived monomer, or a zwitterionic carboxybetaine ester monomer to produce a hydrophilic hydrogel element according to aspects of the present invention is an acryloyl-containing crosslinker. According to particular aspects, a crosslinker reacted with a zwitterionic monomer, a zwitterionic carnitine derived monomer, or a zwitterionic carboxybetaine ester monomer to produce a hydrophilic hydrogel element according to aspects of the present invention is an allyl crosslinker. According to particular aspects, a crosslinker reacted with a zwitterionic monomer, a zwitterionic carnitine derived monomer, or a zwitterionic carboxybetaine ester monomer to produce a hydrophilic hydrogel element according to aspects of the present invention is a vinyl compound.

A crosslinker reacted with a zwitterionic monomer, a zwitterionic carnitine derived monomer, or a zwitterionic carboxybetaine ester monomer according to aspects of the present invention is one or more of: allyl methacrylate, diallyl itaconate, monoallyl itaconate, diallyl maleate, diallyl fumarate, diallyl succinate, diallyl phthalate, triallyl cyanurate, triallyl isocyanurate, diethylene glycol bis-allyl carbonate, divinyl ether of diethylene glycol, triallyl phosphate, triallyl trimellitate, allyl ether, diallylimidazolidone, pentaerythritol triallyl ether (PETE), N,N-diallylmelamine, triallyl-1,3,5-triazine-2,4,6-(1H,3H,5H)trione (TATT), 2,4,6-Triallyloxy-1,3,5-triazine; vinyl compounds, e.g. divinyl benzene, N,N'-methylene bis acrylamide (MBAA), methylenebis(methacrylamide), ethylene glycol dimethacrylate, ethylene glycol diacrylate, neopentylglycol dimethacrylate, tetraethylene glycol dimethacrylate, polyethylene glycol dimethacrylate, polyethylene glycol diacrylate, hexamethylene bis maleimide, divinyl urea, bisphenol A bis methacrylate, divinyl adipate, glycerin trimethacrylate, trimethylolpropane triacrylate, trivinyl trimellitate, 1,5-pentadiene, 1,7-octadiene, 1,9-decadiene, 1,3-bis(4-methacryloxybutyl) tetramethyl disiloxane, divinyl ether, divinyl sulfone, N-vinyl-3(E)-ethylidene pyrrolidone (EVP), ethylidene bis(N-vinyl pyrrolidone) (EBVP).

A crosslinker reacted with a zwitterionic monomer, a zwitterionic carnitine derived monomer, or a zwitterionic carboxybetaine ester monomer according to aspects of the present invention is MBAA.

The length, width and overall shape of a hydrophilic hydrogel element are not particularly limiting, and they may be selected based on the desired use of the hydrophilic hydrogel element. The use of hydrophilic hydrogel element to coat large surfaces may favor compositions with hydrophilic hydrogel elements that have large lengths and widths whereas the use of hydrophilic hydrogel elements to coat smaller surfaces may favor compositions with hydrophilic hydrogel elements that have smaller lengths and widths, but such factors are not dispositive as multiple small hydrophilic hydrogel elements may be used to coat large surfaces and a large hydrophilic hydrogel element may be cut to coat smaller surfaces.

The thickness of a hydrophilic hydrogel element should be large enough such that the hydrophilic hydrogel element functions appropriately, e.g., to protect an underlying surface. According to aspects of the disclosure, the thickness of the hydrophilic hydrogel element is about 1 μm to about 10 cm, about 10 μm to about 5 cm, about 10 μm to about 1 cm, about 50 μm to about 5 mm, about 100 μm to about 1 cm, about 500 μm to about 5 cm, about 10 μm to about 1 mm, about 50 μm to about 5 mm, about 100 μm to about 1 cm, about 500 μm to about 5 cm, about 10 μm to about 100 μm, about 50 μm to about 500 μm, about 100 μm to about 1 mm, about 500 μm to about 5 mm thick, about 1 mm to about 1 cm, or about 5 mm to about 5 cm thick. Hydrophilic hydrogel elements thicker than 1 cm may be desirable for hydrophilic hydrogel elements used to coat large surfaces.

In particular aspects of the invention, a hydrophilic hydrogel element includes two substantially parallel surfaces, and the distance between the two substantially parallel surfaces is about 1 μm to about 10 cm, about 10 μm to about 5 cm, about 10 μm to about 1 cm, about 50 μm to about 5 mm, about 100 μm to about 1 cm, about 500 μm to about 5 cm, about 10 μm to about 1 mm, about 50 μm to about 5 mm, about 100 μm to about 1 cm, about 500 μm to about 5 cm, about 10 μm to about 100 μm, about 50 μm to about 500 μm, about 100 μm to about 1 mm, about 500 μm to about 5 mm thick, about 1 mm to about 1 cm, or about 5 mm to about 5 cm.

The thickness of a hydrophilic hydrogel element may vary depending on its stiffness and desired use. The stiffness of a PCBAA hydrophilic hydrogel element can be altered, for example, by changing the MBAA crosslinker density. For example, increasing molar ratios of the MBAA crosslinker can be added to CBAA monomer to produce PCBAA hydrophilic hydrogel elements with increasing stiffness. Hydrophilic hydrogel elements generated from other polymers may be altered analogously.

The shape of a hydrophilic hydrogel element defined by its length and width may vary depending on its desired use.

In particular aspects of the invention, a hydrophilic hydrogel element is substantially-flat, i.e., the hydrophilic hydrogel element has two substantially-parallel surfaces (e.g., analogous to the front and back of a piece of paper). A hydrophilic hydrogel element has a length, width, and thickness. In certain embodiments, the surface of a hydrophilic hydrogel element that dissociably-engages a liner corresponds to a surface defined by the length and width of the hydrophilic hydrogel element.

Liner Element

According to particular aspects, a composition of the present invention includes a hydrophilic hydrogel element and a liner element. A surface of the hydrophilic hydrogel element dissociably-engages a surface of the liner element.

The liner element can include a polymer surface, e.g., wherein the polymer surface of the liner element contacts a hydrophilic hydrogel element. A surface of the liner element (e.g., a polymer surface) can allow a hydrogel to dissociably-engage the liner. Suitable compositions of a surface of a liner element that allow a hydrophilic hydrogel element to dissociably-engage the liner element include any of various materials that are substantially inert with respect to the hydrophilic hydrogel element and effective to dissociably engage with the hydrophilic hydrogel element such as, but not limited to, paper, cellulose, acrylic, nylon, polyethylene, polypropylene, acetate, polyester, polyimide, polyurethane, polystyrene, polycarbonate, polyvinylidene chloride, ethylene-vinyl acetate copolymer, a ceramic, mixtures of any two or more thereof or layered combinations of any two or more thereof. Optionally, the liner element includes a hydrophobic material, such as, but not limited to polypropylene, which is substantially inert with respect to the hydrophilic hydrogel element and effective to dissociably engage with the hydrophilic hydrogel element.

In particular aspects of the invention, a liner element is substantially-flat, i.e., the liner element has two substantially-parallel surfaces (e.g., analogous to the front and back of a piece of paper). The liner element has a length, width, and thickness. According to aspects of the present invention, the liner is sheetlike, having two parallel surfaces and a generally uniform thickness extending therebetween.

Figure 1B:
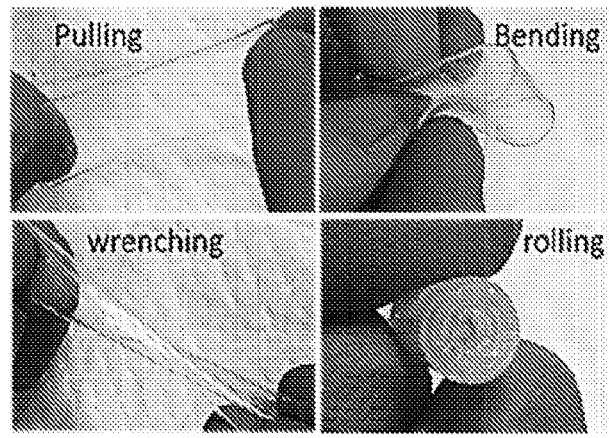
FIG. 1B shows Coating composition 1 under pulling, bending, wrenching and rolling conditions.

In certain embodiments, the surface of a liner element that dissociably-engages a hydrophilic hydrogel element corresponds to a surface defined by the length and width of the liner element. For example, as shown in FIG. 1D, a coating composition 10 includes: 1) a liner element 20 having a top surface 30 and a bottom surface 40; and 2) a hydrophilic hydrogel element 50 having a top surface 60 and a bottom surface 70, wherein the bottom surface of the liner element 40 is dissociably engaged with the top surface of the hydrophilic hydrogel element 60.

The length and width of a liner element are not particularly limiting, and they may be selected based on the desired use of a hydrogel. The use of a hydrogel to coat large surfaces may favor compositions with liner elements (and hydrophilic hydrogel elements) that have large lengths and widths whereas the use of hydrogels to coat smaller surfaces may favor compositions with liner elements (and hydrophilic hydrogel elements) that have smaller lengths and widths, but such factors are not dispositive as multiple small hydrophilic hydrogel elements may be used to coat large surfaces and a large hydrophilic hydrogel element may be cut to coat smaller surfaces.

The thickness of a liner element is large enough such that the liner element does not readily break or tear. Thicker liner elements may be desirable to help stabilize a composition. Thinner liner elements may be desirable to manipulate a composition (e.g., roll or bend a composition). The thickness of the liner element may also be adjusted based in part on the composition and/or physical properties of the liner, e.g., liner elements made from flexible materials may be thicker than liner elements made from rigid materials. According to aspects of the disclosure, the thickness of the liner element is about 1 µm to about 1 cm, about 50 µm to about 5 mm, about 100 µm to about 1 mm, about 10 µm to about 1 mm, about 50 µm to about 5 mm, about 10 µm to about 100 µm, about 50 µm to about 500 µm, about 100 µm to about 1 mm, or about 500 µm to about 5 mm thick. The thickness of the liner element is generally in the range of about 10 µm to about 10 cm thick, such as about 1 µm to about 5 cm thick, about 1 µm, 2 µm, 3 µm, 4 µm, 5 µm, 6 µm, 7 µm, 8 µm, 9 µm, 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1 mm, 2 mm, 3 mm, 4 mm, 5 mm, 6 mm, 7 mm, 8 mm, 9 mm, 1 cm, 2 cm, 3 cm, 4 cm, 5 cm, 6 cm, 7 cm, 8 cm, 9 cm, or 10 cm. Liner elements thicker than 1 cm may be desirable for hydrogels used to coat large surfaces.

The shape of a liner element defined by its length and width is not particularly limiting, although liner elements may have substantially-rectangular shapes that result from convenient manufacturing methods.

For example, a hydrogel optionally includes a substantially-flat surface, a liner may include a substantially-flat surface, the substantially-flat surface of the hydrogel is in contact with the substantially-flat surface of the liner, and the hydrogel is capable of being separated from the liner, e.g., by peeling the liner off of the hydrogel or by peeling the hydrogel off of the liner.

A "substantially-flat surface" refers to a substantially smooth and even surface. A substantially-flat surface is optionally a two-dimensional surface which is further optionally incorporated in a more complex shape. For example, a substantially-flat surface may be rolled or bent.

According to aspects of the present invention, a coating composition is provided which includes a hydrophilic hydrogel element and a liner element, wherein the liner element has two parallel substantially planar surfaces: a top liner element surface and a bottom liner element surface; the hydrophilic hydrogel element has two parallel substantially planar surfaces: a top hydrophilic hydrogel element surface and a bottom hydrophilic hydrogel element surface; and the coating composition is in the form of a roll or a sheet-like panel; wherein at least 50%, 60%, 70%, 80%, 90%, 95%, 99% or all of the top-surface of the hydrophilic hydrogel element dissociably-engages the bottom-surface of the liner element; and at least 50%, 60%, 70%, 80%, 90%, 95%, 99% or all of the bottom-surface of the hydrophilic hydrogel element dissociably-engages the top-surface of the liner element.

In particular aspects of the invention, a composition includes a liner element and a hydrophilic hydrogel element, and the composition is a rolled sheet. For example, the liner element can have a top surface and a bottom surface, the hydrophilic hydrogel element can have a top surface and a bottom surface, the top-surface of the hydrophilic hydrogel element can dissociably-engage the bottom-surface of the liner element, and the bottom-surface of the hydrophilic hydrogel element can dissociably-engage the top-surface of the liner element. Such compositions are similar to rolls of double-sided tape in which the tape is protected by a liner element.

According to aspects of the present invention, a coating composition is provided which includes a hydrophilic hydrogel element, a first liner element, and a second liner element, wherein the first and second liner elements each have two parallel substantially planar surfaces: a top first liner element surface and a bottom first liner element surface, a top second liner element surface and a bottom second liner element surface; the hydrophilic hydrogel element has two parallel substantially planar surfaces: a top hydrophilic hydrogel element surface and a bottom hydrophilic hydrogel element surface; and the coating composition is in the form of a roll or a sheet-like panel; wherein at least 50%, 60%, 70%, 80%, 90%, 95%, 99% or all of the top-surface of the hydrophilic hydrogel element dissociably-engages the bottom-surface of the first liner element; and at least 50%, 60%, 70%, 80%, 90%, 95%, 99% or all of the bottom-surface of the hydrophilic hydrogel element dissociably-engages the top-surface of the second liner element.

In particular aspects of the invention, a composition includes a hydrophilic hydrogel element, a first liner element, and a second liner element. For example, a hydrophilic hydrogel element can have a top surface and a bottom surface, the top surface of the hydrophilic hydrogel element can dissociably-engage the liner element, and the bottom-surface of the hydrophilic hydrogel element can dissociable-engage the second liner element. Such compositions allow the two liner elements to protect two surfaces of a hydrophilic hydrogel element. For example, as shown in FIG. 1E a coating composition 100 includes: 1) a first liner element 120 having a top surface 130 and a bottom surface 140; 2) a second liner element 120a having a top surface 130a and a bottom surface 140a; and 3) a hydrophilic hydrogel element 150 having a top surface 160 and a bottom surface 170, wherein the bottom surface of the first liner element 140 is dissociably engaged with the top surface of the hydrophilic hydrogel element 160 and the bottom surface of the second liner element 140a is dissociably engaged with the top surface of the hydrophilic hydrogel element 170.

Hydrophobic Glue

In particular aspects of the invention, a composition includes a hydrophobic glue. In some embodiments, at least a portion of the gel network of the hydrogel is occupied by the hydrophobic glue. The hydrophobic glue helps adhere a hydrogel to a surface for example, by entangling the polymers of a hydrophilic hydrogel element with the polymers of the hydrophobic glue, e.g., thereby forming a physical linkage between the hydrophilic hydrogel element and the hydrophobic glue. A physical linkage between a hydrophobic glue and a hydrophilic hydrogel element may be analogous to the links of a chain, i.e., the links of a chain are not chemically bound and yet the links may not be separable without breaking chemical bonds.

In particular aspects of the invention, a composition includes a hydrophobic glue and a hydrogel, at least a portion of the gel network of the hydrogel is occupied by the hydrophobic glue, and the hydrophobic glue and the hydrogel cannot be separated without breaking covalent bonds. The hydrophobic glue is optionally covalently-bound to the hydrogel. In some embodiments, the hydrophobic glue is not covalently-bound to the hydrogel, and yet the hydrophobic glue cannot be separated from the hydrogel without breaking covalent bonds.

A non-limiting list of included hydrophobic glues is one or more of: cyanoacrylate, ethyl cyanoacrylate, butyl cyanoacrylate, isobutyl cyanoacrylate, octyl cyanoacrylate, 2-octyl cyanoacrylate, other cyanoacrylate derivatives, metal adhesive, an epoxy-based adhesive or derivative thereof, a polyurethane-based adhesive or derivative thereof, and a styrene-butadiene adhesive or derivative thereof.

A non-limiting list of included hydrophobic glues is one or more of: cyanoacrylate superglue, ethyl cyanoacrylate, butyl cyanoacrylate, isobutyl cyanoacrylate, octyl cyanoacrylate, 2-octyl cyanoacrylate, other cyanoacrylate derivatives, 3M metal adhesive, EVO-STIK SERIOUS GLUE, Qatey HANDY PACK PVC CEMENT, Loctite Liquid Professional Super Glue, Gorilla Super Glue Gel, epoxy-based adhesives and their derivatives (e.g., MarineWeld™ by J-B Weld), polyurethane-based adhesives and their derivatives (e.g., Marine Adhesive Sealant by 3M), styrene-butadiene adhesives and their derivatives (e.g., Marine Adhesive by Amazing Goop), the generic equivalent of any of the foregoing, or the active ingredient(s) of any of the foregoing.

A non-limiting list of included hydrophobic glues is one or more of: nitrocellulose adhesive, rubber cement, polyvinyl acetate, polyester resin, polyurethane resin, polyols, acrylic polymer, thermoset resin, polyuria/polyurethane, vulcanized rubber, phenol-formaldehyde, duroplast, melamine resin, diallyl-phthalate, epoxy resin, benzoxazine, polyimide, bismaleimide, cyanate ester, furan resin, silicone resin, or vinyl ester resin.

In particular aspects of the invention, a composition includes a polymeric hydrophobic glue. The polymeric hydrophobic glue is optionally cured. A "cured" hydrophobic glue is a hydrophobic glue that has been transformed from the state in which the hydrophobic glue is unbonded (e.g., a flowable state or monomeric state) to a state in which the hydrophobic glue is bonded (e.g., a hardened state or polymeric state).

Substrate

In particular aspects of the invention, a composition includes a substrate. The term "substrate" as used herein refers to a material that is modified with a hydrogel or a material to be modified with a hydrogel.

A composition can include a substrate, hydrophobic glue, and hydrogel. A composition can include a substrate and hydrogel (and lack a hydrophobic glue). For example, the substrate includes a surface which includes a polymer network or a continuous phase; and the polymer network or the continuous phase of the hydrogel and the polymer network or the continuous phase of the surface are entangled at a physical region between the hydrogel coating domain and the surface domain of the substrate. FIG. 1H illustrates a substrate-hydrogel composition 400, including a substrate 495 which includes a surface 485 which includes a polymer network or a continuous phase; and the polymer network or the continuous phase of the hydrophilic hydrogel element 450 and the polymer network or the continuous phase of the surface are entangled at a physical region 475 between the hydrogel coating domain and the surface domain of the substrate In particular aspects of the invention, a composition includes a substrate and a hydrophobic glue, and the substrate is bonded to the hydrophobic glue. The composition may further include a hydrogel, and the hydrophobic glue and hydrogel may be associated with each other, e.g., as described herein. For example, the polymeric structure of the hydrophobic glue may be entangled with the polymeric structure of the hydrogel such that the hydrophobic glue and hydrogel cannot be separated without breaking covalent bonds.

In particular aspects of the invention, a composition includes a substrate, a hydrophobic glue, and a hydrogel, and the hydrophobic glue adheres to a surface of the substrate, thereby connecting the substrate and the hydrogel.

According to aspects of the present invention, the thickness of the entanglement region where the polymeric structure of the hydrophobic glue and the polymeric structure of the hydrogel are entangled, is influenced by a variety of factors including the material type, stiffness, water content or other solvent condition, porosity, and thickness of hydrophilic hydrogel element, and the material type, molecular size, concentration, and viscosity of the hydrophobic glue, the pressure and time applied to contact hydrophobic glue with the hydrophilic hydrogel element, and the curing or solidifying condition for the hydrophobic glue. Conditions allowing deeper penetration of the hydrophobic glue into the hydrophilic hydrogel element, including but not limited to high porosity of the hydrophilic hydrogel element, small molecular size and high dissolution property of the hydrophobic glue in the hydrophilic hydrogel element network, high pressure and longer time applied to contact the hydrophobic glue with the hydrophilic hydrogel element, result in a higher thickness of the entanglement region.

In particular aspects of the invention, the surface of the substrate is or includes agarose, alginate, poly-hydroxyethyl-methacrylate (PHEMA), polydimethylsiloxane (PDMS), polyurethane (PU), polystyrene (PS), PVC panel, silicone rubber, silicone hydrogel, epoxy, epoxy-coated steel, glass, ceramic, plastic, metal, wood, or a derivative of any of the foregoing or a combination of any two or more of the foregoing.

In particular aspects of the invention where a binding composition is applied, the substrate is a painted or fiberglass boat or ship hull or other marine surface.

In particular aspects of the invention where a reverse coating method is used, a preferred substrate is a polyHEMA or polystyrene (PS) surface of a medical device.

Chemical Composition

A polymer having a structure of formula II:

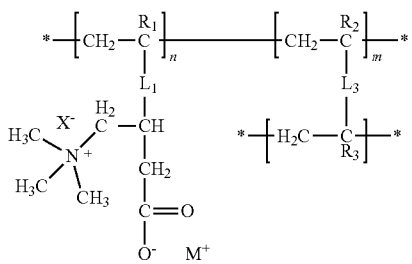

is provided according to aspects of the present invention where $R_1$, $R_2$, and $R_3$ are each independently selected from hydrogen, alkyl, and aryl groups; $L_1$ is a linker that covalently couples the polymer sidechain to the polymer backbone; $X^-$ is a counter ion associated with the cationic center; $M^+$ is a metal ion, an ammonium ion, or an organic ion; $L_3$ is a linker that covalently couples two polymer backbones; n is an integer in the range of 2 to about 100,000; m is a positive non-zero integer; and m/n is in the range of 0.1%-99.9%.

A polymer having a structure of formula II is provided according to aspects of the present invention, where $R_1$, $R_2$, and $R_3$ are each independently selected from the group consisting of hydrogen, fluorine, trifluoromethyl, $C_1$-$C_6$ alkyl, and $C_6$-$C_{12}$ aryl groups; $L_1$ is —C(=O)O—$(CH_2)_z$— or —C(=O)NH—$(CH_2)_z$—; and z is an integer from 1 to 20.

Article of Manufacture

Articles of manufacture, such as, but not limited to, devices and components of devices, are provided according to aspects of the present invention which are produced according to methods of the present invention.

Articles of manufacture, such as, but not limited to, devices and components of devices, are provided according to aspects of the present invention which include a surface at least partially covered by a composition of the present invention.

Various aspects of the invention relate to a medical device including a composition described herein and/or produced by a method described herein. The composition can include a hydrogel, e.g., wherein a surface of the medical device is at least partially covered by the hydrogel. The composition may comprise a substrate. A substrate can be bound either directly to a hydrogel, or the substrate can be bound to a hydrophobic glue that is directly bound to the hydrogel. The medical device can be, for example, an implantable medical device or a surgical instrument, exemplified by, but not limited to, blood or tissue contacting devices such as stents, artificial blood vessels, catheters, tubing, and dialysis devices such as dialysis membrane and dialysis tubing.

Various aspects of the invention relate to a water-immersible device including a composition described herein and/or produced by a method described herein. The composition can include a hydrogel, e.g., wherein a surface of the water-immersible device is at least partially covered by the hydrogel. The composition may comprise a substrate. A substrate can be bound either directly to a hydrogel, or the substrate can be bound to a hydrophobic glue that is directly bound to the hydrogel. The water-immersible device can be, for example, a component of a watercraft, such as a boat or ship hull, marine foundation, dock, lock, dam, water-treatment plant, underwater cable, offshore drill, or offshore well, cooling line for a nuclear reactor, or an instrument or tool for operating or maintaining any one of the foregoing.

Methods

Various aspects of the invention relate to methods for applying a hydrophilic polymer hydrogel to a surface (e.g., a surface of a substrate as described herein). A method can include contacting the surface with a hydrophobic glue (e.g., any hydrophobic glue described herein). A method can include contacting a hydrophobic glue with the hydrogel (e.g., any hydrogel described herein). A method can optionally include increasing the surface area of a substrate (e.g., with an abrasive such as sandpaper), which may increase the bonding strength between the substrate and the hydrophobic glue.

In some embodiments, a method includes curing the hydrophobic glue (e.g., using any method described herein). A method can include curing the hydrophobic glue for at least about 1, 5, 10, 15, 20, 25, 30, 45, 60 minutes or at least about 1, 2, 6, or 12 hours. A method can include applying pressure to the hydrogel after contacting the hydrophobic glue with the hydrogel. Applying pressure to the hydrogel may facilitate binding of the hydrophobic glue and hydrogel. A method can include applying at least about 0.01, 0.1, 0.2, 0.3, 0.4, 0.5, 1.0, 1.5, 2.0, 2.5, 3, 4, 5, 6, 7, 8, 9, 10, 11, 12, 15, or 20 kPa of pressure to the hydrogel.

Figure 1C:
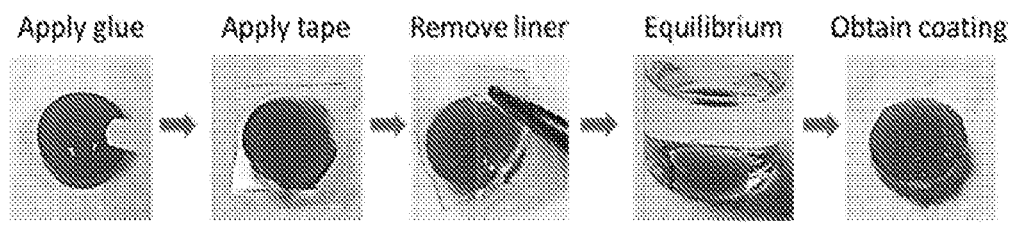
FIG. 1C illustrates steps in fabrication of the coating on PU substrate (binding composition 1).
Figure 1D:
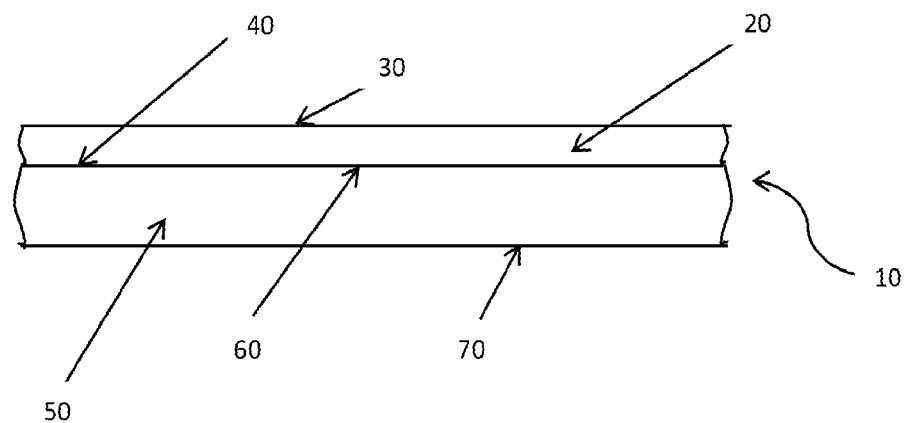
FIG. 1D is a diagram showing a coating composition including a liner element and a hydrophilic hydrogel element.
Figure 1E:
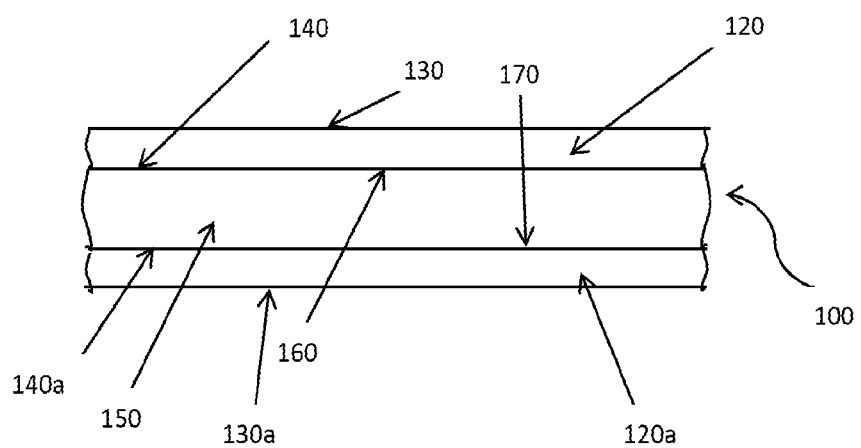
FIG. 1E is a diagram showing a coating composition including a first liner element, a second liner element and a hydrophilic hydrogel element disposed between the first liner element and the second liner element.
Figure 1F:
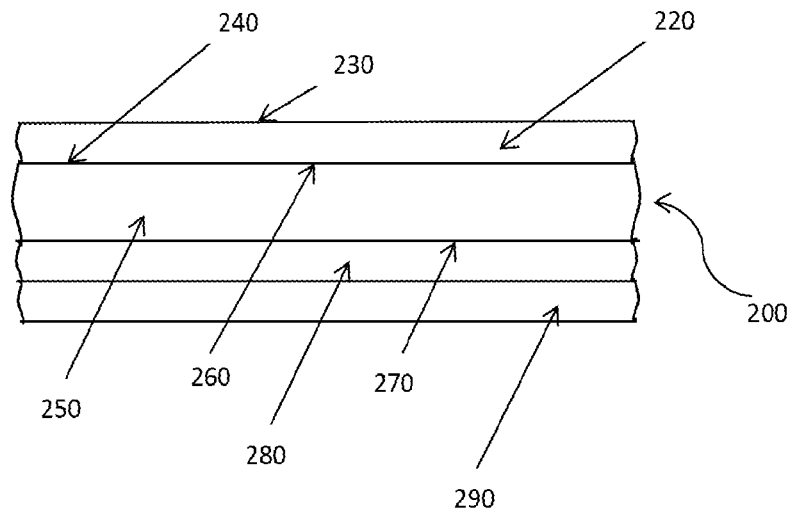
FIG. 1F is a diagram showing a binding composition 200 including a hydrophilic hydrogel element 250 in contact with a hydrophobic glue 290 and showing a region 280 in which the bottom surface 270 of the hydrophilic hydrogel element 250 and the hydrophobic glue 290 are entangled; a liner element 220 having a top surface 230 and a bottom surface 240; is also shown in contact with the hydrophilic hydrogel element 250 at a top surface 260 of the hydrophilic hydrogel element 250.
Figure 1G:
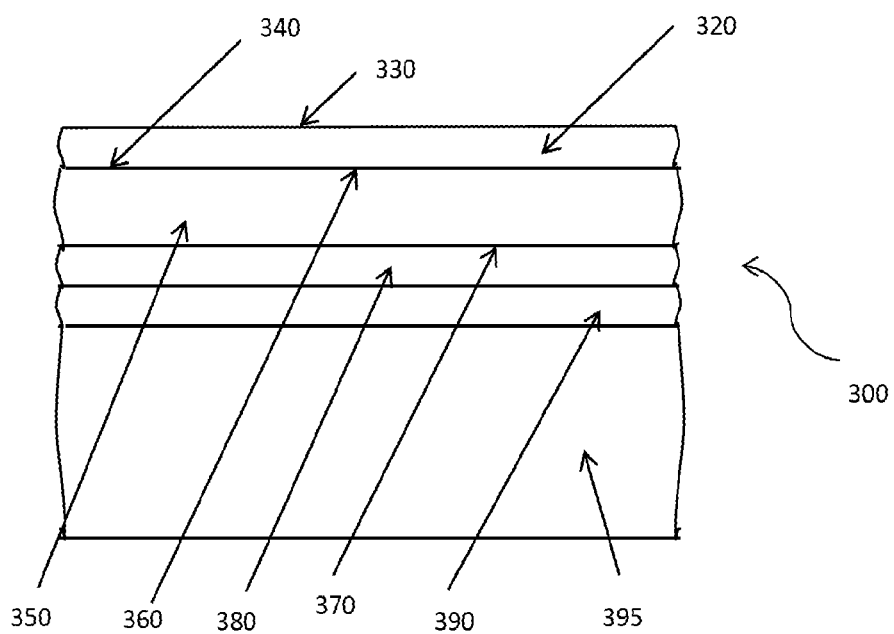
FIG. 1G is a diagram showing a binding composition 300 including a hydrophilic hydrogel element 350 which has a top surface 360 and a bottom surface 370 in contact with a hydrophobic glue 390 and showing a region 380 in which the hydrophilic hydrogel element 350 and the hydrophobic glue 390 are entangled; a liner element 320 having a top surface 330 and a bottom surface 340 is shown in contact with the hydrophilic hydrogel element 350 and the hydrophobic glue 390 is shown on the substrate 395 which is effectively coated with the hydrogel.
Figure 1H:
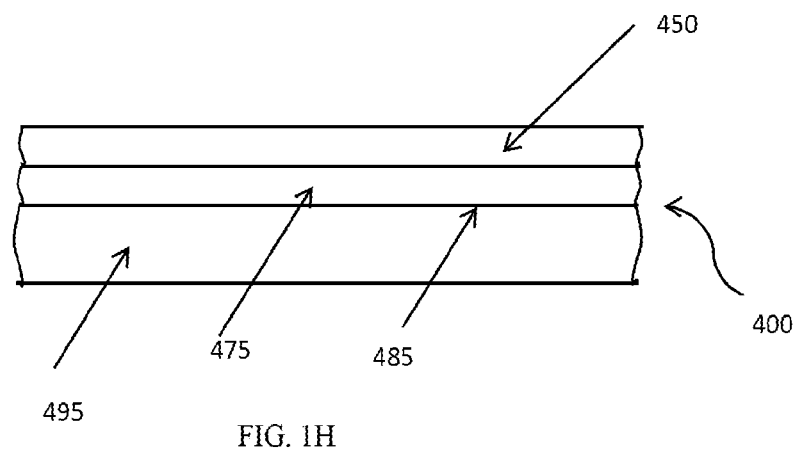
FIG. 1H is a diagram showing a hydrogel-substrate composition in which the hydrophilic hydrogel element and the substrate are entangled such that the substrate is effectively coated with the hydrogel.

For example, as shown in FIG. 1C, a hydrophobic glue can be applied to a substrate, a coating composition including a hydrophilic hydrogel element and a liner element is then placed so that a surface of the hydrophilic hydrogel element is brought into direct contact with the hydrophobic glue. The liner can then be removed, producing a hydrogel coated substrate. Optionally, the substrate with the hydrophilic hydrogel element in direct contact with the hydrophobic glue is then exposed to a liquid, such as water, to equilibrate the hydrophilic hydrogel element, producing a water-equilibrated hydrogel coated substrate.

A coating composition including a liner element and a hydrophilic hydrogel element together with a hydrophobic glue can be hand-applied or mechanically applied to any substrate by an user.

The coating composition comprising the liner and the hydrogel coating layer (e.g., hydrogel tape), alternatively, can be mounted to an applicator, such as a roller, which applies the hydrophobic glue and bind the hydrogel coating composition to a substrate in a convenient way. The application of hydrophobic glue could be hand-triggered or automatically and could be based on electrical or mechanical mechanism. The hydrophobic glue container could be inside the roller to conveniently apply the hydrophobic glue in the path of the roller. Alternatively, the hydrophobic glue can be applied by a separate roller or other device, or manually applied, such as by "painting" onto a substrate.

A binding composition including a liner element and a hydrophilic hydrogel element and a hydrophobic glue wherein at least a surface portion of the hydrophobic glue is entangled with at least a portion of a surface of the hydrophilic hydrogel element can be hand-applied or mechanically applied to any substrate by an user.

The binding composition comprising the liner, the hydrogel coating layer and the hydrophobic glue (part of the hydrophobic glue layer entangled with part of the hydrogel coating layer) can be applied to any substrates facilitated with a commercial tape applicator.

Provided according to aspects of the present disclosure is a coating composition 1 and a method to produce it, comprising a zwitterionic PCBAA hydrogel coating and a liner.

Provided according to aspects of the present disclosure is a binding composition 1 and a method to produce it, comprising a zwitterionic PCBAA hydrogel coating, superglue, and a substrate.

Provided according to aspects of the present disclosure is a coating composition 2 and a method to produce it, comprising a zwitterionic PCBMA hydrogel coating and a liner.

Provided according to aspects of the present disclosure is a binding composition 2 and a method to produce it, comprising a zwitterionic PCBMA hydrogel coating, superglue, and a substrate.

Provided according to aspects of the present disclosure is a coating composition 3 and a method to produce it, comprising a zwitterionic PSBMA hydrogel coating and a liner.

Provided according to aspects of the present disclosure is a binding composition 3 and a method to produce it, comprising a zwitterionic PSBMA hydrogel coating, superglue, and a substrate.

Provided according to aspects of the present disclosure is a coating composition 4 and a method to produce it, comprising a zwitterionic PMPC hydrogel coating and a liner.

Provided according to aspects of the present disclosure is a binding composition 4 and a method to produce it, comprising a zwitterionic PMPC hydrogel coating, superglue, and a substrate.

Provided according to aspects of the present disclosure is a coating composition 5 and a method to produce it, comprising a zwitterionic PEG hydrogel coating and a liner.

Provided according to aspects of the present disclosure is a binding composition 5 and a method to produce it, comprising a zwitterionic PEG hydrogel coating, superglue, and a substrate.

Provided according to aspects of the present disclosure are coating compositions 6, 7, 8, 9 and a method to produce them, comprising a zwitterionic PCBAA-polyacrylamide hydrogel coating with varied PCBAA compositions and a liner.

Provided according to aspects of the present disclosure are binding compositions 6, 7, 8, 9 and a method to produce them, comprising a zwitterionic PCBAA-polyacrylamide hydrogel coating with varied PCBAA compositions, superglue, and a substrate.

Reverse Coating

Various aspects of the invention relate to reverse coating methods for making a hydrogel-coated material. A reverse coating method 600 for making a hydrogel-coated material 645 is shown schematically in FIG. 1J. As shown, the method includes preparing 610 a hydrogel 615 in a desired shape. The hydrogel may be any hydrogel described herein. A reverse coating method can include contacting 620 a hydrogel 615 with a flowable form of a substrate 625 resulting in at least a portion of the flowable substrate 625 entering the hydrogel, producing an interpenetrating region 635. A reverse coating method includes solidifying or curing the flowable form of the substrate 625, producing a reverse-coated substrate composition 645 having an interpenetrating region 635.

The interpenetrating region 635 has the polymer network or continuous phase of the hydrophilic hydrogel element 615 and the polymer network or continuous phase of the cured or solidified substrate entangled.

Fixing a hydrogel in a desired shape can include forming the hydrogel on a surface or in a mold. For example, a hydrogel may be formed on a polymer surface (e.g., a polypropylene surface) thereby fixing the hydrogel in a desired shape (e.g., a flat shape). For example, see FIG. 1J.

A flowable substrate can be a liquid, suspension, colloid, or powder. The flowable substrate can be cured or solidified, for example, by heating or cooling the substrate, drying the substrate, evaporating solvent, or irradiating the substrate with microwave, infrared, visible, or ultraviolet radiation. A reverse coating method can include curing or solidifying the substrate for at least about 1, 5, 10, 15, 20, 25, 30, 45, 60 minutes or at least about 1, 2, 6, or 12 hours. The flowable substrate may comprise or consist of plastic, silicone, metal, or molecules capable of polymerization.

A reverse coating composition includes a first formed hydrophilic hydrogel element and a later formed substrate element wherein the hydrophilic hydrogel element is in contact and covers at least a portion of the later formed substrate element.

According to aspects of the present invention, the hydrophilic hydrogel element of the reverse coating composition includes a polymer network or a continuous phase.

According to aspects of the present invention, the substrate includes a surface which includes a polymer network or a continuous phase; and the polymer network or the continuous phase of the hydrophilic hydrogel element and the polymer network or the continuous phase of the surface are entangled at a physical region between the hydrogel coating domain and the surface domain of the substrate.

Figure 1I:
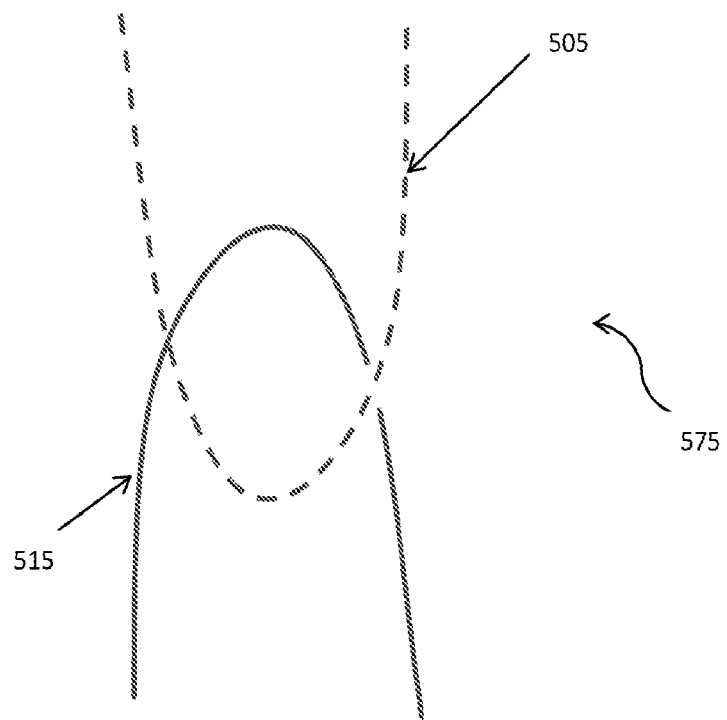
FIG. 1I is a diagram illustrating entanglement 575 between at least a portion of a hydrogel polymer 505 of a hydrophilic hydrogel element and a polymer network or continuous phase of the surface of a substrate 515.
Figure 1J:
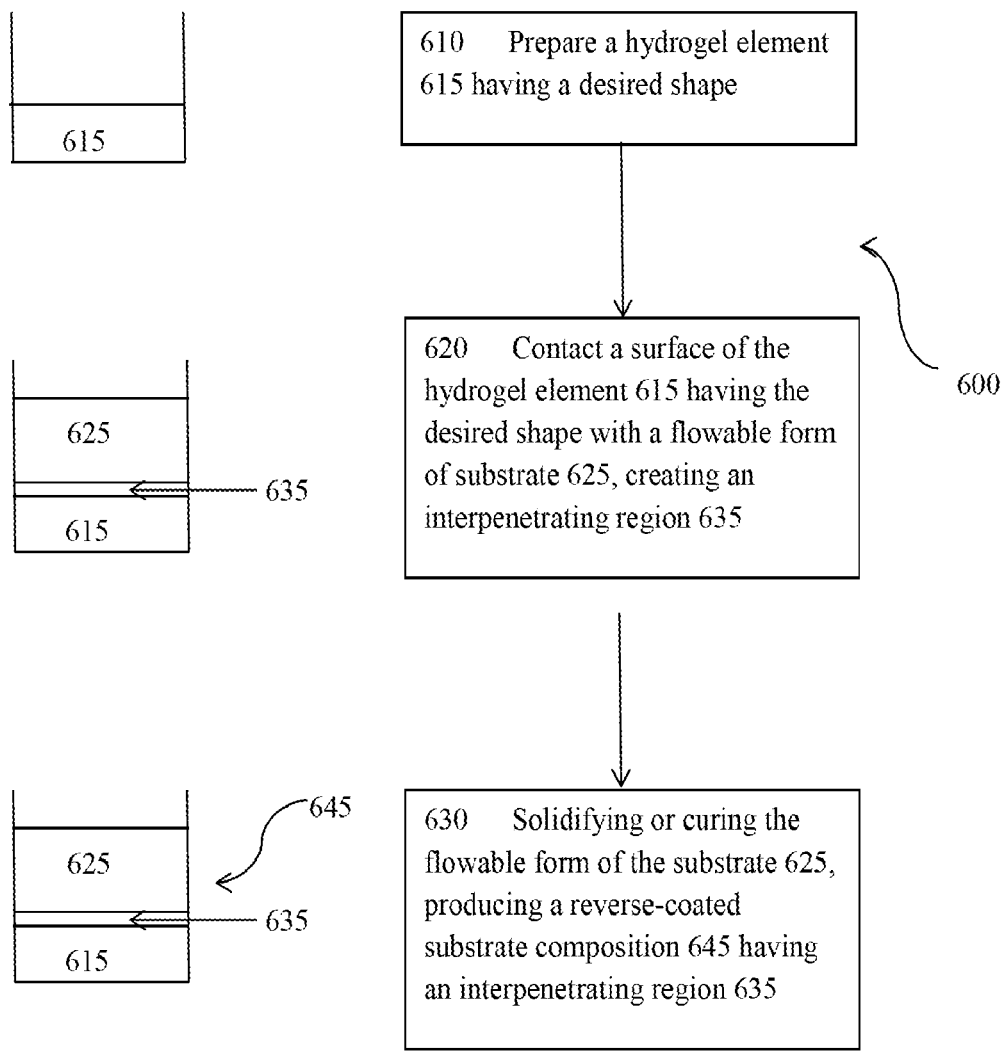
FIG. 1J is a diagram illustrating a method of reverse coating a substrate and a reverse-coated substrate.

FIG. 1H is a diagram showing a hydrogel-substrate composition in which the hydrophilic hydrogel element and the substrate are entangled such that the substrate is effectively coated with the hydrogel. FIG. 1I illustrates entanglement 575 between at least a portion of a polymer network or continuous phase of a hydrophilic hydrogel element 505 and a polymer network or continuous phase of the surface of a substrate 515.

According to aspects of the present invention, the continuous phase of the hydrophilic hydrogel element of the reverse coating composition can include one or multiple polymer chains.

According to aspects of the present invention, the continuous phase of the surface of the substrate can contain one or multiple polymer chains of polymer substrate either crosslinked or not, or gel substrate, and can contain a collection of atoms of the surface of a metal or ceramic substrate.

According to aspects of the present invention, the entanglement is physical in nature and the polymer network or the continuous phase of the hydrophilic hydrogel element and the polymer network or the continuous phase of the surface of the substrate cannot be disentangled without breaking covalent, ionic, or hydrogen bonds of either the polymer network or the continuous phase of the hydrophilic hydrogel element or the covalent, ionic, or hydrogen bonds of polymer network or the covalent, ionic, hydrogen, metallic or van der Waals bonds of continuous phase of the surface of the substrate.

According to aspects of the present invention, the resistance to the disentanglement between the hydrogel coating and the surface of the substrate is stronger than a physical absorption of the hydrogel coating onto a surface of a substrate or an immobilization of a coating through a linker that chemically binds or physically absorbs to a surface of a substrate as typically seen from current methods to obtain hydrophilic material coatings. This contributes to the durability and stability of the hydrophilic hydrogel coating on the surface of the substrates as described in this invention in a working environment such as an aqueous environment.

According to aspects of the present invention, the hydrophilic hydrogel element of a reverse coating composition has a typical thickness in the range of 1 nm-1 cm. In certain embodiments, the thickness is in the range of 1 nm-10 nm. In certain embodiments, the thickness is in the range of 1 nm-20 nm. In certain embodiments, the thickness is in the range of 1 nm-40 nm. In certain embodiments, the thickness is in the range of 1 nm-50 nm. In certain embodiments, the thickness is in the range of 10 nm-100 nm. In certain embodiments, the thickness is in the range of 50 nm-200 nm. In certain embodiments, the thickness is in the range of 50 nm-500 nm. In certain embodiments, the thickness is in the range of 100 nm-500 nm. In certain embodiments, the thickness is in the range of 100 nm-1 µm. In certain embodiments, the thickness is in the range of 500 nm-1 µm. In certain embodiments, the thickness is in the range of 500 nm-5 µm. In certain embodiments, the thickness is in the range of 1 µm-5 µm. In certain embodiments, the thickness is in the range of 1 µm-10 µm. In certain embodiments, the thickness is in the range of 1 µm-100 nm. In certain embodiments, the thickness is in the range of 1 µm-500 µm. In certain embodiments, the thickness is in the range of 100 µm-1 mm. In certain embodiments, the thickness is in the range of 500 µm-5 mm. In certain embodiments, the thickness is in the range of 1 mm-1 cm. In certain embodiments, when the hydrophilic hydrogel element plays other roles in addition to the coating function, such as being a functional part of a device, the thickness of the hydrogel can be over 1 cm.

According to aspects of the present invention, the entanglement region between the hydrophilic hydrogel element and the surface of the substrate of a reverse coating composition has a thickness less than the thickness of the hydrophilic hydrogel element and the substrate together.

According to aspects of the present invention, the entanglement region thickness is influenced by a variety of factors including the material type, stiffness, water content or other solvent condition, porosity, and thickness of hydrophilic hydrogel element, and the material type, molecular size, concentration, and viscosity of the flowable substrate, the pressure and time applied to contact the flowable substrate with the hydrophilic hydrogel element, and the curing or solidifying condition for the flowable substrate. Conditions allowing deeper penetration of the flowable substrate into the hydrophilic hydrogel element, including but not limited to high porosity of the hydrophilic hydrogel element, small molecular size and high dissolution property of the flowable substrate in the hydrophilic hydrogel element network, high pressure and long time applied to contact the flowable substrate with the hydrophilic hydrogel element, result in a higher thickness of the entanglement region.

According to aspects of the present invention, the entanglement region between the hydrophilic hydrogel element and the surface of the substrate of a reverse coating composition is preferred to be obtained through the reverse coating method where the hydrophilic hydrogel element with higher porosity forms first and the substrate with lower porosity forms later. In certain embodiments, the entanglement region between the hydrophilic hydrogel element and the surface of the substrate of a reverse coating composition can only be formed using the reverse coating method particularly when the substrate has no porosity or limited porosity. In certain embodiments, the entanglement region between the hydrophilic hydrogel element and the surface of the substrate of a reverse coating composition is preferred to be formed using the reverse coating method so as to form more stabilized or higher level entanglement when the porosity of the substrate is lower than the porosity of the hydrophilic hydrogel element, compared with an entanglement formed in a regular coating method where the substrate forms first and the hydrophilic hydrogel element forms later.

According to aspects of the present invention, the hydrophilic hydrogel element of a reverse coating composition comprises one or more of crosslinked poly-acrylic acid, crosslinked poly(vinyl alcohol), non-crosslinked poly(vinyl alcohol), crosslinked poly(vinylpyrrolidone), non-crosslinked poly(vinylpyrrolidone), crosslinked polyacrylamide, crosslinked poly-(N-isopropyl-acrylamide) (PNIPAAm), non-crosslinked poly-(N-isopropyl-acrylamide), crosslinked poly-methyl-methacrylate, crosslinked polyethylene glycol (PEG), crosslinked poly(ethylene glycol) methacrylate (PEGMA), crosslinked poly(ethylene glycol) diacrylate (PEGDA), crosslinked polypropylene glycol, crosslinked zwitterionic poly-(sulfobetaine methacrylate) (PSBMA), crosslinked zwitterionic 2-methacryloyloxyethyl phosphorylcholine (PMPC), crosslinked zwitterionic poly-carboxybetaine methacrylate (PCBMA), crosslinked zwitterionic poly-carboxybetaine acrylamide (PCBAA), non-crosslinked zwitterionic PCBAA, crosslinked alginate, crosslinked chitosan, gelatin, collagen, fibrin, agarose, hyaluronic acid, cellulose, polypeptides, or a derivative of one or more of the foregoing.

In certain embodiments, the hydrophilic hydrogel element of a reverse coating composition of the present invention includes a zwitterionic polymer based hydrogel.

In certain embodiments, the hydrogel coating comprises PEG based hydrogels.

In certain embodiments, the hydrophilic hydrogel element of a reverse coating composition of the present invention includes a PNIPAAm based hydrogel.

In certain embodiments, the hydrophilic hydrogel element of a reverse coating composition of the present invention includes a chitosan based hydrogel.

According to aspects of the present invention, the surface of the substrate of a reverse coating composition includes agarose, crosslinked alginate, crosslinked or non-crosslinked poly-hydroxyethyl-methacrylate (PHEMA), crosslinked or non-crosslinked poly-N-(2-Hydroxypropyl) methacrylamide (PHPMA), polydimethylsiloxane (PDMS), crosslinked or non-crosslinked polystyrene (PS), crosslinked silicone hydrogel, polyurethane (PU), silicone rubber, epoxy, epoxy-coated steel, glass, ceramic, plastic, metal, membrane materials, a derivative of any of the foregoing or a combination of any two or more of the foregoing.

According to aspects of the present invention, the surface of the substrate of a reverse coating composition includes one or more additional components selected from the hydrogel coating compositions, which is or is not used as the hydrogel coating composition in a particular reverse coating composition.

According to aspects of the present invention, a membrane material includes porous structures made from organic and/or inorganic materials.

According to aspects of the present invention, a membrane material includes porous structures made from organic and/or inorganic materials. Depending on average pore sizes, the membranes can be used for processes including reverse osmosis, nanofiltration, ultrafiltration, membrane distillation, microfiltration, etc. Common materials for membrane fabrication include cellulose acetate/triacetate, aromatic polyamide, polypiperzine, polybenziimidazoline, polyamides, polysulfones, polyols, polyphenols, polyacrylonitrile, polyethersulfone, polysulfone, poly(phthazine ether sulfone ketone), poly(vinyl butyral), polyvinylidene fluoride, poly(tetrafluorethylene), polypropylene, polyethylene, polyetheretherketone, poly(trimesoyl chloride-co-piperazine), poly(trimesoyl chloride-co-m-phenylenediamine), poly(trimesoyl chloride-co-p-phenylenediamine), poly(trimesoyl chloride-co-triethylenetetramine), poly(trimesoyl chloride-co-N—N'-diaminopiperazine), poly(trimesoyl chloride-co-N-(2-aminoethyl)-piperazine), poly(trimesoyl chloride-co-polyethyleneimine), poly(iso-phthaloyl dichloride-co-piperazine), poly(iso-phthaloyl dichloride-co-m-phenylenediamine), poly(iso-phthaloyl dichloride-co-p-phenylenediamine), poly(iso-phthaloyl dichloride-co-triethylenetetramine), poly(iso-phthaloyl dichloride-co-N—N'-diaminopiperazine), poly(iso-phthaloyl dichloride-co-N-(2-aminoethyl)-piperazine), poly(iso-phthaloyl dichloride-co-polyethyleneimine), etc.

According to aspects of the present invention, the surface of the substrate of a reverse coating composition is or includes agarose.

According to aspects of the present invention, the surface of the substrate of a reverse coating composition is or includes alginate.

According to aspects of the present invention, the surface of the substrate of a reverse coating composition is or includes PHEMA.

According to aspects of the present invention, the surface of the substrate of a reverse coating composition is or includes PDMS.

According to aspects of the present invention, the surface of the substrate of a reverse coating composition is or includes PS.

According to aspects of the present invention, the surface of the substrate of a reverse coating composition is or includes a silicone hydrogel.

According to aspects of the present invention, the surface of the substrate of a reverse coating composition is or includes a membrane material.

Various aspects of the invention relate to reverse coating methods for making a reverse coating composition. A reverse coating method can include firstly forming and fixing a hydrogel coating in a desired shape. The hydrogel may be any hydrogel coating described herein. A reverse coating method can include secondly contacting the hydrogel coating with a flowable and curable or solidifiable substrate. Contacting a hydrogel coating with a flowable substrate may result in at least a portion of the flowable substrate entering the hydrogel. A reverse coating method can include thirdly curing or solidifying the substrate.

Forming and fixing a hydrogel coating in a desired shape can include forming the hydrogel on a surface or in a mold. For example, a hydrogel may be formed on a polymer surface (e.g., a polypropylene surface) thereby fixing the hydrogel in a desired shape (e.g., a flat shape).

A flowable substrate can be a liquid, suspension, colloid, or powder. The flowable character of the substrate enables the contacting surface of the substrate to penetrate into the polymer network of the hydrogel coating. The flowable substrate may comprise or consist of plastics, ceramics, metals, or small molecules, or macro molecules capable of polymerization or crosslinking.

The flowable substrate can be cured or solidified, for example, by heating or cooling the substrate, drying the substrate, evaporating solvent, or irradiating the substrate with microwave, infrared, visible, or ultraviolet radiation. A reverse coating method can include curing or solidifying the substrate for at least about 0.5, 1, 5, 10, 15, 20, 25, 30, 45, 60 minutes or at least about 1, 2, 6, or 12 hours.

After curing or solidification, the flowable contacting surface of the substrate that penetrated into the polymer network of the hydrogel coating was transformed to a polymer network or a continuous phase that was physically entangled with the polymer network of the hydrogel coating.

Provided according to aspects of the present disclosure is a reverse coating composition 1 and a method to produce it, comprising a zwitterionic PCBAA hydrogel coating and a PHEMA substrate.

Provided according to aspects of the present disclosure is a reverse coating composition 2 and a method to produce it, comprising a zwitterionic PCBAA hydrogel coating and an alginate substrate.

Provided according to aspects of the present disclosure is a reverse coating composition 3 and a method to produce it, comprising a zwitterionic PCBAA hydrogel coating and a PDMS substrate.

Provided according to aspects of the present disclosure is a reverse coating composition 4 and a method to produce it, comprising a zwitterionic PCBAA hydrogel coating and a silicone hydrogel (contact lens) substrate.

Provided according to aspects of the present disclosure is a reverse coating composition 5 and a method to produce it, comprising a zwitterionic PCBAA hydrogel coating and an agarose substrate.

Provided according to aspects of the present disclosure is a reverse coating composition 6 and a method to produce it, comprising a zwitterionic PCBMA hydrogel coating and a PHEMA substrate.

Provided according to aspects of the present disclosure is a reverse coating composition 7 and a method to produce it, comprising a zwitterionic PSBMA hydrogel coating and a PHEMA substrate.

Provided according to aspects of the present disclosure is a reverse coating composition 8 and a method to produce it, comprising a zwitterionic PMPC hydrogel coating and a PHEMA substrate.

Provided according to aspects of the present disclosure is a reverse coating composition 9 and a method to produce it, comprising a PEG hydrogel coating and a PHEMA substrate.

Provided according to aspects of the present disclosure is a reverse coating composition 10 and a method to produce it, comprising a PEG hydrogel coating and a PDMS substrate.

Provided according to aspects of the present disclosure is a reverse coating composition 11 and a method to produce it, comprising a PEG hydrogel coating and a PS substrate.

Provided according to aspects of the present disclosure is a reverse coating composition 12 and a method to produce it, comprising a PNIPAAm hydrogel coating and a PHEMA substrate.

Provided according to aspects of the present disclosure is a reverse coating composition 13 and a method to produce it, comprising a PNIPAAm hydrogel coating and a PS substrate.

Provided according to aspects of the present disclosure is a reverse coating composition 14 and a method to produce it, comprising a chitosan hydrogel coating and a PHEMA substrate.

Provided according to aspects of the present disclosure is a reverse coating composition 15 and a method to produce it, comprising a PHEMA tubing substrate with inner wall coated with zwitterionic PCBAA hydrogel coating.

Provided according to aspects of the present disclosure is a reverse coating composition 16 and a method to produce it, comprising a PHEMA tubing substrate with inner wall coated with PEG hydrogel coating.

Provided according to aspects of the present disclosure is a reverse coating composition 17 and a method to produce it, comprising a PHEMA tubing substrate with outer wall coated with zwitterionic PCBAA hydrogel coating.

Provided according to aspects of the present disclosure is a reverse coating composition 18 and a method to produce it, comprising a PHEMA tubing substrate with outer wall coated with PEG hydrogel coating.

Provided according to aspects of the present disclosure is a reverse coating composition 19 and a method to produce it, comprising a PHEMA tubing substrate with both inner and outer wall coated with zwitterionic PCBAA hydrogel coating.

Provided according to aspects of the present disclosure is a reverse coating composition 20 and a method to produce it, comprising a PHEMA tubing substrate with both inner and outer wall coated with PEG hydrogel coating.

Provided according to aspects of the present disclosure are reverse coating compositions and methods to produce them, comprising a PHEMA tubing substrate with inner and/or outer wall coated with hydrophilic hydrogel coating including PCBMA, PSBMA, PMPC, PNIPAAm, chitosan, etc.

Provided according to aspects of the present disclosure are reverse coating compositions and methods to produce them, comprising an alginate tubing substrate with inner and/or outer wall coated with hydrophilic hydrogel coating including PCBAA, PCBMA, PSBMA, PMPC, PEG, PNIPAAm, chitosan, etc.

Provided according to aspects of the present disclosure are reverse coating compositions and methods to produce them, comprising an agarose tubing substrate with inner and/or outer wall coated with hydrophilic hydrogel coating including PCBAA, PCBMA, PSBMA, PMPC, PEG, PNIPAAm, chitosan, etc.

Provided according to aspects of the present disclosure are reverse coating compositions and methods to produce them, comprising a PDMS tubing substrate with inner and/or outer wall coated with hydrophilic hydrogel coating including PCBAA, PCBMA, PSBMA, PMPC, PEG, PNIPAAm, chitosan, etc.

Provided according to aspects of the present disclosure are reverse coating compositions and methods to produce them, comprising a silicone hydrogel tubing substrate with inner and/or outer wall coated with hydrophilic hydrogel coating including PCBAA, PCBMA, PSBMA, PMPC, PEG, PNIPAAm, chitosan, etc.

Provided according to aspects of the present disclosure are reverse coating compositions and methods to produce them, comprising a PS tubing substrate with inner and/or outer wall coated with hydrophilic hydrogel coating including PCBAA, PCBMA, PSBMA, PMPC, PEG, PNIPAAm, chitosan, etc.

Provided according to aspects of the present disclosure is a reverse coating composition 21 and a method to produce it, comprising a zwitterionic PCBAA hydrogel coating and a poly(trimesoyl chloride-co-piperazine) membrane substrate.

Provided according to aspects of the present disclosure is a reverse coating composition 22 and a method to produce it, comprising a zwitterionic PCBAA hydrogel coating and a poly(trimesoyl chloride-co-m-phenylenediamine) membrane substrate.

Provided according to aspects of the present disclosure is a reverse coating composition 23 and a method to produce it, comprising a zwitterionic PCBAA hydrogel coating and a poly(iso-phthaloyl dichloride-co-triethylenetetramine) membrane substrate.

Provided according to aspects of the present disclosure are reverse coating compositions and methods to produce them, comprising a membrane substrate including poly(trimesoyl chloride-co-piperazine), poly(trimesoyl chloride-co-m-phenylenediamine), poly(trimesoyl chloride-co-p-phenylenediamine), poly(trimesoyl chloride-co-triethylenetetramine), poly(trimesoyl chloride-co-N—N'-diaminopiperazine), poly(trimesoyl chloride-co-N-(2-aminoethyl)-piperazine), poly(trimesoyl chloride-co-polyethyleneimine), poly(iso-phthaloyl dichloride-co-piperazine), poly(iso-phthaloyl dichloride-co-m-phenylenediamine), poly(iso-phthaloyl dichloride-co-p-phenylenediamine), poly(iso-phthaloyl dichloride-co-triethylenetetramine), poly(iso-phthaloyl dichloride-co-N—N'-diaminopiperazine), poly(iso-phthaloyl dichloride-co-N-(2-aminoethyl)-piperazine), poly(iso-phthaloyl dichloride-co-polyethyleneimine), etc., and hydrophilic hydrogel coating including PCBAA, PCBMA, PSBMA, PMPC, PEG, PNIPAAm, chitosan, etc.

Provided according to aspects of the present disclosure is a tubing substrate with inner wall, outer wall, or both inner and outer walls coated with the hydrogel reverse coatings using the reverse coating method.

The substrate and the hydrogel coating can be any of the various materials as described herein. The obtained hydrogel reverse coating on substrates, including the tubing materials can be used for various blood or tissue contacting applications, including artificial blood vessels, catheters, infusion and dialysis devices.

EXAMPLES

No currently-available coating technology can prevent biofilm formation. The instant application describes a solution to fully address this tough issue by developing a super-antifouling coating. A zwitterionic hydrogel was combined with commercial superglue containing cyanoacrylates to create a Durable and Ultra-Robust Antifouling Zwitterionic coating (Coating composition 1) that can be easily and universally applied to common substrates. Commercial hydrophobic superglue was used to strongly immobilize the super-hydrophilic Coating composition 1 through interpenetration. Coating composition 1 and the corresponding binding composition 1 effectively solves several key challenges preventing the current antifouling coatings from practical use, including difficult fabrication, low efficacy, poor toughness, and durability. The fabricated coating (binding composition 1) retained anti-fouling properties after 90 days of immersion in water, 50 days of buffer shearing, 30 days of water-flushing, and after repeated knife-scratch and sandpaper abrasion under 570 kPa. The fabricated coating (binding composition 1) achieved a rarely reported long-term biofilm resistance to both Gram-positive and Gram-negative bacteria and fungi: it displayed negligible microbe adhesion after continuous challenge with more than $10^9$ cells per mL culture medium for 30 days. In comparison, state-of-the-art antifouling coatings started to have bacteria attachment after immediate contact and were covered with dense biofilm typically within ~7 days.

Super-hydrophilic zwitterionic polymer materials are known for their superior antifouling properties. But they, like common hydrophilic coatings, drastically tend to dissolve in the aqueous environment resulting in poor coating durability. The vulnerability to mechanical damage further prevents these hydrophilic coatings from being practically applied. Superglue based on ethyl cyanoacrylate is one of the strongest linkages ever known for daily bonding projects, but it is known to only glue hydrophobic materials such as metal, plastic, or wood. It cannot stably bind to hydrophilic surfaces, e.g., glass slides, which have a water contact angle of ~28°.

This disclosure describes the immobilization of super-hydrophilic zwitterionic hydrogels (water contact angle <2°) with hydrophobic superglue through a unique interpenetration mechanism. (The mechanisms disclosed herein should not limit the scope of the disclosure or claims.) The obtained coating (binding composition 1) was super-hydrophilic and retained anti-fouling properties after various long-term durability tests in aqueous environments by incubating (90 days), shearing (50 days) and flushing (30 days), as well as mechanical damage tests by knife-scratch and repeated sandpaper abrasion at 570 kPa. The pressure used in the abrasion test was more than 150 times higher than other similar tests for coating stability. Remarkably, the obtained coating (binding composition 1) was able to achieve almost zero bacteria adhesion for at least one month when continuously incubated with highly concentrated bacteria or fungi (>$10^9$ cells per mL) in culture media under both dynamic and static conditions. This remarkable anti-biofilm performance has rarely been achieved. The hydrogel coating in binding composition 1 can be easily removed from the substrate and re-applied, which further extends the applicability of this coating strategy.

According to aspects of the present invention, the formation of the binding composition 1 involves the combined use of a fabricated coating composition 1 and commercially-available superglue. In one example, coating composition 1 was prepared by the in-situ growing of a thin layer of zwitterionic poly-carboxybetaine acrylamide (PCBAA, 3-((3-acrylamidopropyl)dimethylammonio)propanoate) hydrogel on a commercially available polypropylene liner (FIG. 1A). The fabricated coating composition 1 (hydrogel tape) was mechanically stronger than the pure zwitterionic PCBAA hydrogel and could withstand pulling, bending, wrenching, and rolling up (FIG. 1B). These properties ensure ease of storage, transport, and mounting of the coating composition 1 on substrates to be coated. The fabricated coating composition 1 can be directly mounted as a coating layer without further treatment.

The coating composition 1 can be glued on a variety of substrates through a simple procedure (FIG. 1C). As an example, a substrate was firstly cleaned, e.g., the polyurethane (PU) substrate was rinsed with alcohol and dried in air. Then cyanoacrylate superglue was applied onto the dried substrate followed by pressing the coating composition 1 (hydrogel layer facing down) onto the superglue for a few seconds (100 µL superglue could cover ~0.8 cm² surface area). One hour was allowed to completely solidify the superglue. The liner on top of the hydrogel was removed, and the glued coating was transferred to DI water for equilibration. 20 minutes later, the bound hydrogel coating was polished either by a small shovel or tweezer, leaving the surface of the substrate with a thin layer of coating.

Figure 6:
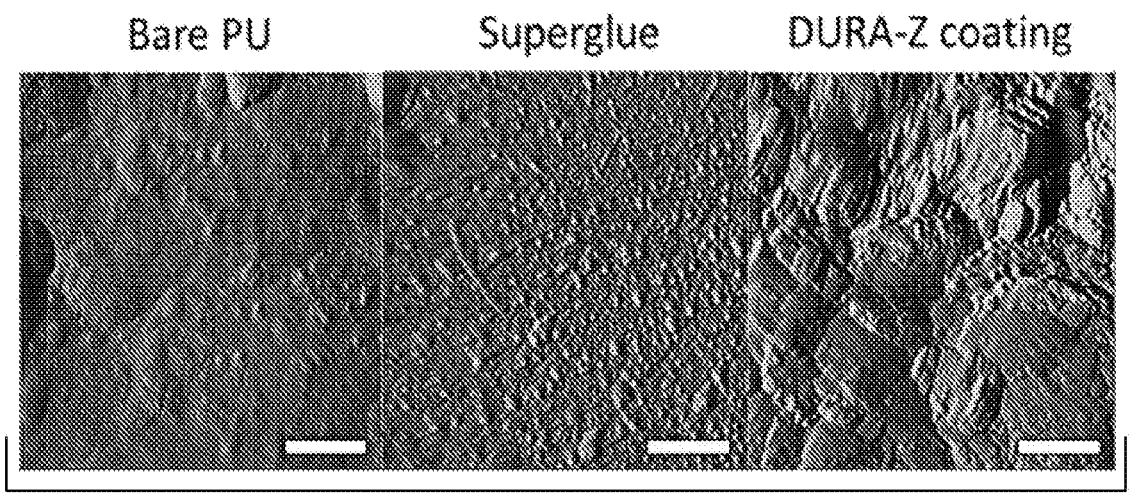
FIG. 6 shows AFM images of bare PU substrate, superglue and zwitterionic PCBAA hydrogel (called DURA-Z coating in FIG. 6) coated PU substrates (binding composition 1). Scale bar=50 μm.

The resulting coating (binding composition 1) showed completely different morphology compared to the polyurethane substrate or a cyanoacrylate superglue surface by Scanning Electron Microscopy (SEM, FIG. 2A) and Atomic-force Microscopy (AFM, FIG. 6). SEM images of coating cross-sections provided structural details of a surface hydrogel layer and a hydrogel/glue interpenetrating layer (FIG. 2A). The overall thickness of the coating (two layers) was measured to be 324±13 µm. The thickness of the interpenetrating layer (187±27 µm) did not change much with varied fabrication parameters. Applying different volumes of superglue did not induce changes in the interpenetrating thickness since an excessive amount of superglue would be squeezed out of the edge of the coating composition 1. Applying higher compressive pressure to bind the coating composition 1 to the substrate such as from ~25 Pa to ~6000 Pa only resulted in a minor increase of interpenetrating thickness from 187±27 µm to 196±23 µm. The surface of the obtained coating (binding composition 1) was characterized by infrared (IR) spectroscopy and showed almost the same chemical composition as a pure zwitterionic PCBAA hydrogel (FIG. 2C). This implied that the surface of the binding composition 1 would display anti-fouling properties as good as a zwitterionic hydrogel. The water contact angle (FIG. 2B) indicated that the coating (binding composition 1) was super-hydrophilic with great wettability similar to a pure PCBAA hydrogel surface.

Super-hydrophilic polymer coatings are known to be unstable since polymers tend to dissolve in water. Common hydrophilic coatings would fail within a few weeks in an aqueous environment. The coating in binding composition 1 did not deteriorate when incubated in deionized water at room temperature for up to three months. The morphology of the coating was almost unchanged, and anti-fouling properties (tested by human fibrinogen binding followed by ELISA quantification of the absorbed protein) were retained at the same level as freshly-made coatings after the long-term incubation (FIG. 7A). The coating in binding composition 1 was further examined under various durability tests in aqueous environments including (1) phosphate buffered saline (PBS) shearing (1500 rpm, 202 G) at room temperature for 50 days (FIG. 7B), (2) PBS shearing (1500 rpm, 202 G) at body temperature (37° C.) for 30 days (FIG. 3A), and (3) continuous perpendicular water-flush at a flow rate of 42.8 ml/s for 30 days (FIG. 3B). These challenging conditions did not change the morphology of the coating in binding composition 1, and the antifouling property of the coating was well-retained, as assessed by the unchanged, significantly lowered human fibrinogen absorption on the coating compared with uncoated polyurethane (FIGS. 3A & 3B).

In the working environment, anti-fouling coatings potentially experience cycled dry/wet challenges. Many hydrophilic coatings can hardly retain anti-fouling function after being dried out and rehydrated. The coating in binding composition 1 was challenged by dry/wet cycles under air flow and water and showed complete re-hydration (FIG.

Figure 8A:
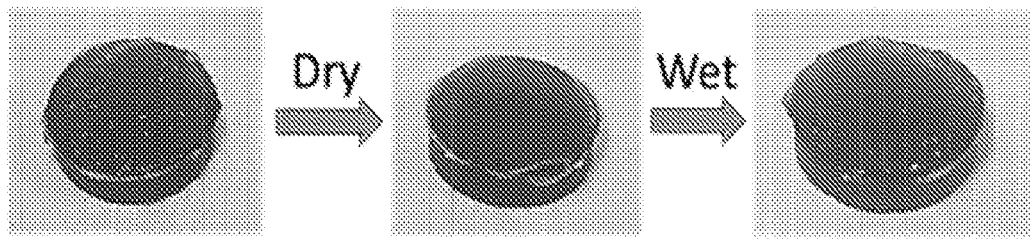
FIG. 8A illustrates a dry/wet cycle challenge on zwitterionic PCBAA hydrogel coating on PU disk substrate (binding composition 1), the coating was completely dried under air flow for 1 h and then placed in water to re-hydrate.
Figure 8B:
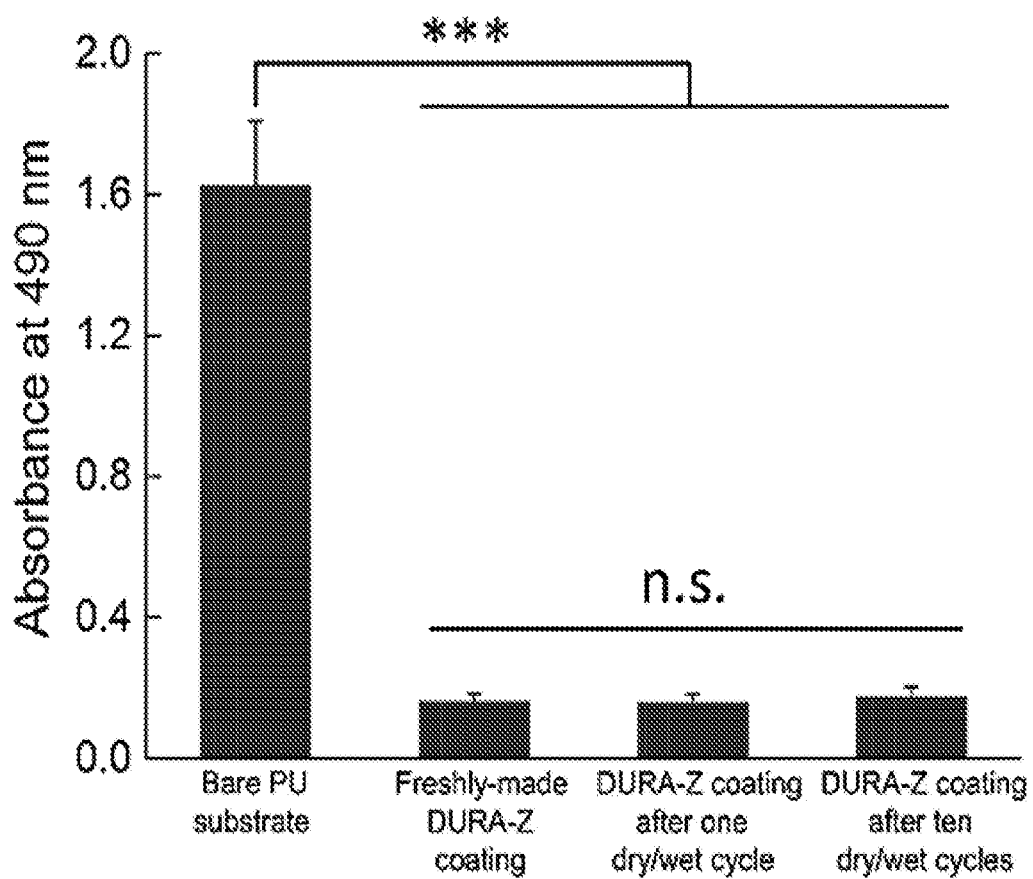
FIG. 8B shows anti-fouling property of zwitterionic PCBAA hydrogel coating in binding composition 1 (called DURA-Z coating in FIG. 8B) after dry/wet cycles. All data are presented as mean of replicates (n=3)±standard deviation. Statistical analysis: one-way ANOVA with Bonferroni multi-comparison. ***: p<0.0001. n.s.: no significant difference, p>0.5
Figure 10A:
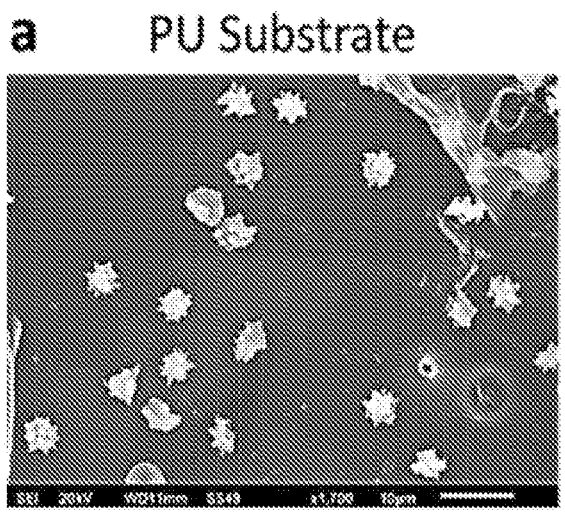
FIGS. 10A, 10B, and 10C show platelet adhesion after platelet rich plasma challenge on PU substrate, superglue surface and zwitterionic PCBAA hydrogel coating (called DURA-Z coating in FIGS. 10C and 10D) in binding composition 1, respectively.
Figure 10B:
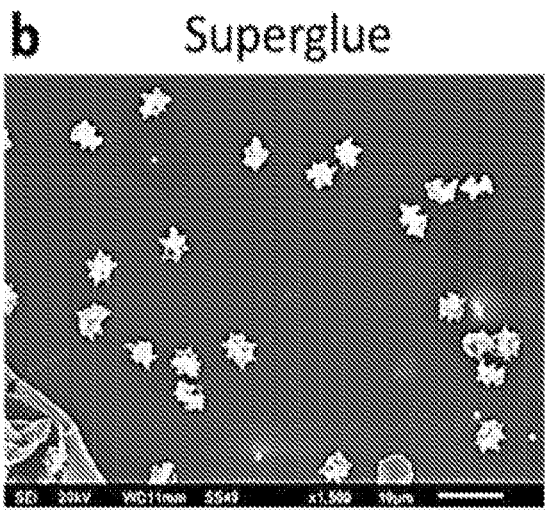
Figure 10C:
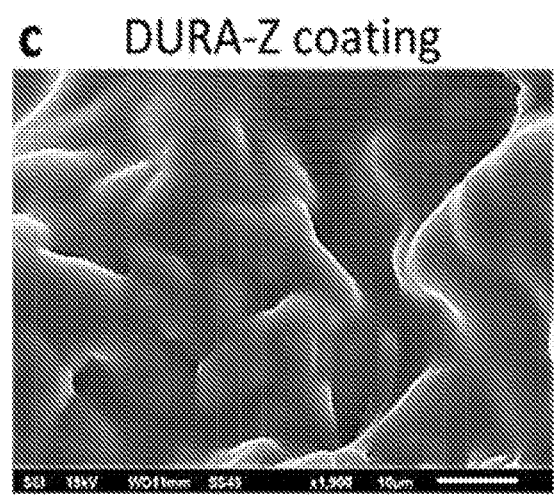
Figure 10D:
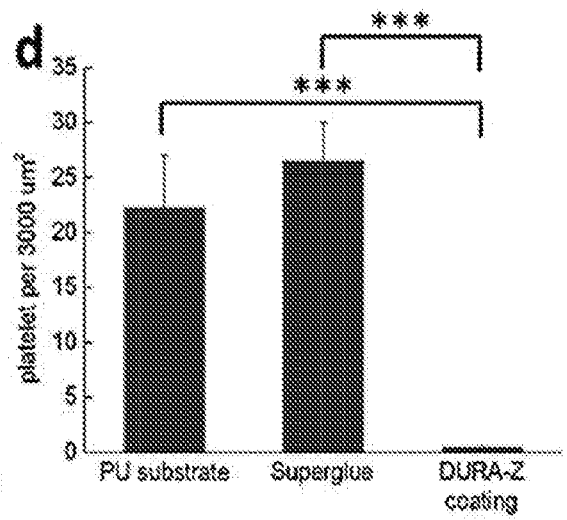
FIG. 10D is a graph showing calculated platelet density on the different surfaces. Data are presented as mean of replicates (n=3)±standard deviation. Statistical analysis: one-way ANOVA with Bonferroni multi-comparison. ***: p<0.0001.
Figure 11:
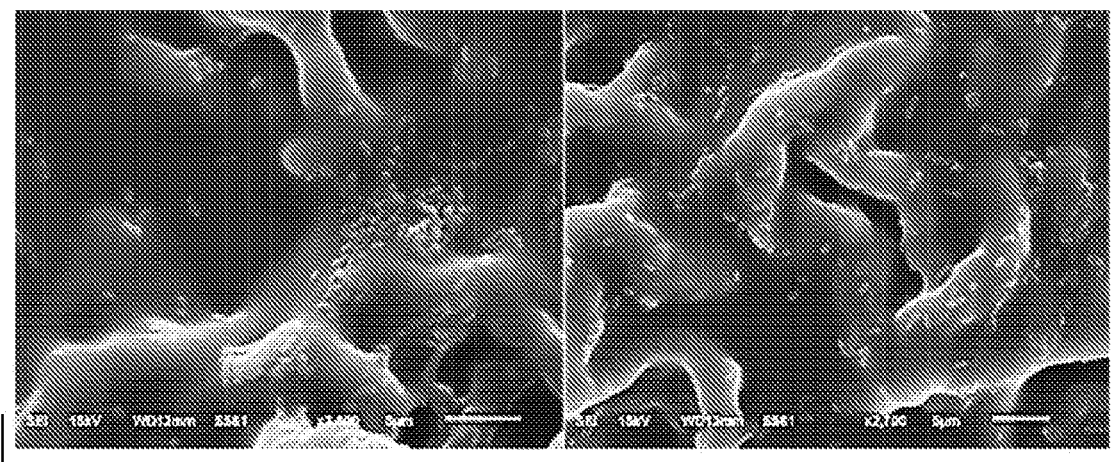
FIG. 11 shows representative SEM images showing bacteria adhesion on zwitterionic PCBAA hydrogel coating after 30 days of culture with bacteria at static condition without any rinsing. Scale bar=5 μm.

8A), and the anti-fouling property was well-preserved even after 10 dry/wet cycles (FIG. 8B).

Figure 3C:
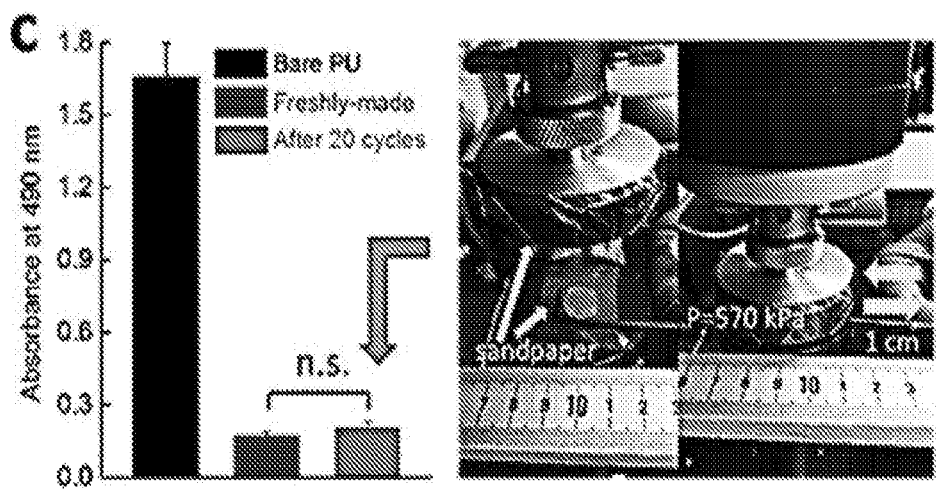
Figure 3D:
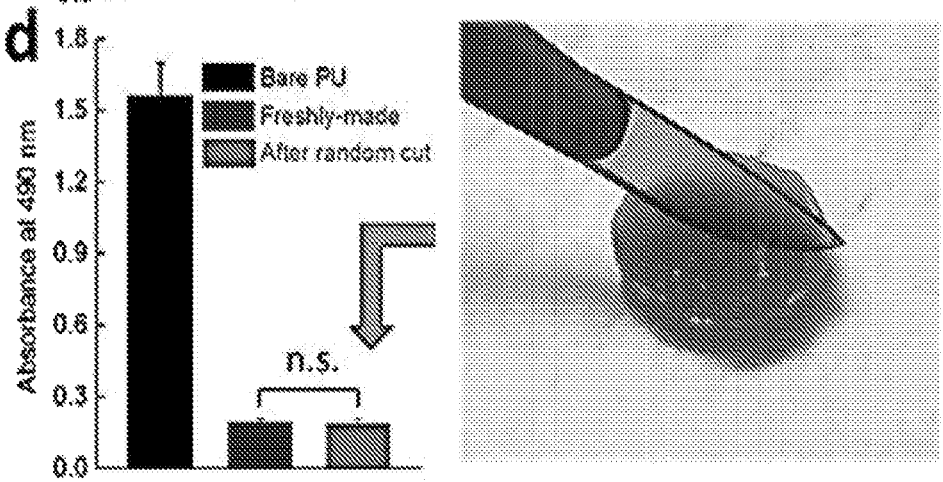

The coating in binding composition 1 was further subjected to mechanical damage tests including a sharp scalpel to randomly scratch the coating (FIG. 3D). The coating retained its small water contact angle and its excellent anti-fouling properties (FIG. 3D). The resistance to sharp scratches was attributed to the self-healing capability of PCBAA hydrogels. Even with a deep incision when the coating layer in the binding composition 1 was completely cut through and a permanent scratch was left on the substrate (blade thickness: 20-30 µm), the damaged coating layer in the binding composition 1 was able to heal together in an aqueous environment (FIGS. 9A & 9B) and retain anti-fouling capability.

The coating in binding composition 1 was further tested in an abrasion test, where a polyurethane disk substrate with both sides coated with coating composition 1 was placed between two stationary pieces of sandpaper (400 grit), and a pressure of 570 kPa was applied by a compressor (FIG. 3C). The disk was moved back and forth (displacement=1 cm) for 20 cycles, and the coating survived this abrasion test with great water wettability and unchanged anti-fouling properties (FIG. 3C). (The 570 kPa pressure used in the abrasion test is more than 150 times higher than other similar tests for coating stability.) In the sandpaper abrasion test, a polyurethane disk substrate without the coating failed at 50 kPa. The resistance to mechanical abrasion damage was attributed to the slippery surface property (low friction) of the coating in binding composition 1. Applying the coating reduced the friction index between the polyurethane disk substrate and sand paper by more than 53% (FIGS. 9C & 9D).

In biomedical applications in which surfaces are exposed to complex media such as blood, the coating was probed against platelet adhesion and activation, which induces thrombosis and blood clotting. The coating in binding composition 1 was incubated in platelet rich plasma at 37° C. overnight and platelet adhesion was visualized by SEM. The results indicated that the coating in binding composition 1 could effectively resist the adhesion of platelets (nearly "0" adhesion) in platelet rich plasma, compare to a bare polyurethane surface or a superglue-coated surface (FIG. 10).

Microorganism attachment on surfaces leads to biofilm formation that causes medical device failure, infection, and marine-fouling. Hydrophilic polymer coatings, such as zwitterionic polymers, are non-toxic and environmentally friendly and have shown their effectiveness in resisting microorganism adhesion. Nevertheless, due to the instability of hydrophilic polymers in an aqueous environment, prior art coatings were not able to maintain the resistance to microorganism adhesion for a longer period of time such as a few days. The ultra-durable and robust coating in binding composition 1, however, can greatly improve long-term microorganism resistance performance.

Figures 4C, 4D:
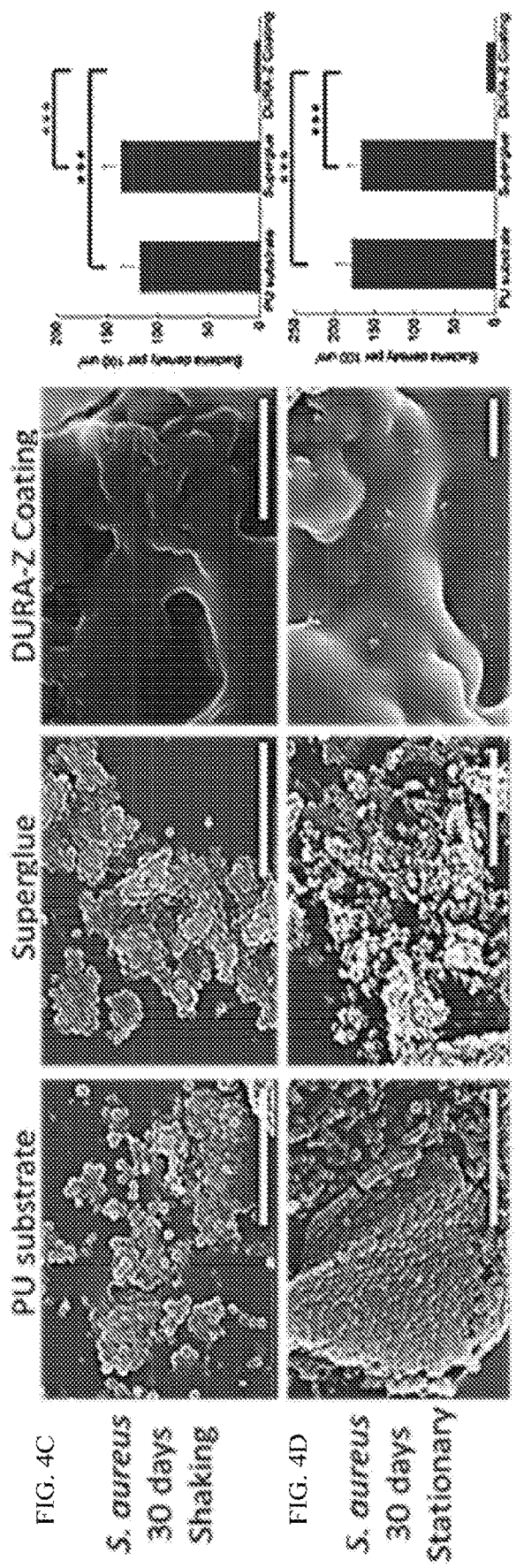

The coating in binding composition 1 was incubated in the presence of *Escherichia coli* to study the coating's resistance to biofilm formation, and bacterial adhesion was quantified by SEM. Zwitterionic hydrogel coated polyurethane substrates (binding composition 1) were placed in bacterial culture medium (Luria-Bertani Broth) containing a high number of bacteria ($1.05 \times 10^9$ cells per mL) at 37° C. for 30 days under continuous shaking (300 rpm). The culture medium was gently refreshed every two days, and the bacterial density within the refreshed medium was held at $1.05 \times 10^9$ cells per mL. After 30 days, bacteria on the substrate surface were fixed, dehydrated, vacuumed, and visualized under SEM. Results indicate almost zero adhesion of bacteria on the zwitterionic coating in binding composition 1, whereas a biofilm had developed on the bare polyurethane substrate and the superglue-coated surface controls (FIG. 4A).

The coating in binding composition 1 was further-challenged with a stationary culture of high-density bacteria ($1.05 \times 10^9$ cells per mL) in LB broth at 37° C., and the bacteria were allowed to settle on the substrate surface by gravity. The culture medium was gently refreshed day-by-day, and the bacterial density within the refreshed medium was maintained at $1.05 \times 10^9$ cells per mL. After 30 days, without any rinsing, only a small amount of bacteria was found to be scattered on the coating in binding composition 1 (no biofilm forming) under SEM (FIG. 10). With 30 min of rinsing in PBS, these scattered bacteria were easily washed off from the coating in binding composition 1 (FIG. 4B). By contrast, a biofilm (high-density bacteria adhered) formed on the bare polyurethane substrate and superglue coated-substrate controls, and remained to be firmly attached even after rinsing (FIG. 4B).

In addition to the Gram-negative *E. coli* bacterium, the anti-biofilm capability of the coating in binding composition 1 was tested against Gram-positive bacterium (*Staphylococcus aureus*) and fungus (*Candida albicans*). Similar challenge conditions ($1.05 \times 10^9$ cells per mL) were applied with *S. aureus* and *C. albicans* on the coating using both shaking and stationary methods for up to 30 days. Results indicated that the coating in binding composition 1 has strong resistance to the adhesion of both *S. aureus* (FIGS. 4C & 4D) and *C. albicans* (FIGS. 4E & 4F) after the long-term culture while uncoated control surfaces displayed thick biofilms.

Figure 12A:
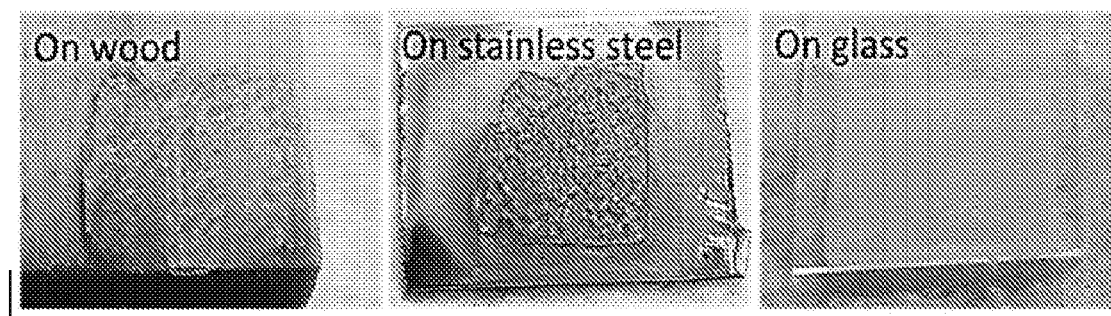
FIG. 12A shows images of Zwitterionic PCBAA hydrogel coating on wood, stainless steel, and glass substrates (binding composition 1).
Figure 13:
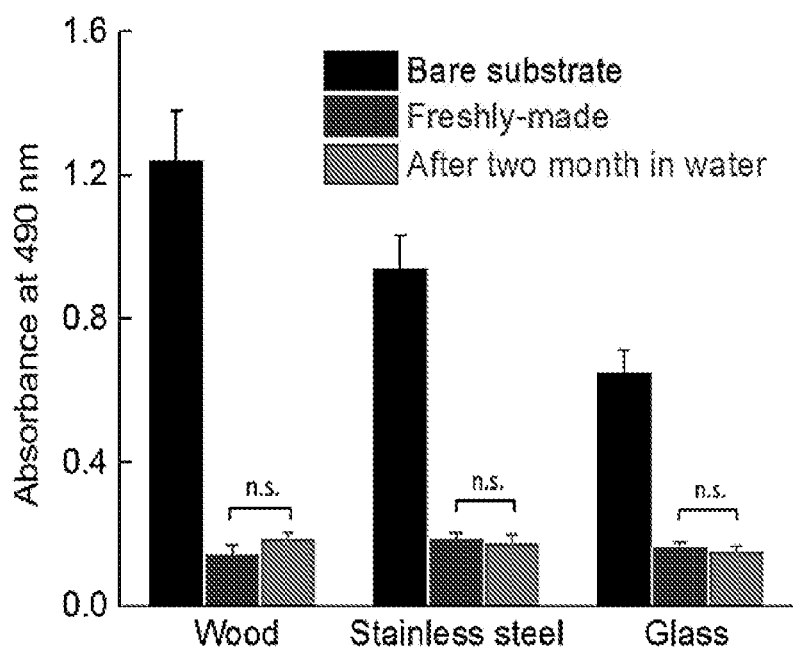
FIG. 13 is a graph showing antifouling property of zwitterionic PCBAA hydrogel coating on wood, stainless steel and glass substrates (binding composition 1) after two-month incubation in water. All data are presented as mean of replicates (n=3)±standard deviation. Statistical analysis: unpaired, two-tailed t-test, n.s.: no significant difference at P>0.05, meaning the great anti-fouling property was retained.
Figures 14A, 14B, 14C:
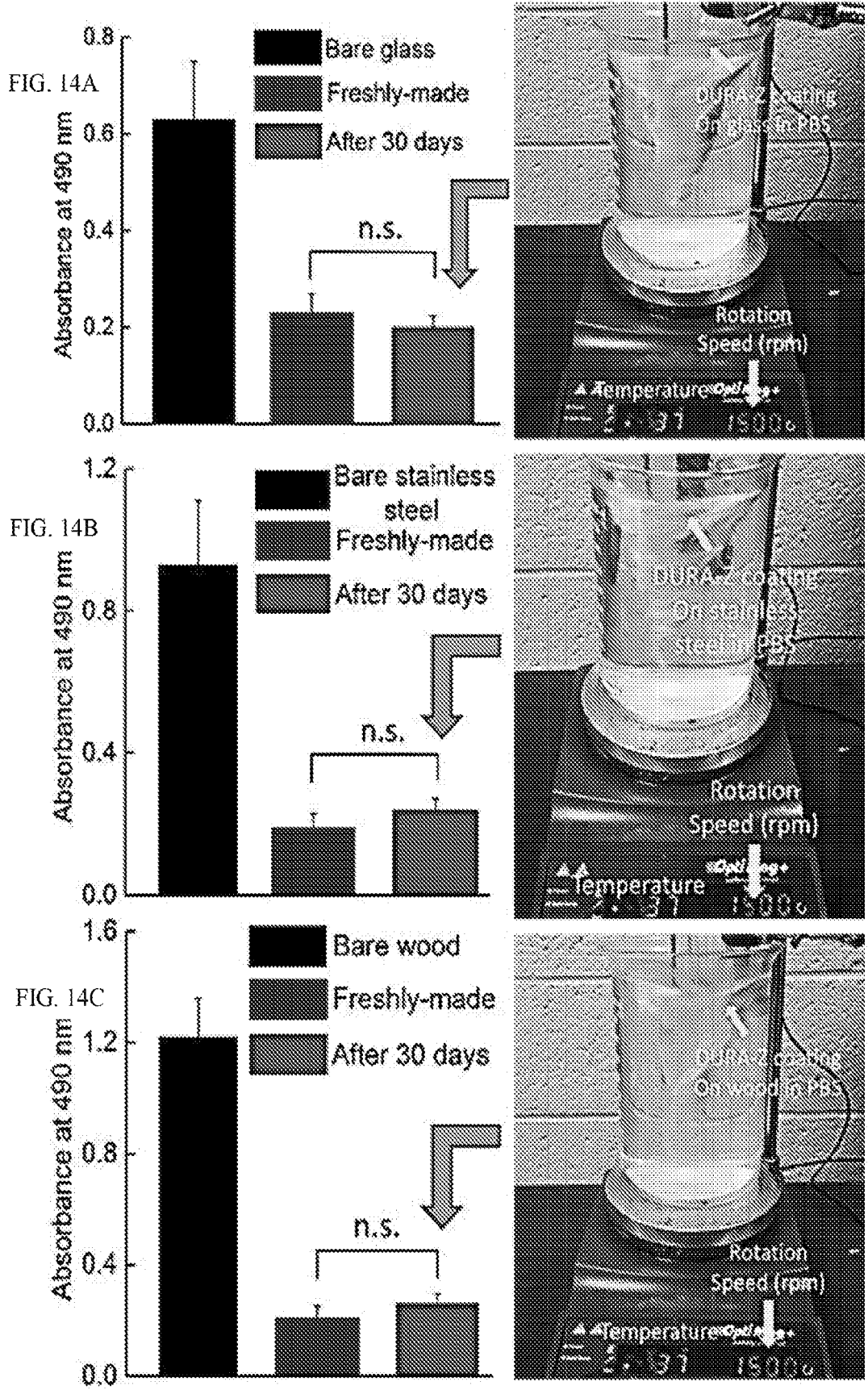
FIGS. 14A, 14B, and 14C show anti-fouling property of zwitterionic PCBAA hydrogel coating (called DURA-Z coating in FIGS. 14A, 14B, and 14C) on glass, stainless steel and wood substrates, respectively, (binding composition 1) after durability test of 30 days exposure to PBS shearing at body temperature (37 degrees C.), All data are presented as mean of replicates (n=3)±standard deviation. Statistical analysis: unpaired, two-tailed t-test, n.s.: no significant difference at P>0.05
Figures 15A, 15B:
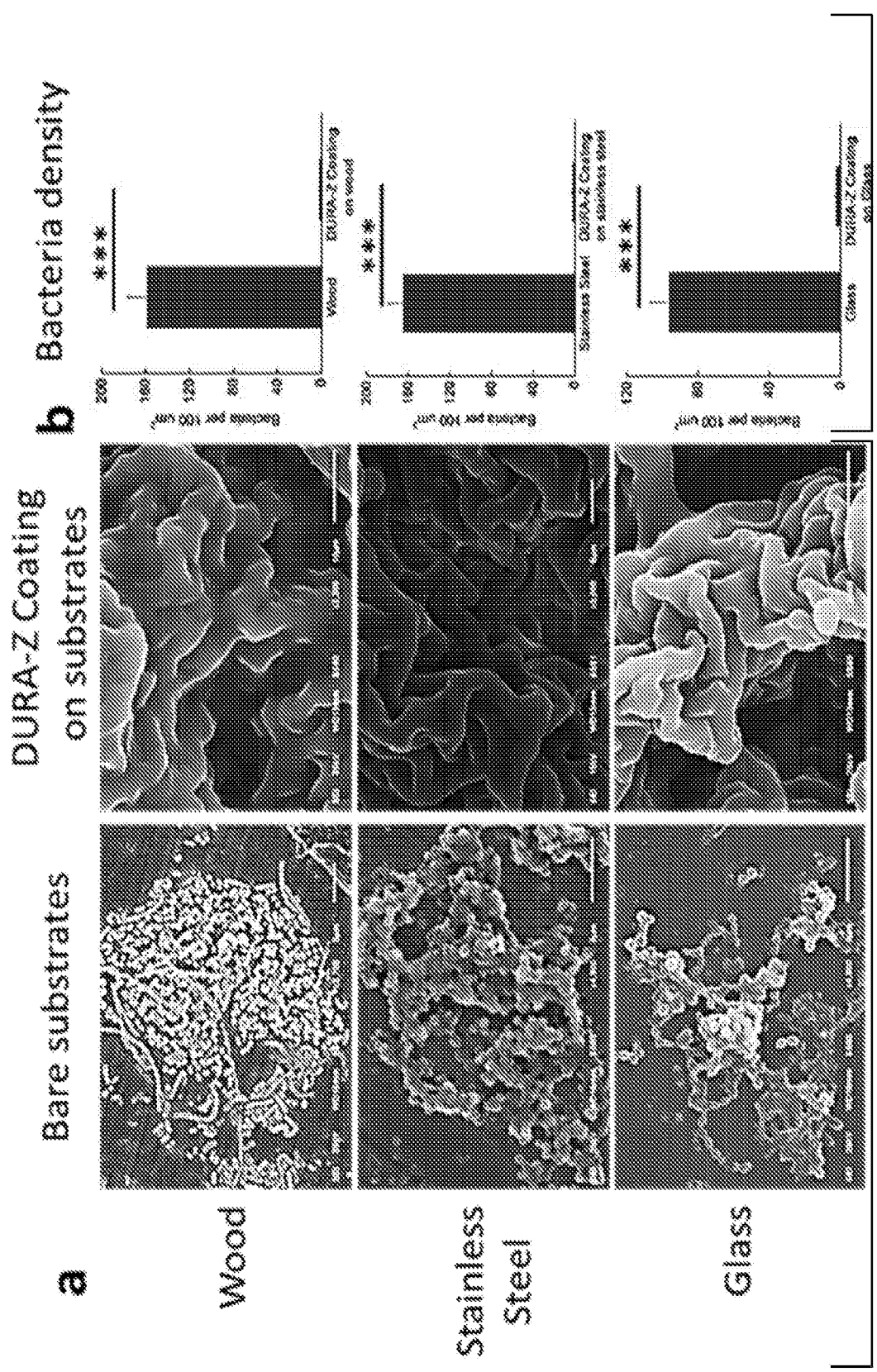
FIG. 15A shows representative SEM images of bacteria adhesion on wood, stainless steel, and glass compared with zwitterionic PCBAA hydrogel coating (called DURA-Z coating in FIG. 15A) on these substrates (binding composition 1) after 30 days of co-culture with bacteria at shaking condition.
FIG. 15B shows graphs of calculated bacterial density on wood, stainless steel, and glass compared zwitterionic PCBAA hydrogel coatings (called DURA-Z coating in FIG. 15B) on these substrates (binding composition 1). All data are presented as mean of biological replicates (n=6)±standard deviation. Statistical analysis: unpaired two-tailed t-test, ***: p<0.0001. scale bar=10 μm.

The coating composition 1 was easily applied to a variety of substrates including stainless steel, wood, and glass (FIG. 12A) by combining the coating composition 1 and superglue. Glass substrates were pre-treated with a thin layer of EVO-Stik glue before applying the coating due to the low affinity between cyanoacrylate superglue and glass. Binding composition 1 obtained on these substrates were also found to be durable as indicated by unchanged, excellent anti-fouling properties after two months of incubation in water (FIG. 13). Even under PBS shearing (1500 rpm, 202 G) at 37° C. for up to 30 days, the coating maintained its anti-fouling property on every different substrate (FIG. 14). The different substrates were also tested for *E. coli* biofilm resistance for 30 days using a dynamic bacterial challenge. Almost zero bacteria adhesion was achieved on all tested coatings in binding composition 1 despite different types of substrates were coated (FIG. 15).

Figure 12B:
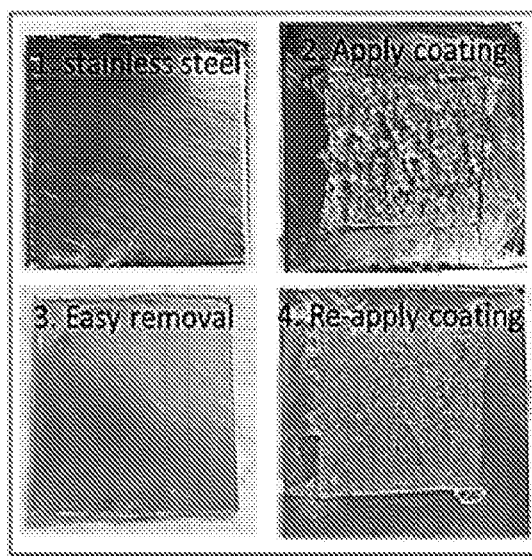
FIG. 12B illustrates easy removal and re-application of zwitterionic PCBAA hydrogel coating on stainless steel substrate.
Figure 12C:
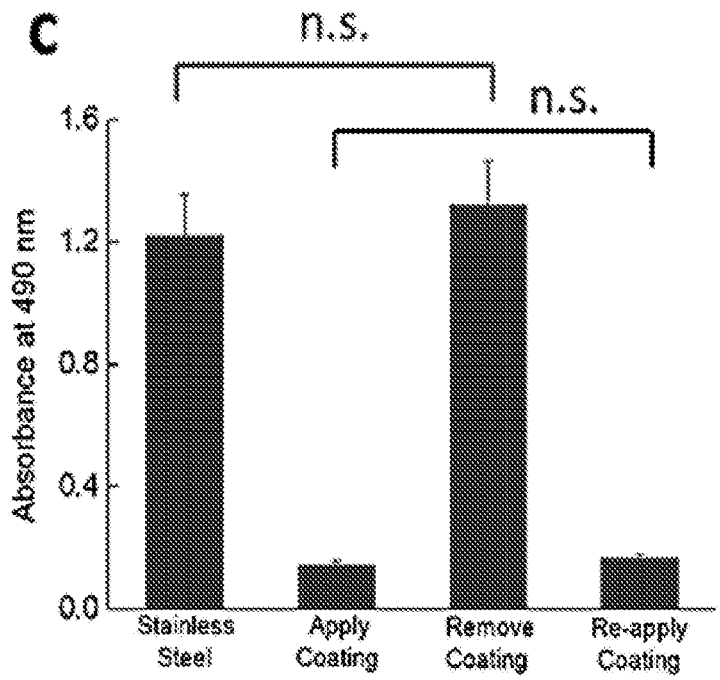
FIG. 12C is a graph showing corresponding antifouling property. All data are presented as mean of replicates (n=3)±standard deviation. Statistical analysis: unpaired, two-tailed t-test, n.s.: no significant difference at P>0.05.

A frequently-desirable property of coating layers includes fully-removing the layer from a substrate, followed by reapplying a new coating layer. This property, however, can be difficult to achieve with existing chemical surface modification methods without significantly damaging the original substrates. The coating composition 1 binds substrate surfaces through commercial superglues, which are dissolvable in organic solvents. Coating composition 1 coated stainless steel for example (FIG. 12B) was incubated in acetone for 1-hour, and the coating came off spontaneously without any damage to the substrate surface. The coating composition 1 was then re-applied to the same stainless steel substrate, and the new coating in binding composition 1 resisted protein binding as effectively as when it was first applied (FIG. 12C).

Figure 5A:
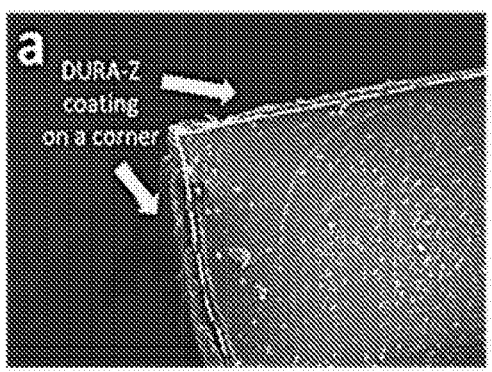
FIG. 5A is an image showing Zwitterionic PCBAA hydrogel coating (called DURA-Z coating in FIG. 5A) on a corner.
Figure 5E:
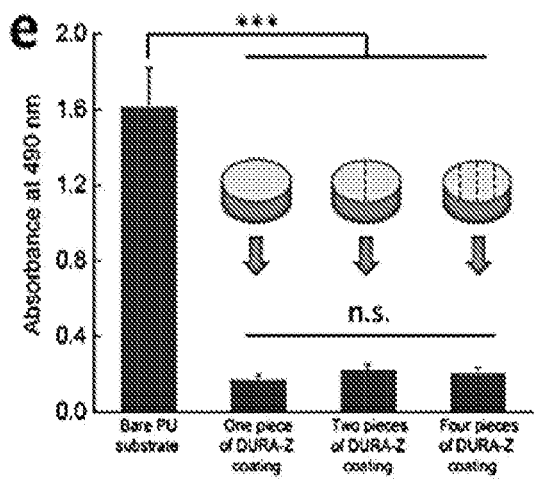
FIG. 5E shows anti-fouling property of PU substrate with two and four pieces of adjacent zwitterionic PCBAA hydrogel coatings (called DURA-Z coating in FIG. 5E). All data are presented as mean of replicates (n=3)±standard deviation. Statistical analysis: one-way ANOVA with Bonferroni multi-comparison. *: p<0.0001. n.s.: no significant difference, p>0.5
Figure 5B:
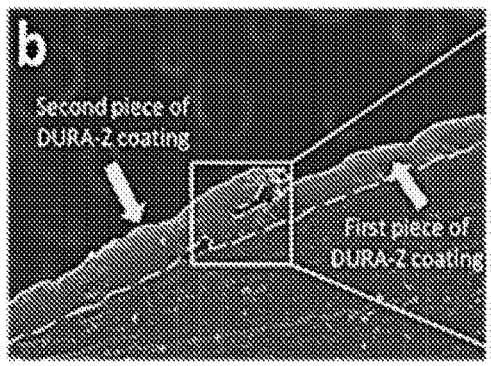
FIG. 5B is an SEM sectioning image of two adjacent pieces of zwitterionic PCBAA hydrogel coating (called DURA-Z coating in FIG. 5B)
Figure 5C:
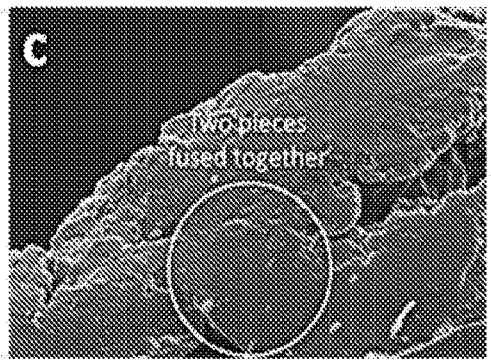
FIG. 5C is an enlarged image of FIG. 5B on the fused area.
Figure 5D:
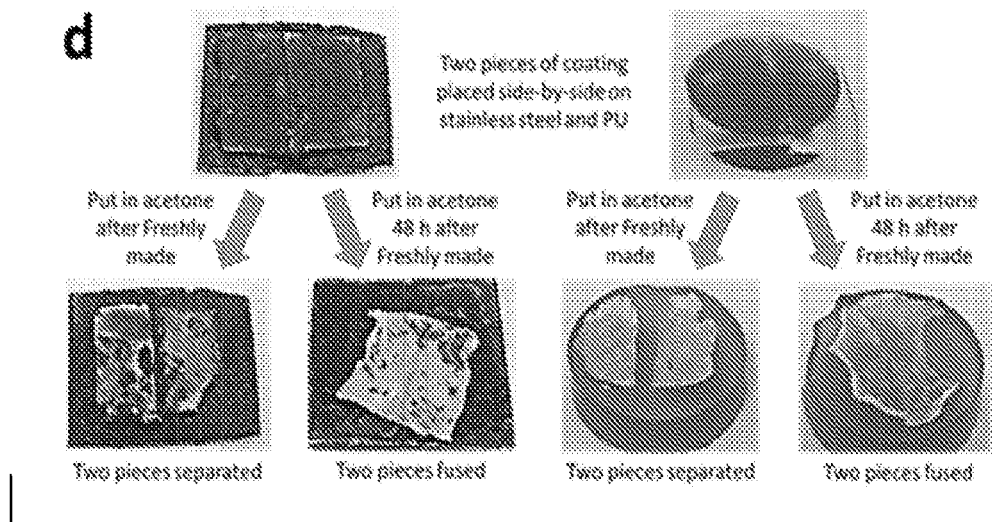
FIG. 5D shows two pieces of adjacent zwitterionic PCBAA hydrogel coatings were placed in acetone after freshly made and 48 h after freshly made.

The coating composition 1 are scalable in size, and can be curved, bent, and wrenched, and they are tailorable to fit and coat substrates with complex surface shapes. SEM images for a bent coating composition 1 on a corner using one piece (FIG. 5A) and the conjunction area between two pieces (FIG. 5B) fused, which masked the hydrophobic glue and substrate. This was achieved by the self-healing property of PCBAA hydrogels, which enabled the fusion between two adjacent hydrogel coatings (FIG. 5C). The fusion of two adjacent pieces of hydrogel coating was tested on both polyurethane and stainless steel substrates (FIG. 5D). If the coating was freshly made, the two pieces fell apart after the superglue layer was dissolved in acetone. 48 h after making the coating and then placing it in acetone, the two pieces of hydrogels fused into one. ELISA results indicated that up to 3 conjunction lines (4 pieces of coating composition 1) within ~0.8 $cm^2$ coated area did not compromise the anti-fouling property compared with the coating of the same area prepared using one piece of coating composition 1 (FIG. 5E).

Superglue was capable of strongly binding the superhydrophilic polymer network (PCBAA hydrogel) and a hydrophobic substrate together. This property is uncommon since commercial superglue is known to mostly bind hydrophobic substrates. Cyanoacrylate superglue compositions are based on the rapid solidification of hydrophobic cyanoacrylate polymers, which have low affinity with hydrophilic materials such as zwitterionic polymers. For example, linear zwitterionic PCBAA polymer powder and highly concentrated PCBAA/water solution would not readily attach to substrates using superglue (FIG. 16). The success of using superglue to strongly bind hydrophilic zwitterionic hydrogel layer (to form binding composition 1) is attributed to the inter-penetration structure formed between these two (FIGS. 2A & 2D), although this proposed mechanism should not limit the scope of the invention claimed. It is expected that during the curing process, liquid cyanoacrylate monomers penetrated into the zwitterionic hydrogel network and were crosslinked. The entanglement between the hydrogel coating and superglue networks immobilized the coating on the substrate for as long and strong as the superglue adhesive can last.

Scanning Electron Microscope (SEM) Imaging.

All samples were dried in vacuum and then coated with nano-gold using a SEEVac Conductive IV sputter coater before imaged by a JSM-6510LV scanning electron microscope. For sectional imaging, all tested disk substrates (bare polyurethane, superglue-coated and hydrogel-coated substrates (binding composition 1)) were vertically cut into half using a sharp scalpel to expose the cross-section.

Atomic-Force Microscopy (AFM) Imaging.

AFM imaging of the bare polyurethane, superglue-coated and hydrogel-coated substrates (binding composition 1) was conducted on a Dimension 3100 AFM from VEECO. All samples were vacuum dried before imaging. The coating thickness and morphology were measured in the air through the tapping mode using silicon probes (VEECO) with a nominal frequency of 150 kHz. The AFM images were analyzed using Nanoscope software version 5.12 (VEECO).

Infra-Red (IR) Spectroscopy.

Bare polyurethane, superglue-coated and hydrogel-coated substrates (binding composition 1) were vacuum dried before testing. PCBAA hydrogel was freeze-dried before testing. All samples were characterized on a NICOLET 6700 IR (Thermo Electron Corporation) equipped with an attenuated total reflectance (ATR) accessory. For the polyurethane surface, the peak at 3350 $cm^{-1}$ represented the stretching vibration of —OH. The peaks at 2870 $cm^{-1}$ and 1200 $cm^{-1}$ represented the —$CH_2$— and —$CH_3$ groups. The peak at 1710 $cm^{-1}$ represented the —CO— group. The peak at 1580 $cm^{-1}$ represented the —OCONH— group. For the surface with hydrophobic glue, the peak at 2350 $cm^{-1}$ was the characteristic peak of conjugated —CN group. The peak at 1780 $cm^{-1}$ represented the —OCO— group. The peak at 1270 $cm^{-1}$ represented the twist vibration of —$OCH_3$ group. The peaks at 2900 $cm^{-1}$, 1320 $cm^{-1}$ and 1100 $cm^{-1}$ represented the —$CH_2$— and —$CH_3$ groups. The peak at 850 $cm^{-1}$ represented unreacted =$CH_2$ group. For the hydrogel-coating and PCBAA hydrogel, the peak at 1650 $cm^{-1}$ represented the —CO— group. The peak at 1510 $cm^{-1}$ represented the —OCONH— group. The big peak between 3000 $cm^{-1}$-3300 $cm^{-1}$ represented the combination of —$COO^-$ and quaternary ammonium groups. The peaks at 2930 $cm^{-1}$, 1340 $cm^{-1}$ and 1070 $cm^{-1}$ represented the —$CH_2$— and —$CH_3$ groups. The peak at 1390 $cm^{-1}$ was the characteristic peak for the symmetrical vibration of —COO— group.

Contact Angle.

The water contact angle on bare polyurethane, superglue-coated and hydrogel-coated substrates (binding composition 1) was conducted using a KSV contact angle instrument equipped with a camera at room temperature and ambient humidity. 2 µl of water was dropped on different surfaces and water contact angle was calculated using the CAM2008 software.

Durability Tests in Aqueous Environment.

Phosphate-buffered saline (PBS) shearing was created on a stirring plate by a 5-cm stirring bar at 1500 rpm in a beaker (D=10 cm). The tested samples (hydrogel coating on polyurethane, glass, wood, and stainless steel substrates (binding composition 1)) were firmly clamped and positioned at the inner wall of the beaker, and subjected to the continuous shear stress of 202 G. Body temperature (37° C.) was controlled by the stirring plate and deionized water was added to compensate the evaporation every day to maintain standard PBS concentration. In the water flushing test, water was cycled by an electric pump with a flow rate of 42.8 ml/s. In the dry/wet stability test, the hydrogel-coating in binding composition 1 was completely dried under air flow and re-hydrated in water. 10 dry/wet cycles were conducted before protein adsorption test. The protein adsorption test was conducted on the samples before and after the durability challenge.

Mechanical Damage Tests.

For the knife-scratch test, the hydrogel-coating on a polyurethane disk substrate was randomly cut by a sharp scalpel. The abrasion test was conducted on an INSTRON compressor equipped with a precise loading detector. Sandpapers (Gator waterproof sanding 400 grit) were fixed on both sides of the compressor and the pressure was calculated by the loading divided by the area of the polyurethane disk substrate. One cycle of abrasion contains pushing and pulling the disk substrate for 1-cm displacement back and forth under a given pressure. The samples were subjected to 20 cycles of abrasion. Water wettability and protein adsorption tests were conducted on the samples before and after the mechanical damage challenge.

Friction Index Measurement.

The sandpaper was fixed on a ruler and the polyurethane disk substrate with or without the hydrogel-coating was placed on one end of the ruler, which was then slowly lifted up. Immediately when the disk substrate could slide down spontaneously, the lifting angle (θ) of the ruler was recorded.

The friction index between the disk substrate and sandpaper was be calculated by tangent θ.

Platelet Adhesion Test.

Rat blood was collected and transferred to a centrifuge tube containing 1 mg/ml heparin sodium. The blood was then centrifuged for 10 min at 700 RCF. The resulting plasma in the top layer was collected and applied to a polyurethane substrate, superglue surface, and hydrogel-coating (binding composition 1) overnight at 37° C. After PRP challenging, the sample surfaces were fixed in 2.5% glutaraldehyde, dehydrated in gradient ethanol, and dried by vacuum. Adhered platelets were visualized and calculated under a scanning electron microscope.

Protein Absorption Test (ELISA).

Human fibrinogen (Fg, Sigma-Aldrich) adsorption on a variety of substrates (bare substrates, superglue coated, and hydrogel-coated substrates (binding composition 1)) was measured using an enzyme-linked immunosorbent assay (ELISA). All samples were incubated with 1 mg/mL fibrinogen for 10 minutes at room temperature, followed by 5 washes with PBS buffer. They were then incubated with 1 mg/mL bovine serum albumin solution for 10 minutes at room temperature with 5 washes again with phosphate buffered saline. The samples were removed from the fifth phosphate buffered saline wash and transferred to new wells. They were next incubated with a 1:200-dilution of horseradish peroxidase (HRP)-conjugated anti-fibrinogen (US-Biological, Life Sciences) in phosphate buffered saline for 10 minutes, followed by another 5 washes with phosphate buffered saline. After the fifth wash, the samples were transferred to new wells and SIGMAFAST OPD (Sigma-Aldrich) was added to each well. The samples were incubated in the SIGMAFAST OPD solution for 30 minutes in the dark. The supernatant was removed from each test well, transferred to a 96-well plate, and its absorbance at 490 nm was measured using a UV-VIS spectrometer (Thermo Scientific Multiscan Go). All samples were measured in triplicate.

Biofilm Resistance of the Hydrogel-Coating.

*E. coli*, *S. aureus*, and *C. ablicans* bacteria were cultured for 24 hours at 37° C. on agar plates (Luria-Bertani (LB) agar for *E. coli*, Tryptic Soy (TS) agar for *S. aureus* and Yeast Mold (YM) Agar for *C. ablicans*). One colony was picked and cultured in 20 mL of Luria-Bertani (LB) broth for *E. coli*, tryptic soy (TS) broth for *S. aureus*, and yeast mold (YM) broth for *C. ablicans* overnight at 37° C. on a shaker (Standard Analog Shaker, VWR) at 200 rpm. The resulting culture was used to inoculate a second culture in 50 mL of broth medium until an optical density (OD) of 0.8 at 600 nm was reached. The bacteria were collected by centrifugation at 8,000×g for 10 minutes at 4° C., washed three times with sterile PBS (pH 7.4) and finally suspended in broth to get a final concentration of $1.05 \times 10^9$ cells per ml (OD=1.31 at 600 nm) for the biofilm formation test. In the dynamic method, polyurethane (stainless steel, wood, and glass) substrates, superglue-coated substrates, and hydrogel-coated substrates (binding composition 1) were placed in bacterial culture medium (broth medium) containing highly concentrated bacteria ($1.05 \times 10^9$ cells per ml) at 37° C. for 30 days under continuous shaking (300 rpm). The culture medium was gently refreshed every two days, and the bacterial density within the refreshed medium was kept at $1.05 \times 10^9$ cells per mL. In the static method, polyurethane substrates, superglue-coated substrates and hydrogel-coated substrates (binding composition 1) were stationarily placed in bacterial culture medium (broth medium) containing highly concentrated bacteria ($1.05 \times 10^9$ cells per mL) at 37° C. for 30 days. Bacteria were allowed to settle on the surface of the substrates by gravity. The culture medium was gently refreshed day by day, and the bacterial density within the refreshed medium was kept at $1.05 \times 10^9$ cells per mL. After long-term incubation, all substrates were rinsed with PBS for 30 minutes (samples tested in the static method were also imaged without rinsing). After the challenging periods, the substrates were then immersed in the fix solution of 2.5% glutaraldehyde, 2% paraformaldehyde in 0.1 M sodium phosphate buffer and were then dehydrated in a gradient ethanol series and dried in vacuum before SEM imaging. Adherent bacteria density was counted by averaging 6 randomly selected areas (100 μm² each).

Precursor Hydrogels.

According to aspects, for generation of a binding composition, including a hydrogel and a hydrophobic glue, wherein at least a portion of the gel network of the hydrogel is occupied by the hydrophobic glue, the hydrogel can be a precursor hydrogel for a zwitterionic hydrogel polymer.

The precursor hydrogels include ester derivatives of the carboxylate acid group in crosslinked zwitterionic poly-carboxybetaine methacrylate (PCBMA), crosslinked zwitterionic poly-carboxybetaine acrylamide (PCBAA), non-crosslinked zwitterionic PCBAA.

The ester of the carboxylate acid group has a general formula —C(=O)—OR, and R is an alkyl, aryl, acyl, or silyl group that may be further substituted with one or more substituents.

The ester comprises tert butyl ester (tBu).

The precursor hydrogels include a derivative of one or more of forgoing precursor hydrogels, or one or more of forgoing precursor hydrogels together with one or more of other hydrogels including crosslinked poly-acrylic acid, crosslinked poly(vinyl alcohol), non-crosslinked poly(vinyl alcohol), crosslinked poly(vinylpyrrolidone), non-crosslinked poly(vinylpyrrolidone), silicone-containing hydrogel, crosslinked polyacrylamide, crosslinked poly-(N-isopropyl-acrylamide), non-crosslinked poly-(N-isopropyl-acrylamide), crosslinked poly-methyl-methacrylate, poly-hydroxy-ethyl-methacrylate (PHEMA), crosslinked polyethylene glycol (PEG), crosslinked poly(ethylene glycol) methacrylate (PEGMA), crosslinked poly(ethylene glycol) diacrylate (PEGDA), polypropylene glycol, crosslinked zwitterionic poly-(sulfobetaine methacrylate) (PSBMA), crosslinked zwitterionic 2-methacryloyloxyethyl phosphorylcholine (PMPC), crosslinked zwitterionic poly-carboxybetaine methacrylate (PCBMA), crosslinked zwitterionic poly-carboxybetaine acrylamide (PCBAA), non-crosslinked zwitterionic PCBAA, crosslinked alginate, crosslinked chitosan, gelatin, collagen, fibrin, agarose, hyaluronic acid, cellulose, polypeptides, or a derivative of one or more of the foregoing.

The precursor hydrogels are more hydrophobic compared with native zwitterionic hydrogels and improve the physical entanglement of their polymer chains with hydrophobic glue polymers or substrate polymers.

After forming the binding composition, the precursor hydrogel can be treated to convert to zwitterionic hydrogel, where the ester groups are hydrolyzed to form carboxylate acid, regenerating the zwitterionic carboxybetaine chemical structure.

To hydrolyze the ester groups, the treatment includes the use of acid or base.

To hydrolyze the tert-butyl ester groups, the treatment includes the use of trifluoroacetic acid and its derivative solutions.

The hydrolyzing treatment will not deteriorate the physical entanglement in the binding composition.

Synthesis of CBAA-tBu monomer. 5 g N-((3-Dimethylamino)propyl)acrylamide (DAA) and 8.68 g tert-butyl bromoacetate were reacted in 20 ml acetonitrile for 24 h at 50 C under N2 protection. After the reaction, 250 ml ethyl ether were dropped to the reaction mixture, which was placed at 4° C. overnight. The formed white crystals were isolated and washed several times with ethyl ether, followed by vacuum drying. The synthesized CBAA-tBu monomers were stored in a desiccator at −20 C (yield 90%).

Synthesis of PCBAA-tBu hydrogel. Briefly, 5 mg I-2959 initiator and 30 mg MBAA crosslinker were dissolved in 10 ml anhydrous methanol. 300 mg CBAA-tBu monomer was then dissolved in 300 µl initiator/crosslinker solution to prepare a pre-gel solution, which was transferred to between two glass slides separated with a Teflon spacer (1 mm in thickness). UV was applied for a few minutes to crosslink the PCBAA-tBu hydrogel. The obtained PCBAA-tBu hydrogel was equilibrated in anhydrous dichloromethane (DCM) before use.

Zwitterionic PCBAA Hydrogel Coating Composition (Coating Composition 1)

Synthesis of PCBAA hydrogel coating composition (hydrogel tapes): PCBAA hydrogel tapes were fabricated by in-situ forming of a thin layer of PCBAA hydrogel on commercially available polypropylene liner. Briefly, 5 mg 2-Hydroxy-4'-(2-hydroxyethoxy)-2-methylpropiophenone (I-2959) initiator and 30 mg N,N'-Methylenebis(acrylamide) (MBAA) crosslinker were dissolved in 10 ml DI water. 300 mg 3-((3-acrylamidopropyl)dimethylammonio) propanoate (CBAA) monomer was then dissolved in 300 µl initiator/crosslinker solution to prepare a pre-gel solution, which was transferred to between two polypropylene liners adhered to glass slides separated by a Teflon spacer (1 mm in thickness). UV was applied for a few minutes to crosslink the PCBAA hydrogel. PCBAA hydrogel tape was obtained by removing the hydrogel layer along with the liners from glass slides.

Zwitterionic PCBAA Hydrogel Binding Composition (Binding Composition 1)

The polyurethane (PU), stainless steel, glass, wood, and PVC panel substrates were cleaned with alcohol and dried in air (wood and metal were pre-treated by sandpaper to obtain rough surfaces, and glass was pre-coated with a thin layer of EVO-stik glue). To prepare epoxy painted steel substrate, Blue Water two part bottom epoxy was pre-mixed at the primer: hardener ratio of 5:1 following the manufacture's manual, and applied on the surface of a flat sheet of McMaster low carbon steel that has been previous prepared using a sand paper. 24 h was allowed for the epoxy paint to cure. Then cyanoacrylate superglue (ACE Hardware Corp.) was applied onto the different substrates, followed by pressing the PCBAA hydrogel tape, Coating composition 1, (hydrogel layer with the side without liner facing down) onto the superglue for a few seconds. One hour was then allowed to completely solidify the superglue. The liner on top of the hydrogel was removed, and the glued coating was obtained. For additional test on the coating, the glued coating was transferred to DI water for equilibrium such as for 20 mins, and the PCBAA hydrogel coating was optionally polished either by a small shovel or tweezer, resulting the surface with a thin layer of coating.

Zwitterionic PCBMA Hydrogel Coating Composition (Coating Composition 2)

Synthesis of PCBMA hydrogel coating composition (hydrogel tapes): PCBMA hydrogel tapes were fabricated by in-situ forming of a thin layer of PCBMA hydrogel on commercially available polypropylene liner. Briefly, 5 mg 2-Hydroxy-4'-(2-hydroxyethoxy)-2-methylpropiophenone (I-2959) initiator and 30 mg N,N'-Methylenebis(acrylamide) (MBAA) crosslinker were dissolved in 10 ml DI water. 300 mg 3-[[2-(Methacryloyloxy)ethyl]dimethylammonio]propionate (CBMA) monomer was then dissolved in 300 µl initiator/crosslinker solution to prepare a pre-gel solution, which was transferred to between two polypropylene liners adhered to glass slides separated by a Teflon spacer (1 mm in thickness). UV was applied for a few minutes to crosslink the PCBMA hydrogel. PCBMA hydrogel tape was obtained by removing the hydrogel layer along with the liners from glass slides.

Zwitterionic PCBMA Hydrogel Binding Composition (Binding Composition 2)

The polyurethane (PU), stainless steel, glass, wood, and PVC panel substrates were cleaned with alcohol and dried in air (wood and metal were pre-treated by sandpaper to obtain rough surfaces, and glass was pre-coated with a thin layer of EVO-stik glue). To prepare epoxy painted steel substrate, Blue Water two part bottom epoxy was pre-mixed at the primer: hardener ratio of 5:1 following the manufacture's manual, and applied on the surface of a flat sheet of McMaster low carbon steel that has been previous prepared using a sand paper. 24 h was allowed for the epoxy paint to cure. Then cyanoacrylate superglue (ACE Hardware Corp.) was applied onto the different substrates, followed by pressing the PCBMA hydrogel tape, Coating composition 2, (hydrogel layer with the side without liner facing down) onto the superglue for a few seconds. One hour was then allowed to completely solidify the superglue. The liner on top of the hydrogel was removed, and the glued coating was obtained. For additional test on the coating, the glued coating was transferred to DI water for equilibrium such as for 20 mins, and the PCBMA hydrogel coating was optionally polished either by a small shovel or tweezer, resulting the surface with a thin layer of coating.

Zwitterionic PSBMA Hydrogel Coating Composition (Coating Composition 3)

Synthesis of PSBMA hydrogel coating composition (hydrogel tapes): PSBMA hydrogel tapes were fabricated by in-situ forming of a thin layer of PSBMA hydrogel on commercially available polypropylene liner. Briefly, 5 mg 2-Hydroxy-4'-(2-hydroxyethoxy)-2-methylpropiophenone (I-2959) initiator and 30 mg N,N'-Methylenebis(acrylamide) (MBAA) crosslinker were dissolved in 10 ml DI water. 300 mg [2-(Methacryloyloxy)ethyl]dimethyl-(3-sulfopropyl) ammonium hydroxide (SBMA) monomer was then dissolved in 300 µl initiator/crosslinker solution to prepare a pre-gel solution, which was transferred to between two polypropylene liners adhered to glass slides separated by a Teflon spacer (1 mm in thickness). UV was applied for a few minutes to crosslink the PSBMA hydrogel. PSBMA hydrogel tape tapes were obtained by removing the hydrogel layer along with the liners from glass slides.

Zwitterionic PSBMA Hydrogel Binding Composition (Binding Composition 3)

The polyurethane (PU), stainless steel, glass, wood, and PVC panel substrates were cleaned with alcohol and dried in air (wood and metal were pre-treated by sandpaper to obtain rough surfaces, and glass was pre-coated with a thin layer of EVO-stik glue). To prepare epoxy painted steel substrate, Blue Water two part bottom epoxy was pre-mixed at the primer: hardener ratio of 5:1 following the manufacture's manual, and applied on the surface of a flat sheet of McMaster low carbon steel that has been previous prepared using a sand paper. 24 h was allowed for the epoxy paint to cure. Then cyanoacrylate superglue (ACE Hardware Corp.)

was applied onto the different substrates, followed by pressing the PSBMA hydrogel tape, Coating composition 3, (hydrogel layer with the side without liner facing down) onto the superglue for a few seconds. One hour was then allowed to completely solidify the superglue. The liner on top of the hydrogel was removed, and the glued coating was obtained. For additional test on the coating, the glued coating was transferred to DI water for equilibrium such as for 20 mins, and the PSBMA hydrogel coating was optionally polished either by a small shovel or tweezer, resulting the surface with a thin layer of coating.

Zwitterionic PMPC Hydrogel Coating Composition (Coating Composition 4)

Synthesis of PMPC hydrogel coating composition (hydrogel tapes): PMPC hydrogel tapes were fabricated by in-situ forming of a thin layer of PMPC hydrogel on commercially available polypropylene liner. Briefly, 5 mg 2-Hydroxy-4'-(2-hydroxyethoxy)-2-methylpropiophenone (I-2959) initiator and 30 mg N,N'-Methylenebis(acrylamide) (MBAA) crosslinker were dissolved in 10 ml DI water. 300 mg 2-Methacryloyloxyethyl Phosphorylcholine (MPC) monomer was then dissolved in 300 μl initiator/crosslinker solution to prepare a pre-gel solution, which was transferred to between two polypropylene liners adhered to glass slides separated by a Teflon spacer (1 mm in thickness), UV was applied for a few minutes to crosslink the PMPC hydrogel. PMPC hydrogel tapes were obtained by removing the hydrogel layer along with the liners from glass slides.

Zwitterionic PMPC Hydrogel Binding Composition (Binding Composition 4)

The polyurethane (PU), stainless steel, glass, wood, and PVC panel substrates were cleaned with alcohol and dried in air (wood and metal were pre-treated by sandpaper to obtain rough surfaces, and glass was pre-coated with a thin layer of EVO-stik glue). To prepare epoxy painted steel substrate, Blue Water two part bottom epoxy was pre-mixed at the primer: hardener ratio of 5:1 following the manufacture's manual, and applied on the surface of a flat sheet of McMaster low carbon steel that has been previous prepared using a sand paper. 24 h was allowed for the epoxy paint to cure. Then cyanoacrylate superglue (ACE Hardware Corp.) was applied onto the different substrates, followed by pressing the PMPC hydrogel tape, Coating composition 4, (hydrogel layer with the side without liner facing down) onto the superglue for a few seconds. One hour was then allowed to completely solidify the superglue. The liner on top of the hydrogel was removed, and the glued coating was obtained. For additional test on the coating, the glued coating was transferred to DI water for equilibrium such as for 20 mins, and the PMPC hydrogel coating was optionally polished either by a small shovel or tweezer, resulting the surface with a thin layer of coating.

PEG Hydrogel Coating Composition (Coating Composition 5)

Synthesis of PEG hydrogel coating composition (hydrogel tapes): PEGMA hydrogel tapes were fabricated by in-situ forming of a thin layer of PEGMA hydrogel on commercially available polypropylene liner. Briefly, 5 mg 2-Hydroxy-4'-(2-hydroxyethoxy)-2-methylpropiophenone (I-2959) initiator and 30 mg N,N'-Methylenebis(acrylamide) (MBAA) crosslinker were dissolved in 10 ml DI water. 300 mg Poly(ethylene glycol) methacrylate (PEGMA, Mn 500) monomer was then dissolved in 300 μl initiator/crosslinker solution to prepare a pre-gel solution, which was transferred to between two polypropylene liners adhered to glass slides separated by a Teflon spacer (1 mm in thickness). UV was applied for a few minutes to crosslink the PEGMA hydrogel. PEGMA hydrogel tapes were obtained by removing the hydrogel layer along with the liners from glass slides.

PEG Hydrogel Binding Composition (Binding Composition 5)

The polyurethane (PU), stainless steel, glass, wood, and PVC panel substrates were cleaned with alcohol and dried in air (wood and metal were pre-treated by sandpaper to obtain rough surfaces, and glass was pre-coated with a thin layer of EVO-stik glue). To prepare epoxy painted steel substrate, Blue Water two part bottom epoxy was pre-mixed at the primer: hardener ratio of 5:1 following the manufacture's manual, and applied on the surface of a flat sheet of McMaster low carbon steel that has been previous prepared using a sand paper. 24 h was allowed for the epoxy paint to cure. Then cyanoacrylate superglue (ACE Hardware Corp.) was applied onto the different substrates, followed by pressing the PEGMA hydrogel tape, Coating composition 5, (hydrogel layer with the side without liner facing down) onto the superglue for a few seconds. One hour was then allowed to completely solidify the superglue. The liner on top of the hydrogel was removed, and the glued coating was obtained. For additional test on the coating, the glued coating was transferred to DI water for equilibrium such as for 20 mins, and the PEGMA hydrogel coating was optionally polished either by a small shovel or tweezer, resulting the surface with a thin layer of coating.

Zwitterionic PCBAA-Polyacrylamide Hydrogel Coating Composition (Coating Composition 6)

Synthesis of zwitterionic PCBAA-polyacrylamide hydrogel coating composition (hydrogel tapes): zwitterionic PCBAA-polyacrylamide hydrogel tapes were fabricated by in-situ forming of a thin layer of PCBAA-polyacrylamide hydrogel on commercially available polypropylene liner. Briefly, 5 mg 2-Hydroxy-4'-(2-hydroxyethoxy)-2-methylpropiophenone (I-2959) initiator and 30 mg N,N'-Methylenebis(acrylamide) (MBAA) crosslinker were dissolved in 10 ml DI water. 30 mg CBAA monomer and 270 mg acrylamide monomer was then dissolved in 300 μl initiator/crosslinker solution to prepare a pre-gel solution (the amount of the CBAA monomer among the total CBAA and acrylamide monomers in the reaction mixture was 10%), which was transferred to between two polypropylene liners adhered to glass slides separated by a Teflon spacer (1 mm in thickness). UV was applied for a few minutes to crosslink the hydrogel. PCBAA-polyacrylamide hydrogel tape was obtained by removing the hydrogel layer along with the liners from glass slides.

Zwitterionic PCBAA-Polyacrylamide Hydrogel Binding Composition (Binding Composition 6)

The polyurethane (PU), stainless steel, glass, wood, and PVC panel substrates were cleaned with alcohol and dried in air (wood and metal were pre-treated by sandpaper to obtain rough surfaces, and glass was pre-coated with a thin layer of EVO-stik glue). To prepare epoxy painted steel substrate, Blue Water two part bottom epoxy was pre-mixed at the primer: hardener ratio of 5:1 following the manufacture's manual, and applied on the surface of a flat sheet of McMaster low carbon steel that has been previous prepared using a sand paper. 24 h was allowed for the epoxy paint to cure. Then cyanoacrylate superglue (ACE Hardware Corp.) was applied onto the different substrates, followed by pressing the zwitterionic PCBAA-polyacrylamide hydrogel tape, Coating composition 6, (hydrogel layer with the side without liner facing down) onto the superglue for a few seconds. One hour was then allowed to completely solidify the superglue. The liner on top of the hydrogel was removed, and the glued coating was obtained. For additional test on the coating, the glued coating was transferred to DI water for equilibrium such as for 20 mins, and the zwitterionic PCBAA-polyacrylamide hydrogel coating was optionally polished either by a small shovel or tweezer, resulting the surface with a thin layer of coating.

Zwitterionic PCBAA-Polyacrylamide Hydrogel Coating Composition (Coating Composition 7)

Synthesis of zwitterionic PCBAA-polyacrylamide hydrogel coating composition (hydrogel tapes): zwitterionic PCBAA-polyacrylamide hydrogel tapes were fabricated by in-situ forming of a thin layer of PCBAA-polyacrylamide hydrogel on commercially available polypropylene liner. Briefly, 5 mg 2-Hydroxy-4'-(2-hydroxyethoxy)-2-methylpropiophenone (I-2959) initiator and 30 mg N,N'-Methylenebis(acrylamide) (MBAA) crosslinker were dissolved in 10 ml DI water. 15 mg CBAA monomer and 285 mg acrylamide monomer was then dissolved in 300 µl initiator/crosslinker solution to prepare a pre-gel solution (the amount of the CBAA monomer among the total CBAA and acrylamide monomers in the reaction mixture was 5%), which was transferred to between two polypropylene liners adhered to glass slides separated by a Teflon spacer (1 mm in thickness). UV was applied for a few minutes to crosslink the hydrogel. PCBAA-polyacrylamide hydrogel tape was obtained by removing the hydrogel layer along with the liners from glass slides.

Zwitterionic PCBAA-Polyacrylamide Hydrogel Binding Composition (Binding Composition 7)

The polyurethane (PU), stainless steel, glass, wood, and PVC panel substrates were cleaned with alcohol and dried in air (wood and metal were pre-treated by sandpaper to obtain rough surfaces, and glass was pre-coated with a thin layer of EVO-stik glue). To prepare epoxy painted steel substrate, Blue Water two part bottom epoxy was pre-mixed at the primer: hardener ratio of 5:1 following the manufacture's manual, and applied on the surface of a flat sheet of McMaster low carbon steel that has been previous prepared using a sand paper. 24 h was allowed for the epoxy paint to cure. Then cyanoacrylate superglue (ACE Hardware Corp.) was applied onto the different substrates, followed by pressing the zwitterionic PCBAA-polyacrylamide hydrogel tape, Coating composition 7, (hydrogel layer with the side without liner facing down) onto the superglue for a few seconds. One hour was then allowed to completely solidify the superglue. The liner on top of the hydrogel was removed, and the glued coating was obtained. For additional test on the coating, the glued coating was transferred to DI water for equilibrium such as for 20 mins, and the zwitterionic PCBAA-polyacrylamide hydrogel coating was optionally polished either by a small shovel or tweezer, resulting the surface with a thin layer of coating.

Zwitterionic PCBAA-Polyacrylamide Hydrogel Coating Composition (Coating Composition 8)

Synthesis of zwitterionic PCBAA-polyacrylamide hydrogel coating composition (hydrogel tapes): zwitterionic PCBAA-polyacrylamide hydrogel tapes were fabricated by in-situ forming of a thin layer of PCBAA-polyacrylamide hydrogel on commercially available polypropylene liner. Briefly, 5 mg 2-Hydroxy-4'-(2-hydroxyethoxy)-2-methylpropiophenone (I-2959) initiator and 30 mg N,N'-Methylenebis(acrylamide) (MBAA) crosslinker were dissolved in 10 ml DI water. 60 mg CBAA monomer and 240 mg acrylamide monomer was then dissolved in 300 µl initiator/crosslinker solution to prepare a pre-gel solution (the amount of the CBAA monomer among the total CBAA and acrylamide monomers in the reaction mixture was 20%), which was transferred to between two polypropylene liners adhered to glass slides separated by a Teflon spacer (1 mm in thickness). UV was applied for a few minutes to crosslink the hydrogel. PCBAA-polyacrylamide hydrogel tape was obtained by removing the hydrogel layer along with the liners from glass slides.

Zwitterionic PCBAA-Polyacrylamide Hydrogel Binding Composition (Binding Composition 8)

The polyurethane (PU), stainless steel, glass, wood, and PVC panel substrates were cleaned with alcohol and dried in air (wood and metal were pre-treated by sandpaper to obtain rough surfaces, and glass was pre-coated with a thin layer of EVO-stik glue). To prepare epoxy painted steel substrate, Blue Water two part bottom epoxy was pre-mixed at the primer: hardener ratio of 5:1 following the manufacture's manual, and applied on the surface of a flat sheet of McMaster low carbon steel that has been previous prepared using a sand paper. 24 h was allowed for the epoxy paint to cure. Then cyanoacrylate superglue (ACE Hardware Corp.) was applied onto the different substrates, followed by pressing the zwitterionic PCBAA-polyacrylamide hydrogel tape, Coating composition 8. (hydrogel layer with the side without liner facing down) onto the superglue for a few seconds. One hour was then allowed to completely solidify the superglue. The liner on top of the hydrogel was removed, and the glued coating was obtained. For additional test on the coating, the glued coating was transferred to DI water for equilibrium such as for 20 mins, and the zwitterionic PCBAA-polyacrylamide hydrogel coating was optionally polished either by a small shovel or tweezer, resulting the surface with a thin layer of coating.

Zwitterionic PCBAA-Polyacrylamide Hydrogel Coating Composition (Coating Composition 9)

Synthesis of zwitterionic PCBAA-polyacrylamide hydrogel coating composition (hydrogel tapes): zwitterionic PCBAA-polyacrylamide hydrogel tapes were fabricated by in-situ forming of a thin layer of PCBAA-polyacrylamide hydrogel on commercially available polypropylene liner. Briefly, 5 mg 2-Hydroxy-4'-(2-hydroxyethoxy)-2-methylpropiophenone (I-2959) initiator and 30 mg N,N'-Methylenebis(acrylamide) (MBAA) crosslinker were dissolved in 10 ml DI water. 150 mg CBAA monomer and 150 mg acrylamide monomer was then dissolved in 300 µl initiator/crosslinker solution to prepare a pre-gel solution (the amount of the CBAA monomer among the total CBAA and acrylamide monomers in the reaction mixture was 50%), which was transferred to between two polypropylene liners adhered to glass slides separated by a Teflon spacer (1 mm in thickness). UV was applied for a few minutes to crosslink the hydrogel. PCBAA-polyacrylamide hydrogel tape was obtained by removing the hydrogel layer along with the liners from glass slides.

Zwitterionic PCBAA-Polyacrylamide Hydrogel Binding Composition (Binding Composition 9)

The polyurethane (PU), stainless steel, glass, wood, and PVC panel substrates were cleaned with alcohol and dried in air (wood and metal were pre-treated by sandpaper to obtain rough surfaces, and glass was pre-coated with a thin layer of EVO-stik glue). To prepare epoxy painted steel substrate, Blue Water two part bottom epoxy was pre-mixed at the primer: hardener ratio of 5:1 following the manufacture's manual, and applied on the surface of a flat sheet of McMaster low carbon steel that has been previous prepared using a sand paper. 24 h was allowed for the epoxy paint to cure. Then cyanoacrylate superglue (ACE Hardware Corp.) was applied onto the different substrates, followed by pressing the zwitterionic PCBAA-polyacrylamide hydrogel tape, Coating composition 9, (hydrogel layer with the side without liner facing down) onto the superglue for a few seconds. One hour was then allowed to completely solidify the superglue. The liner on top of the hydrogel was removed, and the glued coating was obtained. For additional test on the coating, the glued coating was transferred to DI water for equilibrium such as for 20 mins, and the zwitterionic PCBAA-polyacrylamide hydrogel coating was optionally polished either by a small shovel or tweezer, resulting the surface with a thin layer of coating.

Anti Marine Fouling Test of Zwitterionic PCBAA Hydrogel Binding Composition (Binding Composition 1)

The Zwitterionic PCBAA Hydrogel Binding Composition (Binding Composition 1) Resists ULVA Zoospores ULVA zoospore adhesion test. The ULVA algae were purchased from Carolina Biology Supply and shipped directly from the Atlantic Ocean in Maine. Soon upon arrival, the algae were washed thoroughly with sterile seawater to remove the unwanted marine plant and creatures. The algae were then transferred to a conical flask with Algae Gro culture media on a shaker at 16 h light/8 h dark cycle. Two days after culture, the culture media was collected and filtered with 20 μm membrane. The ULVA zoospores were concentrated by ultrafiltration with 1000 kDa cutoff Mw membranes at 1500 rpm for 3 min. Zoospore concentration of $8 \times 10^6$ cell/mL had been determined by OD-600 value being 0.01. The PCBAA hydrogel coating binding to the epoxy coated steel was cultured in zoospore suspension for 3 days. The zoospore adhesion density was determined and calculated from SEM images. PCBAA hydrogel coated epoxy on steel was free from any zoospore attachment, but bare epoxy on steel showed nearly a full coverage with zoospores, see FIGS. 17A and 17B.

FIG. 17A shows representative SEM images of ULVA zoospore adhesion on epoxy coated steel and PCBAA hydrogel coated epoxy on steel after 3 days of co-culture with ULVA zoospore at shaking condition; FIG. 17B is a graph showing calculated ULVA zoospore density on epoxy on steel and PCBAA hydrogel coated epoxy on steel. All data are presented as mean of biological replicates (n=6) ±standard deviation. Statistical analysis: unpaired two-tailed t-test, ***: $p<0.0001$. scale bar=5 μm.

Anti Marine Fouling Test of the Zwitterionic PCBAA-Polyacrylamide Hydrogel Binding Composition The Zwitterionic PCBAA-Polyacrylamide Hydrogel Binding Composition (Binding Composition 6) Resisted ULVA Zoospores The ULVA algae were purchased from Carolina Biology Supply and shipped directly from the Atlantic Ocean in Maine. Soon upon arrival, the algae were washed thoroughly with sterile seawater to remove the unwanted marine plant and creatures. The algae were then transferred to a conical flask with Algae Gro culture media on a shaker at 16 h light/8 h dark cycle. Two days after culture, the culture media was collected and filtered with 20 μm membrane. The ULVA zoospores were concentrated by ultrafiltration with 1000 kDa cutoff Mw membranes at 1500 rpm for 3 min. Zoospore concentration of $8 \times 10^6$ cell/mL had been determined by OD-600 value being 0.01. Concentrated Ulva zoospore suspension ($10^6$/ml) was cultured with the unprotected epoxy coated steel, and the epoxy coated steel with zwitterionic PCBAA-polyacrylamide hydrogel binding composition (Binding composition 6) applied. After 12 h and 7-day culture, the adhesion of Ulva zoospores was determined by SEM imaging. Results (see FIGS. 18A and 18B) showed that the Ulva zoospores accumulated greatly on the epoxy painted surface (23.65±8.43 per 400 μm² for 12 h, 44.87±10.17 per 400 μm² for 7 days). The zwitterionic PCBAA-polyacrylamide hydrogel coating can greatly reduce the zoospore adhesion as compared to the commonly used epoxy surface (1.14±3.21 per 400 μm² for 12 h, 3.94±3.27 per 400 μm² for 7 days) (FIG. 18B).

Figure 18A:
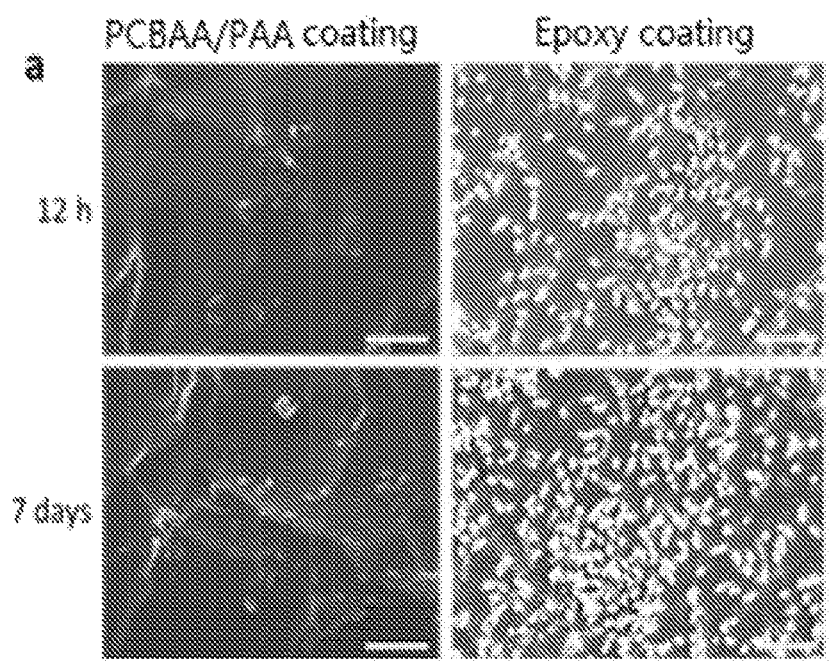
FIG. 18A shows representative SEM images of zwitterionic PCBAA-polyacrylamide hydrogel coating on the epoxy painted steel and un-protected epoxy painted steel after 12 h and 7 days culture in Ulva zoospores suspension.
Figure 18B:
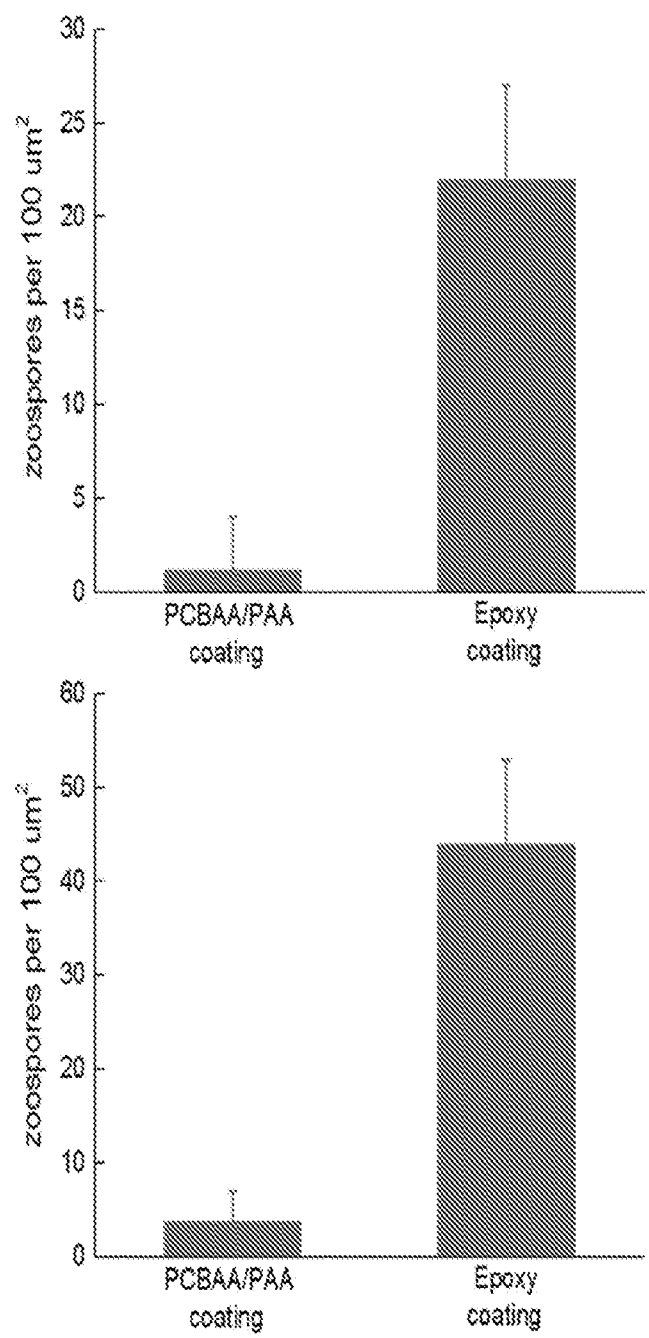
FIG. 18B is a graph showing calculated density of zoospores.

FIG. 18A shows representative SEM images of zwitterionic PCBAA-polyacrylamide hydrogel coating on the epoxy painted steel and un-protected epoxy painted steel after 12 h and 7 days culture in Ulva zoospores suspension and FIG. 18B is a graph showing calculated density of zoospores.

Figure 19A:
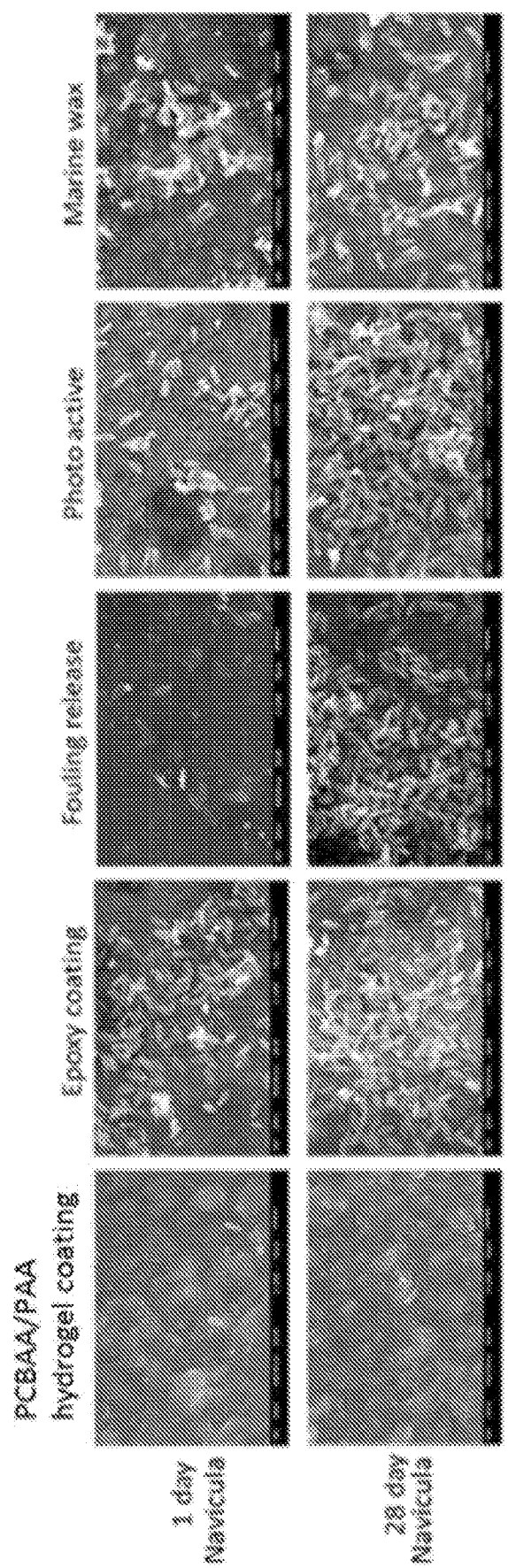
FIG. 19A shows representative SEM images of PCBAA-polyacrylamide (PCBAA-PAA) hydrogel coating and commercial marine coating references after 24 h and 28 days culture in Navicula suspension.
Figure 19B:
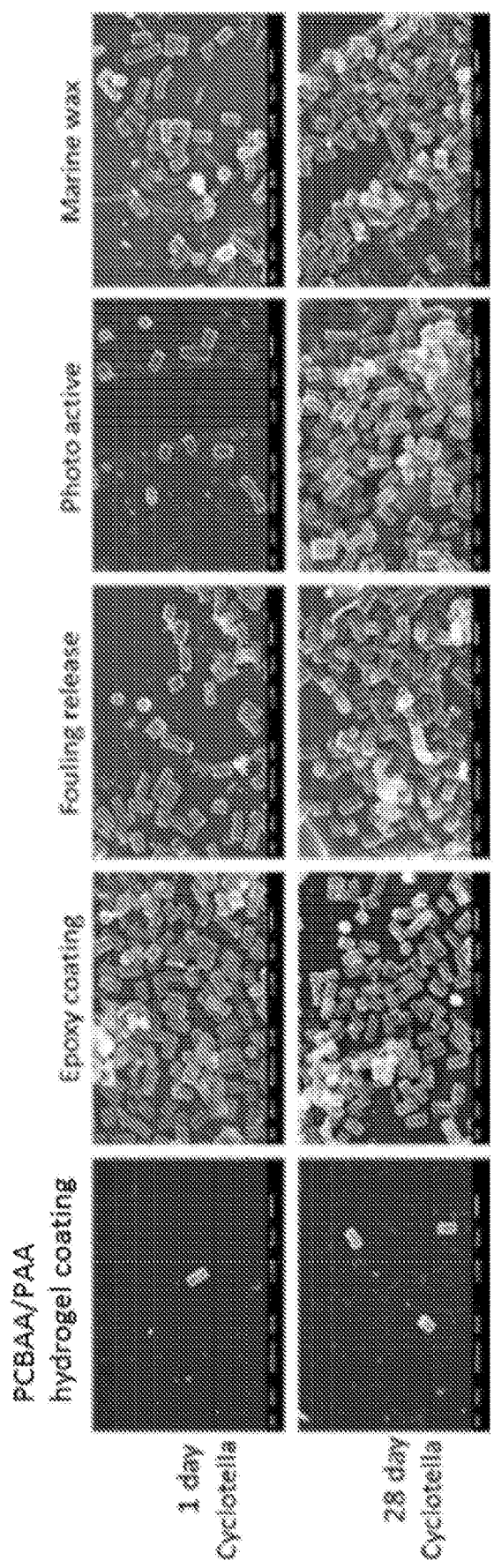
FIG. 19B shows shows representative SEM images of PCBAA-polyacrylamide (PCBAA-PAA) hydrogel coating and commercial marine coating references after 24 h and 28 days culture in Cyclotella suspension.
Figure 19C:
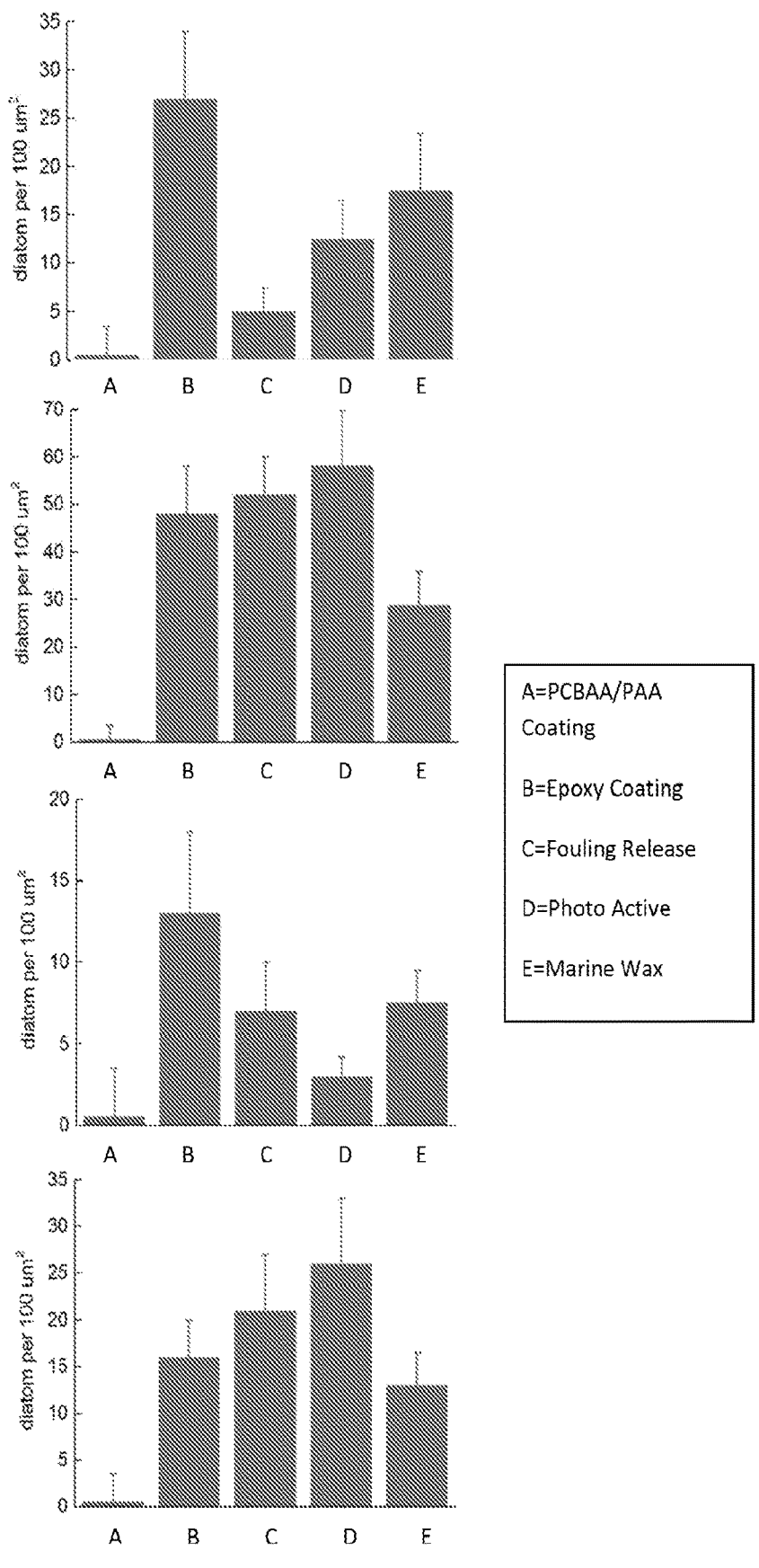
FIG. 19C is a graph showing calculated density of adhered diatoms.

The Zwitterionic PCBAA-Polyacrylamide Hydrogel Binding Composition (Binding Composition 6) Resisted Diatoms Adhesion The diatom-resistant ability of the zwitterionic PCBAA-polyacrylamide hydrogel binding composition was determined by both freshwater diatoms Navicula and sea diatoms Cyclotella, using different commercial marine anti-fouling coatings as controls, including epoxy coating (Blue water two part bottom epoxy), fouling release coating (Propglide fouling release paint), photo active coating (ePaint EP-21), marine wax coating (flagship premium marine wax). All commercial coatings other than the epoxy coating were applied on the epoxy coated steel substrate following manufactures' manuals. The diatom Navicula and Cyclotella were purchased from Carolina Biology Supply. The diatom cells were cultured in F/2 media in a conical flask. The suspension of cells will be diluted with F/2 medium to give a cell suspension with a chlorophyll content of ~0.25 μg/mL. The coating surfaces were co-cultured with diatoms suspension ($3.2 \times 10^3$/ml for Navicula and $4.0 \times 10^3$/ml for Cyclotella) for 24 h and 28 days. After culture, the substrate plate was gently washed to remove loosely bound diatom and the adhesion density will be determined and calculated from SEM images. SEM results indicated the zwitterionic PCBAA-polyacrylamide hydrogel binding composition could greatly reduce the diatoms for both short-term and long-term, see FIGS. 19A, 19B and 19C, compared to the commercial products (Fouling-release coating, photo-active coating, wax coating and epoxy coating). It should be noted that both the commercial fouling-release coating and the photo-active coating showed the short-term resistance to diatoms, but diatom biofilms grew terribly after long-term interaction with these coatings.

Representative SEM images of PCBAA-polyacrylamide (PCBAA-PAA) hydrogel coating and commercial marine coating references after 24 h and 28 days culture in FIG. 19A, Navicula suspension, and FIG. 19B, Cyclotella suspension, and FIG. 19C is a graph showing calculated density of adhered diatoms.

The Zwitterionic PCBAA-Polyacrylamide Hydrogel Binding Composition (Binding Composition 6) Resisted Macro-Organisms, e.g., Mussels.

Live Canadian mussels were obtained from the local vendor and were randomly placed on the testing substrate plates made of carbon steel with epoxy coating (Blue water two part bottom epoxy), copper self-polish coating (SPC; interlux Micron CSC), fouling-release coating (Propglide fouling release paint) and the zwitterionic PCBAA-polyacrylamide hydrogel binding composition (Binding composition 6) coating, see FIG. 20A. All commercial coatings other than epoxy coating were applied on the epoxy coated steel substrate following manufactures' manuals. After 48 h, all mussels originally on the zwitterionic PCBAA-polyacrylamide coating escaped to nearby spaces while mussels on other coatings mostly stayed, see FIG. 20B. The superior antifouling performance was observed even over the gold standard, SPCs.

The Zwitterionic PCBAA-Polyacrylamide Hydrogel Binding Composition (Binding Composition 6, 7, 8, and 9) Achieved Long-Term Stability in Field Test.

The zwitterionic PCBAA-polyacrylamide hydrogel binding composition (Binding composition 6, 7, 8, and 9) was applied to the epoxy bottom paint on carbon steel substrate and was placed in the Detroit River, which has a steady 1.3 mph flow speed during the whole year. After 4-month exposure to shear stress, the coating was stable and 100% maintained its morphology.

The Zwitterionic PCBAA-Polyacrylamide Hydrogel Binding Composition (Binding Composition 6) Achieved Anti Marine Fouling Performance in Field Test.

For anti-fouling performance field test, PCBAA-polyacrylamide hydrogel binding composition (Binding composition 6), epoxy paint (Blue water two part bottom epoxy), and fouling release coating (Propglide fouling release paint) were applied on a PVC panel and placed in the Lake St. Clair, which experienced algae bloom in 2015. After one-month exposure, PCBAA-polyacrylamide hydrogel coating was free of any fouling and even mud, while the epoxy paint and fouling-release coating were fouled with newly grown green algae and mud, see FIG. 20C.

FIG. 20A shows coating samples for the mussel preference/walking test. FIG. 20B shows results of 48 h mussel preference/walking test (top left showed the location for zwitterionic PCBAA-polyacrylamide (PCBAA/PAA) coating), and FIG. 20C shows results of a one-month exposure test in Lake St. Clair (PCBAA/PAA coating: free of fouling and mud).

Reverse Coating Examples

Preparation of Zwitterionic PCBAA Reverse Coating on PHEMA Substrate (Reverse Coating Composition 1) Using a Reverse Coating Method of the Present Invention.

Synthesis of PCBAA hydrogel: Briefly, 5 mg 2-Hydroxy-4'-(2-hydroxyethoxy)-2-Methylpropiophenone (I-2959) initiator and 30 mg N,N'-Methylenebis(acrylamide) (MBAA) crosslinker were dissolved in 10 mL deionized water. 500 mg CBAA monomer was then dissolved in 500 µL initiator/crosslinker solution to prepare a PCBAA pre-gel solution, which was transferred to between two polypropylene liners adhered to glass slides separated with a Teflon spacer (e.g., 1 mm in thickness). UV was applied for 20 minutes to crosslink and form the PCBAA hydrogel. PCBAA hydrogel obtained was tailored and placed in the bottom of a 20-mL glass vial. Alternatively, various volume of PCBAA pre-gel solution was directly transferred to the bottom of a 20-ml glass vial followed by UV application 20 min to obtain the PCBAA hydrogel with various thicknesses, such as 1 mm.

2 mg I-2959 initiator and 10 mg MBAA crosslinker were dissolved in 5 mL 2-Hydroxyethyl methacrylate (HEMA) monomer, which was vacuumed to remove dissolved oxygen. The HMEA/initiator/crosslinker solution was gently poured into the vial containing the PCBAA hydrogel on the bottom and was allowed to set for half an hour for adequate interpenetration of this solution to PCBAA hydrogel. The vial was then placed on a UV lamp (365 nm, 6 W) for 20 minutes to form the PHEMA substrate. The obtained PHEMA substrate with PCBAA reverse coating was obtained and was equilibrated in deionized water before further use and test.

Preparation of Zwitterionic PCBAA Reverse Coating on Alginate Substrate (Reverse Coating Composition 2) Using a Reverse Coating Method of the Present Invention.

PCBAA hydrogel was synthesized and placed, or synthesized on the bottom of a 20-ml glass vial according to the procedure described for Reverse coating composition 1.

The alginate solution in saline containing 1.4% Alginate SLG20 was gently poured into the vial containing the PCBAA hydrogel on the bottom and was allowed to set for 6 hours for adequate interpenetration into the PCBAA hydrogel. The vial was then filled in with 20 mM BaCl2 solution for 5, 10, 20, or 30 minutes to solidify/crosslink the alginate substrate. The obtained alginate substrate with PCBAA hydrogel reverse coating was obtained and equilibrated in deionized water before further use.

Preparation of Zwitterionic PCBAA Reverse Coating on PDMS Substrate (Reverse Coating Composition 3) Using a Reverse Coating Method of the Present Invention.

Synthesis of PCBAA-tbul hydrogel: Briefly, 5 mg 2-Hydroxy-4'-(2-hydroxyethoxy)-2-Methylpropiophenone (I-2959) initiator and 30 mg N,N'-Methylenebis(acrylamide) (MBAA) crosslinker were dissolved in 10 mL Dichloromethane (DCM). 500 mg CBAA-tBul monomer was then dissolved in 500 µL initiator/crosslinker solution to prepare a PCBAA-tBul pre-gel solution, which was transferred to between two polypropylene liners adhered to glass slides separated with a Teflon spacer (e.g., 1 mm in thickness). UV was applied for 20 minutes to crosslink and form the PCBAA-tbul hydrogel. PCBAA-tBul hydrogel obtained was tailored and placed in the bottom of a 20-mL glass vial. Alternatively, various volume of PCBAA-tBul pre-gel solution was directly transferred to the bottom of a 20-ml glass vial followed by UV application 20 min to obtain the PCBAA-tBul hydrogel with various thicknesses, such as 1 mm.

The PDMS primer solution was prepared by mixing 2 mL PDMS primer (Mw 500, OH-terminated), 1 mL tetraethyl orthosilicate (TEOS-four-armed crosslinker) and 100 µL dibutyltin dilaurate (catalyst). 1 mL, 3 mL or 6 mL of anhydrous DCM was added to the system to adjust the viscosity. The PDMS primer solution was gently poured into the vial containing the PCBAA-tBul hydrogel on the bottom and was allowed to set for half an hour for adequate interpenetration into the PCBAA-tBul hydrogel. The vial was then placed in the oven at 80° C. overnight to solidify the PDMS. The bulk PDMS material with the PCBAA-tBul hydrogel coating was removed from the vial and immersed in 100 mM sodium carbonate overnight for complete hydrolysis of the PCBAA-tBul hydrogel to obtain PCBAA hydrogel. The obtained PDMS substrate with PCBAA hydrogel reverse coating was obtained.

Preparation of Zwitterionic PCBAA Reverse Coating on Silicone Hydrogel Substrate/Contact Lens Substrate (Reverse Coating Composition 4) Using a Reverse Coating Method of the Present Invention.

PCBAA hydrogel was synthesized and placed, or synthesized on the bottom of a 20-ml glass vial according to the procedure described for Reverse coating composition 1.

2 mg I-2959 initiator and 10 mg MBAA crosslinker were dissolved in 5 mL contact lens monomer solution containing 40% Polyvinylpyrrolidone (PVP), 40% HEMA and 20% 3-[Tris(trimethylsiloxy)silyl]propyl methacrylate. The obtained contact lens pre-gel solution was vacuumed to remove dissolved oxygen. The contact lens pre-gel solution was gently poured into the vial and was allowed to set for half an hour for adequate interpenetration into the PCBAA hydrogel. The vial was then placed on a UV lamp (365 nm, 6 W) for 20 minutes to form the contact lens substrate. The obtained contact lens substrate (a silicone hydrogel) with PCBAA hydrogel reverse coating was obtained and equilibrated in deionized water before further use.

Preparation of Zwitterionic PCBAA Reverse Coating on Agarose Substrate (Reverse Coating Composition 5) Using a Reverse Coating Method of the Present Invention.

PCBAA hydrogel was synthesized and placed, or synthesized on the bottom of a 20-ml glass vial according to the procedure described for Reverse coating composition 1.

The agarose solution was prepared by dissolving the agarose powder in hot water under vigorous stirring (weight composition 0.8%). The agarose solution was kept above 50° C. and was gently poured into the vial containing the PCBAA hydrogel on the bottom and was allowed to set for half an hour at above 50° C. for adequate interpenetration into the PCBAA hydrogel. The vial was then placed in the 4° C. refrigerator for 30 minutes to solidify the agarose substrate. The obtained agarose substrate with PCBAA reverse coating was obtained and equilibrated in deionized water before further use.

Preparation of Zwitterionic PCBMA Reverse Coating on PHEMA Substrate (Reverse Coating Composition 6) Using a Reverse Coating Method of the Present Invention.

Synthesis of PCBMA hydrogel: Briefly, 5 mg 2-Hydroxy-4'-(2-hydroxyethoxy)-2-Methylpropiophenone (I-2959) initiator and 30 mg N,N'-Methylenebis(acrylamide) (MBAA) crosslinker were dissolved in 10 mL deionized water. 500 mg CBMA monomer was then dissolved in 500 μL initiator/crosslinker solution to prepare a PCBMA pre-gel solution, which was transferred to between two polypropylene liners adhered to glass slides separated with a Teflon spacer (e.g., 1 mm in thickness). UV was applied for 20 minutes to crosslink and form the PCBMA hydrogel. PCBMA hydrogel obtained was tailored and placed in the bottom of a 20-mL glass vial. Alternatively, various volume of PCBMA pre-gel solution was directly transferred to the bottom of a 20-ml glass vial followed by UV application 20 min to obtain the PCBMA hydrogel with various thicknesses, such as 1 mm.

2 mg I-2959 initiator and 10 mg MBAA crosslinker were dissolved in 5 mL HEMA monomer, which was vacuumed to remove dissolved oxygen. The HMEA/initiator/crosslinker solution was gently poured into the vial containing the PCBMA hydrogel on the bottom and was allowed to set for half an hour for adequate interpenetration of this solution to PCBMA hydrogel. The vial was then placed on a UV lamp (365 nm, 6 W) for 20 minutes to form the PHEMA substrate. The obtained PHEMA substrate with PCBMA reverse coating was obtained and was equilibrated in deionized water before further use.

Preparation of Zwitterionic PSBMA Reverse Coating on PHEMA Substrate (Reverse Coating Composition 7) Using a Reverse Coating Method of the Present Invention.

Synthesis of PSBMA hydrogel: Briefly, 5 mg 2-Hydroxy-4'-(2-hydroxyethoxy)-2-Methylpropiophenone (I-2959) initiator and 30 mg N,N-Methylenebis(acrylamide) (MBAA) crosslinker were dissolved in 10 mL deionized water. 500 mg SBMA monomer was then dissolved in 500 μL initiator/crosslinker solution to prepare a PSBMA pre-gel solution, which was transferred to between two polypropylene liners adhered to glass slides separated with a Teflon spacer (e.g., 1 mm in thickness). UV was applied for 20 minutes to crosslink and form the PSBMA hydrogel. PSBMA hydrogel obtained was tailored and placed in the bottom of a 20-mL glass vial. Alternatively, various volume of PSBMA pre-gel solution was directly transferred to the bottom of a 20-ml glass vial followed by UV application 20 min to obtain the PSBMA hydrogel with various thicknesses, such as 1 mm.

2 mg I-2959 initiator and 10 mg MBAA crosslinker were dissolved in 5 mL HEMA monomer, which was vacuumed to remove dissolved oxygen. The HMEA/initiator/crosslinker solution was gently poured into the vial containing the PSBMA hydrogel on the bottom and was allowed to set for half an hour for adequate interpenetration of this solution to PSBMA hydrogel. The vial was then placed on a UV lamp (365 nm, 6 W) for 20 minutes to form the PHEMA substrate. The obtained PHEMA substrate with PSBMA reverse coating was obtained and was equilibrated in deionized water before further use.

Preparation of Zwitterionic PMPC Reverse Coating on PHEMA Substrate (Reverse Coating Composition 8) Using a Reverse Coating Method of the Present Invention.

Synthesis of PMPC hydrogel: Briefly, 5 mg 2-Hydroxy-4'-(2-hydroxyethoxy)-2-Methylpropiophenone (I-2959) initiator and 30 mg N,N'-Methylenebis(acrylamide) (MBAA) crosslinker were dissolved in 10 mL deionized water. 500 mg MPC monomer was then dissolved in 500 μL initiator/crosslinker solution to prepare a PMPC pre-gel solution, which was transferred to between two polypropylene liners adhered to glass slides separated with a Teflon spacer (e.g., 1 mm in thickness). UV was applied for 20 minutes to crosslink and form the PMPC hydrogel. PMPC hydrogel obtained was tailored and placed in the bottom of a 20-mL glass vial. Alternatively, various volume of PMPC pre-gel solution was directly transferred to the bottom of a 20-ml glass vial followed by UV application 20 min to obtain the PMPC hydrogel with various thicknesses, such as 1 mm.

2 mg I-2959 initiator and 10 mg MBAA crosslinker were dissolved in 5 mL HEMA monomer, which was vacuumed to remove dissolved oxygen. The HMEA/initiator/crosslinker solution was gently poured into the vial containing the PMPC hydrogel on the bottom and was allowed to set for half an hour for adequate interpenetration of this solution to PMPC hydrogel. The vial was then placed on a UV lamp (365 nm, 6 W) for 20 minutes to form the PHEMA substrate. The obtained PHEMA substrate with PMPC reverse coating was obtained and was equilibrated in deionized water before further use.

Preparation of PEG Reverse Coating on PHEMA Substrate (Reverse Coating Composition 9) Using a Reverse Coating Method of the Present Invention.

Synthesis of PEGMA hydrogel: Briefly, 5 mg 2-Hydroxy-4'-(2-hydroxyethoxy)-2-Methylpropiophenone (I-2959) initiator and 30 mg N,N'-Methylenebis(acrylamide) (MBAA) crosslinker were dissolved in 10 mL deionized water. 500 mg PEGMA monomer was then dissolved in 500 L initiator/crosslinker solution to prepare a PEGMA pre-gel solution, which was transferred to between two polypropylene liners adhered to glass slides separated with a Teflon spacer (e.g., 1 mm in thickness). UV was applied for 20 minutes to crosslink and form the PEGMA hydrogel. PEGMA hydrogel obtained was tailored and placed in the bottom of a 20-mL glass vial. Alternatively, various volume of PEGMA pre-gel solution was directly transferred to the bottom of a 20-ml glass vial followed by UV application 20 min to obtain the PEGMA hydrogel with various thicknesses, such as 1 mm.

2 mg I-2959 initiator and 10 mg MBAA crosslinker were dissolved in 5 mL HEMA monomer, which was vacuumed to remove dissolved oxygen. The HMEA/initiator/crosslinker solution was gently poured into the vial containing the PEGMA hydrogel on the bottom and was allowed to set for half an hour for adequate interpenetration of this solution to PEGMA hydrogel. The vial was then placed on a UV lamp (365 nm, 6 W) for 20 minutes to form the PHEMA substrate. The obtained PHEMA substrate with PEGMA reverse coating was obtained and was equilibrated in deionized water before further use.

Preparation of PEG Reverse Coating on PDMS Substrate (Reverse Coating Composition 10) Using a Reverse Coating Method of the Present Invention.

Synthesis of PEGMA hydrogel: Briefly, 5 mg 2-Hydroxy-4'-(2-hydroxyethoxy)-2-Methylpropiophenone (I-2959) initiator and 30 mg N,N'-Methylenebis(acrylamide) (MBAA) crosslinker were dissolved in 10 mL deionized water. 500 mg PEGMA monomer was then dissolved in 500 µL initiator/crosslinker solution to prepare a PEGMA pre-gel solution, which was transferred to between two polypropylene liners adhered to glass slides separated with a Teflon spacer (e.g., 1 mm in thickness). UV was applied for 20 minutes to crosslink and form the PEGMA hydrogel. PEGMA hydrogel obtained was tailored and placed in the bottom of a 20-mL glass vial. Alternatively, various volume of PEGMA pre-gel solution was directly transferred to the bottom of a 20-ml glass vial followed by UV application 20 min to obtain the PEGMA hydrogel with various thicknesses, such as 1 mm.

The PDMS primer solution was prepared by mixing 2 mL PMDS primer (Mw 500, OH-terminated), 1 mL Tetraethyl orthosilicate (TEOS—four-armed crosslinker) and 100 uL Dibutyltin dilaurate (catalyst). 1 mL, 3 mL or 6 mL of anhydrous DCM was added to the system to adjust the viscosity. The PDMS primer solution was gently poured into the vial containing the PEGMA hydrogel on the bottom and was allowed to set for half an hour for adequate interpenetration into the PEGMA hydrogel. The vial was then placed in the oven at 80° C. overnight to solidify the PDMS. The bulk PDMS substrate with the PEGMA hydrogel coating was removed from the vial. The obtained PDMS substrate with PEGMA reverse coating was obtained and equilibrated in deionized water before further use.

Preparation of PEG Reverse Coating on Polystyrene (PS) Substrate (Reverse Composition 11) Using a Reverse Coating Method of the Present Invention.

Synthesis of PEGMA hydrogel: Briefly, 5 mg 2-Hydroxy-4'-(2-hydroxyethoxy)-2-Methylpropiophenone (I-2959) initiator and 30 mg N,N'-Methylenebis(acrylamide) (MBAA) crosslinker were dissolved in 10 mL deionized water. 500 mg PEGMA monomer was then dissolved in 500 µL initiator/crosslinker solution to prepare a PEGMA pre-gel solution, which was transferred to between two polypropylene liners adhered to glass slides separated with a Teflon spacer (e.g., 1 mm in thickness). UV was applied for 20 minutes to crosslink and form the PEGMA hydrogel. PEGMA hydrogel obtained was tailored and placed in the bottom of a 20-mL glass vial. Alternatively, various volume of PEGMA pre-gel solution was directly transferred to the bottom of a 20-ml glass vial followed by UV application 20 min to obtain the PEGMA hydrogel with various thicknesses, such as 1 mm.

The polystyrene primer was prepared by mixing 50 mg AIBN, 1 mL styrene and 100 µL divinylbenzene (crosslinker). The PS primer was gently poured into the vial containing the PEGMA hydrogel on the bottom and was allowed to set for half an hour for adequate interpenetration into the PEGMA hydrogel. The vial was then placed in the oven at 90° C. overnight to solidify the PS. The bulk PS substrate with the PEGMA hydrogel coating was removed from the vial. The obtained PS material with PEGMA hydrogel reverse coating was obtained and equilibrated in deionized water before further use.

Preparation of PNIPAAm Reverse Coating on PHEMA Substrate (Reverse Coating Composition 12) Using a Reverse Coating Method of the Present Invention.

Synthesis of PNIPAAm hydrogel: Briefly, 5 mg 2-Hydroxy-4'-(2-hydroxyethoxy)-2-Methylpropiophenone (I-2959) initiator and 30 mg N,N'-Methylenebis(acrylamide) (MBAA) crosslinker were dissolved in 10 mL deionized water. 500 mg N-Isopropylacrylamide (NIPAAm) monomer was then dissolved in 500 µL initiator/crosslinker solution to prepare a PNIPAAm pre-gel solution, which was transferred to between two polypropylene liners adhered to glass slides separated with a Teflon spacer (e.g., 1 mm in thickness). UV was applied for 20 minutes at 4° C. to crosslink and form the PNIPAAm hydrogel. PNIPAAm hydrogel obtained was tailored and placed in the bottom of a 20-mL glass vial. Alternatively, various volume of PNIPAAm pre-gel solution was directly transferred to the bottom of a 20-ml glass vial followed by UV application 20 min at 4° C. to obtain the PNIPAAm hydrogel with various thicknesses, such as 1 mm.

2 mg I-2959 initiator and 10 mg MBAA crosslinker were dissolved in 5 mL HEMA monomer, which was vacuumed to remove dissolved oxygen. The HMEA/initiator/crosslinker solution was gently poured into the vial containing the PNIPAAm hydrogel on the bottom and was allowed to set for half an hour for adequate interpenetration of this solution to PNIPAAm hydrogel. The vial was then placed on a UV lamp (365 nm, 6 W) for 20 minutes to form the PHEMA substrate. The obtained PHEMA substrate with PNIPAAm reverse coating was obtained and was equilibrated in deionized water before further use.

Preparation of PNIPAAm Reverse Coating on PS Substrate (Reverse Coating Composition 13) Using a Reverse Coating Method of the Present Invention.

Synthesis of PNIPAAm hydrogel: Briefly, 5 mg 2-Hydroxy-4'-(2-hydroxyethoxy)-2-Methylpropiophenone (I-2959) initiator and 30 mg N,N'-Methylenebis(acrylamide) (MBAA) crosslinker were dissolved in 10 mL deionized water. 500 mg NIPAAm monomer was then dissolved in 500 µL initiator/crosslinker solution to prepare a PNIPAAm pre-gel solution, which was transferred to between two polypropylene liners adhered to glass slides separated with a Teflon spacer (e.g., 1 mm in thickness). UV was applied for 20 minutes at 4° C. to crosslink and form the PNIPAAm hydrogel. PNIPAAm hydrogel obtained was tailored and placed in the bottom of a 20-mL glass vial. Alternatively, various volume of PNIPAAm pre-gel solution was directly transferred to the bottom of a 20-ml glass vial followed by UV application 20 min at 4° C. to obtain the PNIPAAm hydrogel with various thicknesses, such as 1 mm.

The polystyrene primer was prepared by mixing 50 mg AIBN, 1 mL styrene and 100 µL divinylbenzene (crosslinker). The PS primer was gently poured into the vial containing the PNIPAAm hydrogel on the bottom and was allowed to set for half an hour for adequate interpenetration into the PNIPAAm hydrogel. The vial was then placed in the oven at 90° C. overnight to solidify the PS. The bulk PS substrate with the PNIPAAm hydrogel coating was removed from the vial. The obtained PS substrate with PNIPAAm hydrogel reverse coating was obtained and equilibrated in deionized water before further use.

Preparation of Chitosan Reverse Coating on PHEMA Substrate (Reverse Coating Composition 14) Using a Reverse Coating Method of the Present Invention.

Synthesis of the chitosan hydrogel: 10 mg chitosan (deacetylated chitin, average molecular weight is 310000-375000 Da) was dissolved in 500 µl 1% HCl solution to make primer A. The primer A was mixed with 500 µl 1% Glutaric dialdehyde to make the pre-gel solution, which was transferred to between two polypropylene liners adhered to glass slides separated with a Teflon spacer (e.g., 1 mm in thickness). The pre-gel solution was allowed to set at 40° C. oven for 6 h to crosslink and obtain the chitosan hydrogel. Chitosan hydrogel obtained was tailored and placed in the bottom of a 20-mL glass vial. Alternatively, various volume of chitosan pre-gel solution was directly transferred to the bottom of a 20-ml glass vial followed by 40° C. oven for 6 h to obtain the chitosan hydrogel with various thicknesses, such as 1 mm.

2 mg I-2959 initiator and 10 mg MBAA crosslinker were dissolved in 5 mL HEMA monomer, which was vacuumed to remove dissolved oxygen. The HMEA/initiator/crosslinker solution was gently poured into the vial containing the chitosan hydrogel on the bottom and was allowed to set for half an hour for adequate interpenetration of this solution to chitosan hydrogel. The vial was then placed on a UV lamp (365 nm, 6 W) for 20 minutes to form the PHEMA substrate. The obtained PHEMA substrate with chitosan gel reverse coating was obtained and was equilibrated in deionized water before further use.

Fabrication of tubing substrates with inner wall, outer wall, or both inner and outer walls coated with the hydrogel reverse coatings using the reverse coating method. The substrate and the hydrogel coating can be any of the various materials as described herein. The obtained hydrogel reverse coating on tubing materials can be used for various blood or tissue contacting applications, including artificial blood vessels, catheters, infusion and dialysis devices.

Preparation of PHEMA Tubing Substrate with Inner Wall Coated with Zwitterionic PCBAA Hydrogel Reverse Coating (Reverse Coating Composition 15) Using a Reverse Coating Method of the Present Invention.

Synthesis of the PCBAA hydrogel. 5 mg Ammonium persulfate (APS) initiator and 30 mg N,N'-Methylenebis-(acrylamide) (MBAA) crosslinker were dissolved in 10 ml DI water. 300 mg zwitterionic CBAA monomer was then dissolved in 300 µl initiator/crosslinker solution to prepare a pre-gel solution. The pre-gel solution was poured into a mold (the mold could be made of plastic, metal or ceramics) having a cylindrical cavity with certain diameters (e.g., 4 mm) and the mold containing the pre-gel solution was placed in an oven for 1 h at 60° C. The formed cylindrical zwitterionic PCBAA hydrogel was removed from the mold and was then transferred to another mold having a cylindrical cavity with larger diameters (e.g., 6 mm). The cylindrical PCBAA hydrogel was fixed inside of the cylindrical cavity (e.g., the hydrogel cylinder can be aligned with its axis overlay with the one of the cylindrical cavity).

Synthesis of the PHEMA tubing substrate. 2 mg azobisisobutyronitrile (AIBN) initiator and 10 mg MBAA crosslinker were dissolved in 5 ml HEMA monomer, which was vacuumed to remove dissolved oxygen. The HEMA/initiator liquid was poured into the cavity of the mold containing the PCBAA hydrogel to fill the remaining space. The mold was placed at 80° C. oven overnight and the solidified PHEMA tube material was removed from the mold and equilibrated in sterile PBS buffer. Partial volume of PCBAA hydrogel (located at the center of the tube) was removed and the formed inner wall coating was intensively washed with PBS buffer to completely remove PCBAA hydrogel debris. The obtained PHEMA tube with PCBAA hydrogel reverse coating on the inner wall can be further tailored to obtain desirable length and was stored in sterile PBS for further use.

Preparation of PHEMA Tubing Substrate with Inner Wall Coated with PEG Hydrogel Reverse Coating (Reverse Coating Composition 16) Using a Reverse Coating Method of the Present Invention.

Synthesis of the PEGMA hydrogel. 5 mg Ammonium persulfate (APS) initiator and 30 mg N,N'-Methylenebis-(acrylamide) (MBAA) crosslinker were dissolved in 10 ml DI water. 200 µl Poly(ethylene glycol) methacrylate (PEGMA, Mn 500) monomer was then mixed with 200 µl initiator/crosslinker solution to prepare a pre-gel solution. The pre-gel solution was poured into a mold (the mold could be made of plastic, metal or ceramics) having a cylindrical cavity with certain diameters (e.g., 4 mm) and the mold containing the pre-gel solution was placed in an oven for 1 h at 60° C. The formed cylindrical PEG hydrogel was removed from the mold and was then transferred to another mold having a cylindrical cavity with larger diameters (e.g., 6 mm). The cylindrical PEG hydrogel was fixed inside of the cylindrical cavity (e.g., the hydrogel cylinder can be aligned with its axis overlay with the one of the cylindrical cavity).

Synthesis of the PHEMA tubing substrate. 2 mg azobisisobutyronitrile (AIBN) initiator and 10 mg MBAA crosslinker were dissolved in 5 ml HEMA monomer, which was vacuumed to remove dissolved oxygen. The HEMA/initiator liquid was poured into the cavity of the mold containing the PEGMA cylindrical hydrogel to fill the remaining space. The mold was placed at 80° C. oven overnight and the solidified PHEMA tube material was removed from the mold and equilibrated in sterile PBS buffer. Partial volume of PEGMA hydrogel (located at the center of the tube) was removed and the formed inner wall coating was intensively washed with PBS buffer to completely remove PEGMA hydrogel debris. The obtained PHEMA tube with PEGMA hydrogel reverse coating on the inner wall can be further tailored to obtain desirable length and was stored in sterile PBS for further use.

Preparation of PHEMA Tubing Substrate with Outer Wall Coated with Zwitterionic PCBAA Hydrogel Reverse Coating (Reverse Coating Composition 17) Using a Reverse Coating Method of the Present Invention.

Synthesis of the PCBAA hydrogel. 5 mg Ammonium persulfate (APS) initiator and 30 mg N,N'-Methylenebis-(acrylamide) (MBAA) crosslinker were dissolved in 10 ml DI water. 300 mg zwitterionic CBAA monomer was then dissolved in 300 µl initiator/crosslinker solution to prepare a pre-gel solution. The pre-gel solution was poured into a mold (the mold could be made of plastic, metal or ceramics) having a cylindrical cavity with certain diameters (e.g., 8 mm) and a solid cylindrical mold (can be made of plastic, metal or ceramics) with certain smaller diameters (e.g., 6 mm) with the axis for the cylindrical cavity and the solid cylinder overlaid. The mold containing the pre-gel solution was placed in an oven for 1 h at 60° C. The formed cylindrical zwitterionic PCBAA hydrogel will stay in the mold but the solid cylindrical mold (inside of the hydrogel) will be removed and replaced with a solid cylindrical mold with smaller diameter (e.g., 4 mm) but the axis remained to be overlaid with the one of the cylindrical cavity.

Synthesis of the PHEMA tubing substrate. 2 mg azobisisobutyronitrile (AIBN) initiator and 10 mg MBAA crosslinker were dissolved in 5 ml HEMA monomer, which was vacuumed to remove dissolved oxygen. The HEMA/initiator liquid was poured into the cavity between the PCBAA hydrogel and the solid cylindrical mold to fill the remaining space. The mold was placed at 80° C. oven overnight and the solidified PHEMA tube material with outer surface coated with PCBAA hydrogel was removed from the mold and equilibrated in sterile PBS buffer. Partial volume of PCBAA hydrogel (located at the outer surface of the tube) can be optionally removed and polished, and the formed outer wall coating was intensively washed with PBS buffer to completely remove PCBAA hydrogel debris. The obtained PHEMA tube with PCBAA hydrogel coated on the outer wall can be further tailored to obtain desirable length and was stored in sterile PBS for further use.

Preparation of PHEMA Tubing Substrate with Outer Wall Coated with PEG Hydrogel Reverse Coating (Reverse Coating Composition 18) Using a Reverse Coating Method of the Present Invention.

Synthesis of the PEGMA hydrogel. 5 mg Ammonium persulfate (APS) initiator and 30 mg N,N'-Methylenebis-(acrylamide) (MBAA) crosslinker were dissolved in 10 ml DI water. 200 µl Poly(ethylene glycol) methacrylate (PEGMA, Mn 500) monomer was then mixed with 200 µl initiator/crosslinker solution to prepare a pre-gel solution. The pre-gel solution was poured into a mold (the mold could be made of plastic, metal or ceramics) having a cylindrical cavity with certain diameters (e.g., 8 mm) and a solid cylindrical mold (can be made of plastic, metal or ceramics) with certain smaller diameters (e.g., 6 mm) with the axis for the cylindrical cavity and the solid cylinder overlaid. The mold containing the pre-gel solution was placed in an oven for 1 h at 60° C. The formed cylindrical PEG hydrogel will stay in the mold but the solid cylindrical mold (inside of the hydrogel) will be removed and replaced with a solid cylindrical mold with smaller diameter (e.g., 4 mm) but the axis remained to be overlaid with the one of the cylindrical cavity.

Synthesis of the PHEMA tubing substrate. 2 mg azobisisobutyronitrile (AIBN) initiator and 10 mg MBAA crosslinker were dissolved in 5 ml HEMA monomer, which was vacuumed to remove dissolved oxygen. The HEMA/initiator liquid was poured into the cavity between the PEGMA hydrogel and the solid cylindrical mold to fill the remaining space. The mold was placed at 80° C. oven overnight and the solidified PHEMA tube material with outer surface coated with PEG hydrogel was removed from the mold and equilibrated in sterile PBS buffer. Partial volume of PEG hydrogel (located at the outer surface of the tube) can be optionally removed and polished, and the formed outer wall coating was intensively washed with PBS buffer to completely remove PEG hydrogel debris. The obtained PHEMA tube with PEG hydrogel reverse coating on the outer wall can be further tailored to obtain desirable length and was stored in sterile PBS for further use.

Preparation of PHEMA Tubing Substrate with Both Inner and Outer Wall Coated with Zwitterionic PCBAA Hydrogel Reverse Coating (Reverse Coating Composition 19) Using a Reverse Coating Method of the Present Invention.

Synthesis of the inner PCBAA hydrogel part A. 5 mg Ammonium persulfate (APS) initiator and 30 mg N,N'-Methylenebis-(acrylamide) (MBAA) crosslinker were dissolved in 10 ml DI water. 300 mg zwitterionic CBAA monomer was then dissolved in 300 µl initiator/crosslinker solution to prepare a pre-gel solution. The pre-gel solution was poured into a mold (the mold could be made of plastic, metal or ceramics) having a cylindrical cavity with certain diameters (e.g., 4 mm) and the mold containing the pre-gel solution was placed in an oven for 1 h at 60° C. The formed cylindrical zwitterionic PCBAA hydrogel was removed from the mold and was termed inner hydrogel part A.

Synthesis of the outer PCBAA hydrogel part B. 5 mg Ammonium persulfate (APS) initiator and 30 mg N,N'-Methylenebis-(acrylamide) (MBAA) crosslinker were dissolved in 10 ml DI water. 300 mg zwitterionic CBAA monomer was then dissolved in 300 µl initiator/crosslinker solution to prepare a pre-gel solution. The pre-gel solution was poured into a mold (the mold could be made of plastic, metal or ceramics) having a cylindrical cavity with certain diameters (e.g., 8 mm) and a solid cylindrical mold (can be made of plastic, metal or ceramics) with certain smaller diameters (e.g., 6 mm) with the axis for the cylindrical cavity and the solid cylinder overlaid. The mold containing the pre-gel solution was placed in an oven for 1 h at 60° C. The formed cylindrical zwitterionic PCBAA hydrogel stayed in the mold and was termed outer hydrogel part B. The solid cylindrical mold (inside of the hydrogel part B) was removed and replaced with the inner hydrogel part A with smaller diameter (e.g., 4 mm) but the axis remained to be overlaid with the one of the cylindrical cavity.

Synthesis of the PHEMA tubing substrate. 2 mg azobisisobutyronitrile (AIBN) initiator and 10 mg MBAA crosslinker were dissolved in 5 ml HEMA monomer, which was vacuumed to remove dissolved oxygen. The HEMA/initiator liquid was poured into the cavity between the inner PCBAA hydrogel part A and the outer PCBAA hydrogel part B to fill the remaining space. The mold was placed at 80° C. oven overnight and the solidified PHEMA tube material with both inner and outer surface coated with PCBAA hydrogel was removed from the mold and equilibrated in sterile PBS buffer. Partial volume of PCBAA hydrogel part A and B (located at the inner and outer surface of the tube, respectively) can be optionally removed and polished, and the formed inner and outer wall coating was intensively washed with PBS buffer to completely remove PCBAA hydrogel debris. The obtained PHEMA tube with PCBAA hydrogel reverse coating on both inner and outer walls can be further tailored to obtain desirable length and was stored in sterile PBS for further use.

Preparation of PHEMA Tubing Substrate with Both Inner and Outer Wall Coated with PEG Hydrogel Reverse Coating (Reverse Coating Composition 20) Using a Reverse Coating Method of the Present Invention.

Synthesis of the inner PEG hydrogel part A. 5 mg Ammonium persulfate (APS) initiator and 30 mg N,N'-Methylenebis-(acrylamide) (MBAA) crosslinker were dissolved in 10 ml DI water. 200 µl Poly(ethylene glycol) methacrylate (PEGMA, Mn 500) monomer was then mixed with 200 µl initiator/crosslinker solution to prepare a pre-gel solution. The pre-gel solution was poured into a mold (the mold could be made of plastic, metal or ceramics) having a cylindrical cavity with certain diameters (e.g., 4 mm) and the mold containing the pre-gel solution was placed in an oven for 1 h at 60° C. The formed cylindrical PEG hydrogel was removed from the mold and was termed inner hydrogel part A.

Synthesis of the outer PEG hydrogel part B. 5 mg Ammonium persulfate (APS) initiator and 30 mg N,N'-Methylenebis-(acrylamide) (MBAA) crosslinker were dissolved in 10 ml DI water. 200 µl Poly(ethylene glycol) methacrylate (PEGMA, Mn 500) monomer was then mixed with 200 µl initiator/crosslinker solution to prepare a pre-gel solution. The pre-gel solution was poured into a mold (the mold could be made of plastic, metal or ceramics) having a cylindrical cavity with certain diameters (e.g., 8 mm) and a solid cylindrical mold (can be made of plastic, metal or ceramics) with certain smaller diameters (e.g., 6 mm) with the axis for the cylindrical cavity and the solid cylinder overlaid. The mold containing the pre-gel solution was placed in an oven for 1 h at 60° C. The formed cylindrical PEG hydrogel stayed in the mold and was termed outer hydrogel part B. The solid cylindrical mold (inside of the hydrogel part B) was removed and replaced with the inner hydrogel part A with smaller diameter (e.g., 4 mm) but the axis remained to be overlaid with the one of the cylindrical cavity.

Synthesis of the PHEMA tubing substrate. 2 mg azobisisobutyronitrile (AIBN) initiator and 10 mg MBAA crosslinker were dissolved in 5 ml HEMA monomer, which was vacuumed to remove dissolved oxygen. The HEMA/initiator liquid was poured into the cavity between the inner PEG hydrogel part A and the outer PEG hydrogel part B to fill the remaining space. The mold was placed at 80° C. oven overnight and the solidified PHEMA tube material with both inner and outer surface coated with PEG hydrogel was removed from the mold and equilibrated in sterile PBS buffer. Partial volume of PEG hydrogel part A and B (located at the inner and outer surface of the tube, respectively) can be optionally removed and polished, and the formed inner and outer wall coating was intensively washed with PBS buffer to completely remove PEG hydrogel debris. The obtained PHEMA tube with PEG hydrogel revere coating on both inner and outer walls can be further tailored to obtain desirable length and was stored in sterile PBS for further use.

Preparation of PHEMA Tubing Substrate with Inner and/or Outer Wall Coated with Different Types of Hydrogel Reverse Coatings Using a Reverse Coating Method of the Present Invention.

Referring to the preparation examples stated above, preparing PHEMA tubing substrates with inner and/or outer surface coated with different types of hydrogel reverse coating (e.g., PCBMA, PSBMA, PMPC, PNIPAAm, chitosan, etc.) can be conducted in similar ways by preparing inner hydrogel part A and/or outer hydrogel part B using different types of hydrogel coating materials, and PHEMA tubing substrate.

Preparation of Alginate Tubing Substrate with Inner and/or Outer Wall Coated with Different Types of Hydrogel Reverse Coatings Using a Reverse Coating Method of the Present Invention.

Referring to the preparation examples stated above, preparing alginate tubing substrates with inner and/or outer surface coated with different types of hydrogel reverse coating (e.g., PCBAA, PCBMA, PSBMA, PMPC, PEG, PNIPAAm, chitosan, etc.) can be conducted in similar ways by preparing inner hydrogel part A and/or outer hydrogel part B using different types of hydrogel coating materials, and alginate substrate.

Preparation of Agarose Tubing Substrate with Inner and/or Outer Wall Coated with Different Types of Hydrogel Reverse Coatings Using a Reverse Coating Method of the Present Invention.

Referring to the preparation examples stated above, preparing agarose tubing substrates with inner and/or outer surface coated with different types of hydrogel reverse coating (e.g., PCBAA, PCBMA, PSBMA, PMPC, PEG, PNIPAAm, chitosan, etc.) can be conducted in similar ways by preparing inner hydrogel part A and/or outer hydrogel part B using different types of hydrogel coating materials, and agarose substrate.

Preparation of PDMS Tubing Substrate with Inner and/or Outer Wall Coated with Different Types of Hydrogel Reverse Coatings Using a Reverse Coating Method of the Present Invention.

Referring to the preparation examples stated above, preparing PDMS tubing substrates with inner and/or outer surface coated with different types of hydrogel reverse coating (e.g., PCBAA, PCBMA, PSBMA, PMPC, PEG, PNIPAAm, chitosan, etc.) can be conducted in similar ways by preparing inner hydrogel part A and/or outer hydrogel part B using different types of hydrogel coating materials, and PDMS substrate.

Preparation of Silicone Hydrogel Tubing Substrate with Inner and/or Outer Wall Coated with Different Types of Hydrogel Reverse Coatings Using a Reverse Coating Method of the Present Invention.

Referring to the preparation examples stated above, preparing silicone hydrogel tubing substrates with inner and/or outer surface coated with different types of hydrogel reverse coating (e.g., PCBAA, PCBMA, PSBMA, PMPC, PEG, PNIPAAm, chitosan, etc.) can be conducted in similar ways by preparing inner hydrogel part A and/or outer hydrogel part B using different types of hydrogel coating materials, and silicone hydrogel substrate.

Preparation of PS Tubing Substrate with Inner and/or Outer Wall Coated with Different Types of Hydrogel Reverse Coatings Using a Reverse Coating Method of the Present Invention.

Referring to the preparation examples stated above, preparing PS tubing substrates with inner and/or outer surface coated with different types of hydrogel reverse coating (e.g., PCBAA, PCBMA, PSBMA, PMPC, PEG, PNIPAAm, chitosan, etc.) can be conducted in similar ways by preparing inner hydrogel part A and/or outer hydrogel part B using different types of hydrogel coating materials, and PS substrate.

Durability and antifouling performance test on the zwitterionic PCBAA reverse coating on PHEMA substrate (Reverse coating composition 1).

The zwitterionic PCBAA reverse coating on PHEMA substrate (Reverse coating composition 1) was incubated in DI water at room temperature for up to two months. The morphology of the coating was almost unchanged, and the antifouling property (tested by human fibrinogen binding followed by enzyme-linked immunosorbent assay (ELISA) quantification of the absorbed protein) was retained at the same level as freshly made coatings after the long-term incubation, see FIG. 21A. The coating was further examined under various durability tests in aqueous environment, including (1) exposed to phosphate buffered saline (PBS) shearing (1500 rpm, 202 G) at room temperature for 30 d, see FIG. 21B, (2) subjected to continuous perpendicular water-flush at a flow rate of 42.8 ml. s.1 for 30 d, see FIG. 21C. These challenging conditions did not change the morphology of the coating, and the antifouling property of the coating was well retained, indicated by the unchanged, significantly lowered human fibrinogen absorption on the coating, compared with uncoated PHEMA substrate.

Figure 21A:
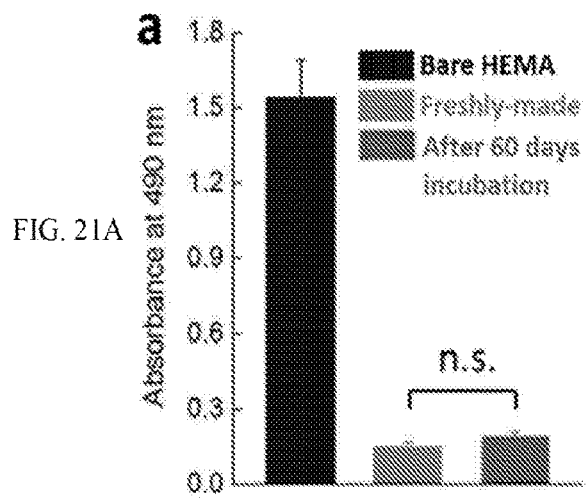
FIG. 21A is a graph showing antifouling property of the zwitterionic PCBAA reverse coating on PHEMA substrate after 60 d incubation in water at room temperature; bare PHEMA substrate was used as control.
Figure 21B:
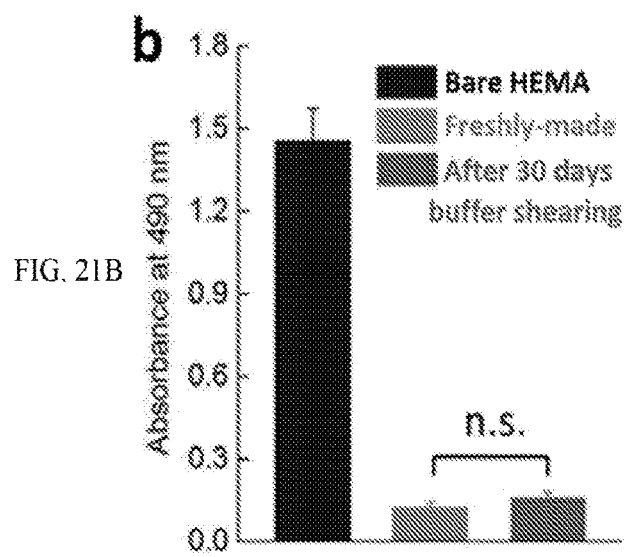
FIG. 21B is a graph showing antifouling property of the zwitterionic PCBAA reverse coating on PHEMA substrate after 30 d exposure to PBS shearing at room temperature; bare PHEMA substrate was used as control.
Figure 21C:
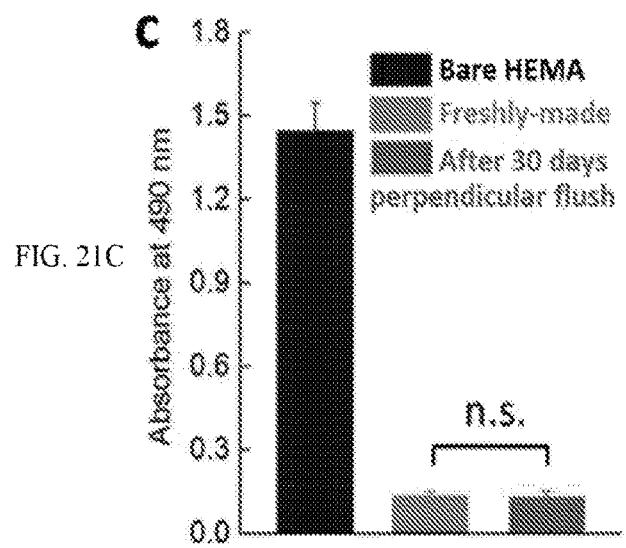
FIG. 21C is a graph showing antifouling property of the zwitterionic PCBAA reverse coating on PHEMA substrate after 30 d exposure to perpendicular water flush; bare PHEMA substrate was used as control.

FIGS. 21A, 21B and 21C: Antifouling property of the zwitterionic PCBAA reverse coating on PHEMA substrate after various durability tests. Bare PHEMA substrate was used as control. FIG. 21A is a graph showing results after 60 d incubation in water at room temperature; FIG. 21B is a graph showing results after 30 d exposure to PBS shearing at room temperature; FIG. 21C is a graph showing results after 30 d exposure to perpendicular water flush. The antifouling property was evaluated by the resistance of human fibrinogen binding on the surface (absorbed protein) before and after the coating being challenged. All data are presented as mean of replicates (n=3)±standard deviation. Statistical analysis: unpaired, two-tailed t-test, n.s.: no significant difference at $P>0.05$, meaning the great antifouling property was retained through the stability challenge.

*Escherichia coli* (*E. coli*, gram-negative), *Staphylococcus aureus* (*s. aureus*, gram-positive) and *Candida albicans* (*C. albicans*, fungus) were used as model systems to incubate with the zwitterionic PCBAA reverse coating on PHEMA substrate (Reverse coating composition 1). The coating's resistance to bacterial adhesion and biofilm formation was evaluated and quantified by SEM. The coating was challenged with dynamic bacterial culture condition.

The reverse coating with the substrate and the uncoated PHEMA substrate was placed in bacterial culture medium (Luria-Bertani (LB) broth for *E. coli*; Tryptic Soy (TS) broth for *S. aureus*; Yeast Mold (YM) broth for *C. albicans*) containing an extremely high number of bacteria ($1.05 \times 10^9$ cells/mL) at 37° C. for 30 d under continuous shaking (300 rpm). The culture medium was gently refreshed every 2 d, and the bacterial density within the refreshed medium was kept at $1.05 \times 10^9$ cells/mL. After 30 d, bacteria on the substrate surface were fixed, dehydrated, vacuumed, and visualized under SEM. Results indicated almost zero adhesion of bacteria on the PCBAA reverse coating on the PHEMA substrate, while biofilm had developed on the uncoated PHEMA surface for all three types of bacteria, see FIGS. 22A, 22B and 22C.

Figures 22A, 22B, 22C:
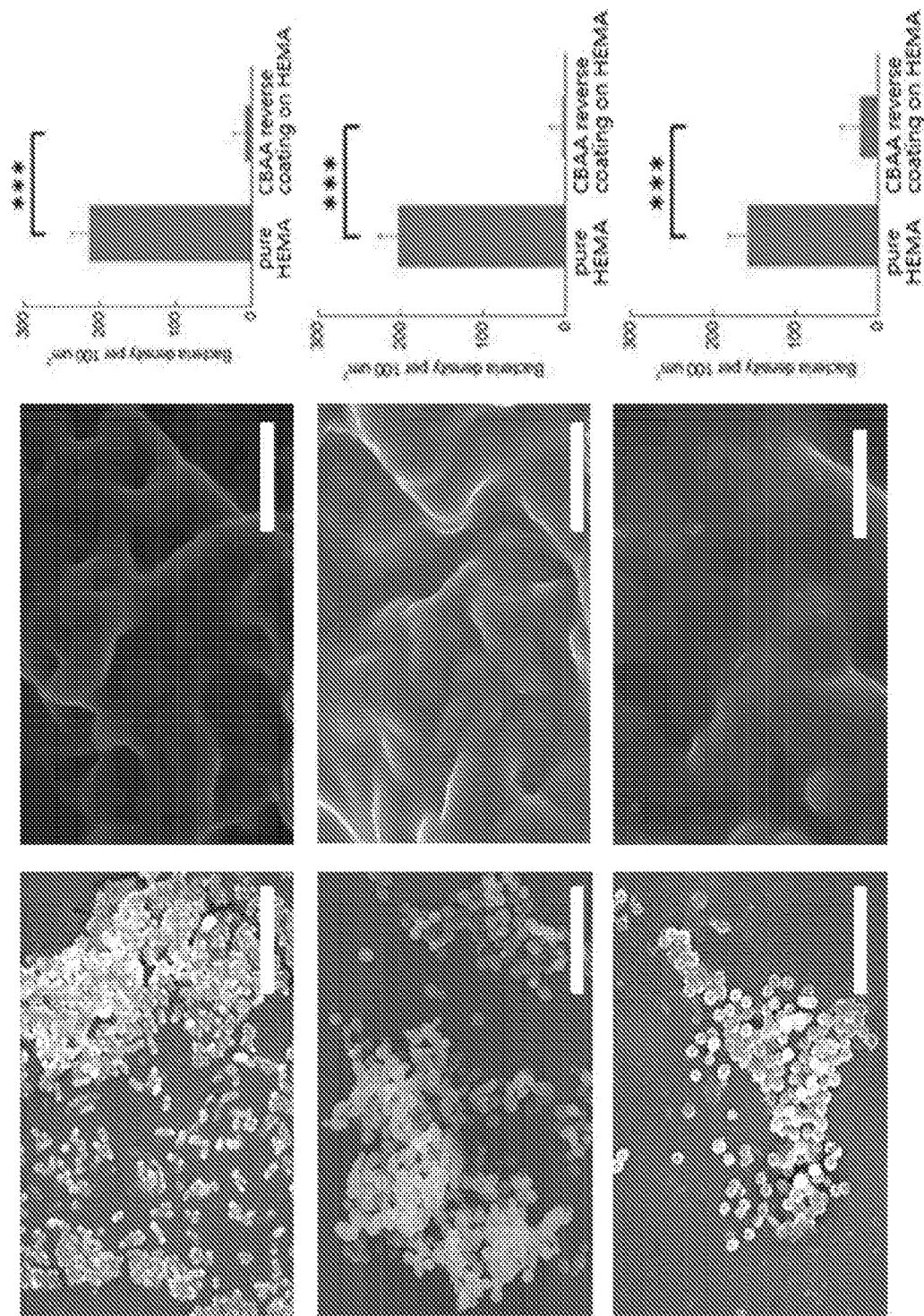
FIG. 22A shows representative SEM images of *E. coli* bacteria on uncoated PHEMA substrate, and PCBAA reverse coating on PHEMA substrate after 30 days of co-culture under the shaking condition with concentrated microbes and a graph showing calculated microbe adhesion density; all data are presented as mean of biological replicates (n=6)±standard deviation. Statistical analysis: one-way analysis of variance (ANOVA) with Bonferroni multi-comparison. ***: p<0.0001. Scale bar=10 μm.
FIG. 22B shows representative SEM images of *S. aureus* bacteria on uncoated PHEMA substrate, and PCBAA reverse coating on PHEMA substrate after 30 days of co-culture under the shaking condition with concentrated microbes and a graph showing calculated microbe adhesion density; all data are presented as mean of biological replicates (n=6)±standard deviation. Statistical analysis: one-way analysis of variance (ANOVA) with Bonferroni multi-comparison. ***: p<0.0001. Scale bar=10 μm.
FIG. 22C shows representative SEM images of *C. albicans* fungus on uncoated PHEMA substrate, and PCBAA reverse coating on PHEMA substrate after 30 days of co-culture under the shaking condition with concentrated microbes and a graph showing calculated microbe adhesion density; all data are presented as mean of biological replicates (n=6)±standard deviation. Statistical analysis: one-way analysis of variance (ANOVA) with Bonferroni multi-comparison. ***: p<0.0001. Scale bar=10 μm.

Representative SEM images of bacteria and fungi adhesion on uncoated PHEMA substrate, and PCBAA reverse coating on PHEMA substrate after 30 d of co-culture under the shaking condition with concentrated microbes and calculated microbe adhesion density for (a) *E. coli* bacteria, FIG. 22A; (b) *S. aureus* bacteria, FIG. 22B and (c) *C. albicans* fungus, FIG. 22C. All data are presented as mean of biological replicates (n=6)±standard deviation. Statistical analysis: one-way analysis of variance (ANOVA) with Bonferroni multicomparison. ***: $p<0.0001$. Scale bar=10 μm.

Preparation of Zwitterionic PCBAA Reverse Coating on Poly(Trimesoyl Chloride-Co-Piperazine) Membrane Substrate (Reverse Coating Composition 21) Using a Reverse Coating Method of the Present Invention.

Synthesis of PCBAA hydrogel: Briefly, 5 mg 2-Hydroxy-4'-(2-hydroxyethoxy)-2-Methylpropiophenone (I-2959) initiator and 30 mg N,N'-Methylenebis(acrylamide) (MBAA) crosslinker were dissolved in 10 mL deionized water. 500 mg CBAA monomer was then dissolved in 500 μL initiator/crosslinker solution to prepare a PCBAA pre-gel solution, which was transferred to between two polypropylene liners adhered to glass slides separated with a Teflon spacer (e.g., 1 mm in thickness). UV was applied for 20 minutes to crosslink and form the PCBAA hydrogel. PCBAA hydrogel obtained was tailored and placed in the bottom of a 20-mL glass vial. Alternatively, various volume of PCBAA pre-gel solution was directly transferred to the bottom of a 20-ml glass vial followed by UV application 20 min to obtain the PCBAA hydrogel with various thicknesses, such as 1 mm.

Piperazine and trimethylamine were dissolved in water to reach the same concentration such as 0.025%. This solution was gently poured into the vial containing the PCBAA hydrogel on the bottom and was allowed to set for 10 min for adequate interpenetration of this solution to PCBAA hydrogel. After that, excess amount of the solution was removed and the surface of PCBAA hydrogel exposed was allowed to air-dry for various time points from 1 min to 1 hour. Then 0.02% (w/v) of trimesoyl chloride in hexane was introduced to the exposed surface of PCBAA hydrogel to allow the interfacial polymerization for 30 second to 10 min, followed by rinsing with hexane, drying at 60° C. for 30 min, and equilibrium in water before further use.

Preparation of Zwitterionic PCBAA Reverse Coating Poly(Trimesoyl Chloride-Co-m-Phenylenediamine) Membrane Substrate (Reverse Coating Composition 22) Using a Reverse Coating Method of the Present Invention.

Synthesis of PCBAA hydrogel: Briefly, 5 mg 2-Hydroxy-4'-(2-hydroxyethoxy)-2-Methylpropiophenone (I-2959) initiator and 30 mg N,N'-Methylenebis(acrylamide) (MBAA) crosslinker will be dissolved in 10 mL deionized water. 500 mg CBAA monomer will then be dissolved in 500 μL initiator/crosslinker solution to prepare a PCBAA pre-gel solution, which will be transferred to between two polypropylene liners adhered to glass slides separated with a Teflon spacer (e.g., 1 mm in thickness). UV will be applied for 20 minutes to crosslink and form the PCBAA hydrogel. PCBAA hydrogel obtained will be tailored and placed in the bottom of a 20-mL glass vial. Alternatively, various volumes of PCBAA pre-gel solution will be directly transferred to the bottom of a 20-ml glass vial followed by UV application 20 min to obtain the PCBAA hydrogel with various thicknesses, such as 1 mm.

m-phenylenediamine and trimethylamine will be dissolved in water to reach the same concentration such as 0.025%. This solution will be gently poured into the vial containing the PCBAA hydrogel on the bottom and will be allowed to set for 10 min for adequate interpenetration of this solution to PCBAA hydrogel. After that, excess amount of the solution will be removed and the surface of PCBAA hydrogel exposed will be allowed to air-dry for various time points from 1 min to 1 hour. Then 0.02% (w/v) of trimesoyl chloride in hexane will be introduced to the exposed surface of PCBAA hydrogel to allow the interfacial polymerization for 30 second to 10 min, followed by rinsing with hexane, drying at 60° C. for 30 min, and equilibrium in water before further use.

Preparation of Zwitterionic PCBAA Reverse Coating on Poly(Iso-Phthaloyl Dichloride-Co-Triethylenetetramine) Membrane Substrate (Reverse Coating Composition 23) Using a Reverse Coating Method of the Present Invention.

Synthesis of PCBAA hydrogel: Briefly, 5 mg 2-Hydroxy-4'-(2-hydroxyethoxy)-2-Methylpropiophenone (I-2959) initiator and 30 mg N,N'-Methylenebis(acrylamide) (MBAA) crosslinker will be dissolved in 10 mL deionized water. 500 mg CBAA monomer will then be dissolved in 500 μL initiator/crosslinker solution to prepare a PCBAA pre-gel solution, which will be transferred to between two polypropylene liners adhered to glass slides separated with a Teflon spacer (e.g., 1 mm in thickness). UV will be applied for 20 minutes to crosslink and form the PCBAA hydrogel. PCBAA hydrogel obtained will be tailored and placed in the bottom of a 20-mL glass vial. Alternatively, various volumes of PCBAA pre-gel solution will be directly transferred to the bottom of a 20-ml glass vial followed by UV application 20 min to obtain the PCBAA hydrogel with various thicknesses, such as 1 mm.

Triethylenetetramine and trimethylamine will be dissolved in water to reach the same concentration such as 0.025%. This solution will be gently poured into the vial containing the PCBAA hydrogel on the bottom and will be allowed to set for 10 min for adequate interpenetration of this solution to PCBAA hydrogel. After that, excess amount of the solution will be removed and the surface of PCBAA hydrogel exposed will be allowed to air-dry for various time points from 1 min to 1 hour. Then 0.04% (w/v) of iso-phthaloyl dichloride in hexane will be introduced to the exposed surface of PCBAA hydrogel to allow the interfacial polymerization for 30 second to 10 min, followed by rinsing with hexane, drying at 60° C. for 30 min, and equilibrium in water before further use.

Preparation of Other Reverse Coatings on Polyamide Membrane Substrate Using a Reverse Coating Method of the Present Invention.

Referring to the preparation examples stated above, preparing the reverse coating can involve different types of hydrogel coating materials (e.g., PCBAA, PCBMA, PSBMA, PMPC, PEG, PNIPAAm, chitosan, etc.) using similar methods by forming different types of hydrogel coating materials first, then incubating with polyamines, including but not limited to m-phenylenediamine, p-phenylenediamine, piperazine, triethylenetetramine, N—N'-diaminopiperazine, N-(2-aminoethyl)-piperazine, poly(ethyleneimine), followed by interfacial polymerization with crosslinkers such as poly acyl chloride, including but not limited to trimesoyl chloride, iso-phthaloyl dichloride.

Preparation of Structure of Formula II.

Synthesis and Purification of the L-Carnitine Acrylate Monomer (L1 is COO; R1 is H)

Synthesis of the L-carnitine acrylate monomer was achieved using a one-step reaction. Briefly, 1.97 g L-carnitine hydrochloride (10 mmol) and 100 mg hydroquinone were added into 25 ml anhydrous dimethylformamide (DMF) in a flask purged with nitrogen. The mixture was heated to 40° C. and stirred for 10 mins. Then 2.43 ml acryloyl chloride (30 mmol) was dropped into the solution and the temperature was raised to 80° C. to react for 3 h. During the reaction, the flask was connected to a tube that leads to a liquid-seal bottle filled with triethylamine (TEA) to absorb excessive hydrogen chloride (HCl) from the reaction. The starting material L-carnitine hydrochloride gradually dissolved and the solution turned clear and brown.

It is critical to select the right solvent for the one-step reaction to obtain L-carnitine acrylate monomer. Acryloyl chloride has to be dissolved in a non-protic solvent to preserve its reactivity. L-carnitine on the other hand is hydrophilic and can hardly be dissolved in most non-protic solvents such as acetonitrile and dichloromethane. By increasing the temperature, L-carnitine hydrochloride can be partially dissolved in DMF and dimethyl sulfoxide (DMSO). Since DMSO drastically reacted with acryloyl chloride through Swern-oxidation, DMF was chosen as the solvent.

The reaction temperature was chosen at 80° C. since L-carnitine hydrochloride can be partially dissolved in solvent DMF at this temperature to facilitate the reaction. In addition, maintaining high temperature (40° C. or above) is critical since hydroquinone was oxidized to benzoquinone, which is a polymerization inhibitor, at lower temperatures and does not react with acryloyl chloride, leading to side products.

In a typical reaction between a hydroxy group and acryloyl chloride, TEA is often used in such reaction mixtures as the deacid reagent to increase reaction efficiency. However, TEA cannot be used in synthetic reaction systems of the present invention because: (1) it turned the L-carnitine from hydrochloride form to inner-salt form, which was totally insoluble in DMF even at 80° C.; and (2) at high temperature, the acryloyl chloride reacted with TEA significantly and produced side products that complicated the purification procedure.

After the single-step reaction described above, the rough product was purified as follows. The majority of hydrogen chloride generated and the excess amount of acryloyl chloride was removed under vacuum at room temperature by stirring the reaction solution. Then the resulting mixture was placed at −20° C. overnight. Unreacted L-carnitine hydrochloride was precipitated and removed by filtration. The resulting solution was further treated by anhydrous TEA where the L-carnitine acrylate monomer product, triethylamine hydrochloride and certain colored impurities were precipitated. The precipitate was washed with dichloromethane to remove triethylamine hydrochloride and was vacuum-dried. To remove the colored impurity, the obtained product was dissolved in anhydrous methanol stirred with activated charcoal for 2 h at 40° C. The supernatant was obtained by centrifugation, precipitated in diethyl ether and dried in vacuum. L-carnitine acrylate monomer in the form of light-yellow powder was obtained at the optimized yield of ~43%.

Synthesis of L-Carnitine Acrylate Hydrogel (L1 is COO; R1, R2, and R3 are H; L3 is CONHCH$_2$NHCO)

Briefly, 5 mg 2-Hydroxy-4'-(2-hydroxyethoxy)-2-Methylpropiophenone (I-2959) initiator and 30 mg N,N'-Methylenebis(acrylamide) (MBAA) crosslinker were dissolved in 10 mL deionized water. 500 mg L-carnitine acrylate monomer was then dissolved in 500 µL initiator/crosslinker solution to prepare a pre-gel solution, which was transferred to between two polypropylene liners adhered to glass slides separated with a Teflon spacer (e.g., 1 mm in thickness). UV was applied for 20 minutes to crosslink and form the L-carnitine acrylate hydrogel.

Structure formula II involves other types of carnitine derived monomers with various L1 and R1, and other types of crosslinker with various R2, R3, and L3. L1 is a linker that covalently couples the carnitine molecule to the monomeric repeating unit. Representative L1 groups include —C(=O)O—(CH$_2$)$_{n1}$— and —C(=O)NH—(CH$_2$)$_{n1}$—, where n1 is an integer from 1 to 20. R1, R2 and R3 are each independently selected from the group consisting of: hydrogen, fluorine, trifluoromethyl, $C_1$-$C_6$ alkyl, and $C_6$-$C_{12}$ aryl. L3 is a linker that covalently couples two polymer backbones.

In certain embodiments, structure formula II involves a crosslinker reacted with a zwitterionic carnitine derived monomers according to aspects of the present invention is one or more of: allyl methacrylate, diallyl itaconate, monoallyl itaconate, dially maleate, diallyl fumarate, diallyl succinate, diallyl phthalate, triallyl cyanurate, triallyl isocyanurate, diethylene glycol bis-allyl carbonate, divinyl ether of diethylene glycol, triallyl phosphate, triallyl trimellitate, allyl ether, diallylimidazolidone, pentaerythritol triallyl ether (PETE), N,N-diallylmelamine, triallyl-1,3,5-triazine-2,4,6-(1H,3H,5H)trione (TATT), 2,4,6-Triallyloxy-1,3,5-triazine; vinyl compounds, e.g. divinyl benzene, N,N'-methylene bis acrylamide (MBAA), methylenebis (methacrylamide), ethylene glycol dimethacrylate, ethylene glycol diacrylate, neopentylglycol dimethacrylate, tetraethylene glycol dimethacrylate, polyethylene glycol dimethacrylate, polyethylene glycol diacrylate, hexamethylene his maleimide, divinyl urea, bisphenol A bis methacrylate, divinyl adipate, glycerin trimethacrylate, trimethylolpropane triacrylate, trivinyl trimellitate, 1,5-pentadiene, 1,7-octadiene, 1,9-decadiene, 1,3-bis(4-methacryloxybutyl) tetramethyl disiloxane, divinyl ether, divinyl sulfone, N-vinyl-3 (E)-ethylidene pyrrolidone (EVP), ethylidene bis(N-vinyl pyrrolidone) (EBVP).

A crosslinker reacted with a zwitterionic carnitine derived monomer according to aspects of the present invention is MBAA.

Item List

Item 1. A coating composition, comprising a hydrophilic hydrogel element and a liner element, wherein a surface of the hydrophilic hydrogel element dissociably-engages a surface of the liner element.

Item 2. The coating composition of item 1, wherein the liner element comprises a polymer.

Item 3. The coating composition of item 2, wherein the liner element comprises a polypropylene surface, and the surface of the liner element that dissociably-engages the hydrophilic hydrogel element is the polypropylene surface of the liner element.

Item 4. The coating composition of any one of the preceding items, wherein: the liner element has a length, width, and thickness; the liner element is about 1 µm to about 10 cm thick; and the surface of the liner element that dissociably-engages the hydrophilic hydrogel element corresponds to a surface defined by the length and width of the liner element.

Item 5. The coating composition of any one of the preceding items, wherein: the hydrophilic hydrogel element has a length, width, and thickness; the hydrophilic hydrogel element is about 1 µm to about 5 cm thick; and the surface of the hydrophilic hydrogel element that dissociably-engages the liner element corresponds to a surface defined by the length and width of the hydrophilic hydrogel element.

Item 6. The coating composition of any one of the preceding items, wherein: the liner element has a top surface and a bottom surface; the hydrophilic hydrogel element has a top surface and a bottom surface; the coating composition is a roll or a panel; the top-surface of the hydrophilic hydrogel element dissociably-engages the bottom-surface of the liner element; and the bottom-surface of the hydrophilic hydrogel element dissociably-engages the top-surface of the liner element.

Item 7. The coating composition of any one of items 1 to 5, further comprising a second liner element, wherein: the hydrophilic hydrogel element has a top surface and a bottom surface; the top-surface of the hydrogel dissociably-engages the liner element; and the bottom-surface of the hydrogel dissociably-engages the second liner element.

Item 8. A binding composition, comprising a hydrophilic hydrogel element and a hydrophobic glue, wherein at least a portion of the gel network of the hydrophilic hydrogel element is occupied by the hydrophobic glue.

Item 9. The binding composition of item 8, wherein the hydrophobic glue comprises cyanoacrylate, ethyl cyanoacrylate, butyl cyanoacrylate, isobutyl cyanoacrylate, octyl cyanoacrylate, 2-octyl cyanoacrylate, other cyanoacrylate derivatives, metal adhesive, an epoxy-based adhesive or derivative thereof, a polyurethane-based adhesive or derivative thereof, or a styrene-butadiene adhesive or derivative thereof.

Item 10. The binding composition of item 8 or 9, wherein the hydrophobic glue is a curable or cured polymer.

Item 11. The binding composition of any one of items 8 to 10, wherein: the hydrophilic hydrogel element comprises a polymer network; the hydrophobic glue comprises a polymer network; and the polymer network of the hydrophilic hydrogel element and the polymer network of the hydrophobic glue are entangled.

Item 12. The binding composition of item 11, wherein the polymer network of the hydrophilic hydrogel element and the polymer network of the hydrophobic glue cannot be disentangled without breaking covalent bonds of either the polymer network of the hydrophilic hydrogel element or the polymer network of the hydrophobic glue.

Item 13. The binding composition of any one of items 8 to 12, further comprising a substrate, wherein the hydrophobic glue adheres to a surface of the substrate, thereby connecting the substrate and the hydrophilic hydrogel element.

Item 14. The binding composition of any one of items 8 to 13 wherein the hydrophobic glue comprises a cyanoacrylate glue.

Item 15. A composition comprising a hydrophilic hydrogel element and a substrate, wherein: the hydrophilic hydrogel element comprises a polymer network or a continuous phase; the substrate comprises a surface comprising a polymer network or a continuous phase; the polymer network or the continuous phase of the hydrophilic hydrogel element and the polymer network or the continuous phase of the surface are entangled; and the porosity of the hydrophilic hydrogel element is greater than the porosity of the substrate.

Item 16. The composition of item 15, wherein the entanglement is physical in nature and the polymer network or the continuous phase of the hydrophilic hydrogel element and the polymer network or the continuous phase of the surface of the substrate cannot be disentangled without breaking covalent, ionic, or hydrogen bonds of either the polymer network or the continuous phase of the hydrogel or the covalent, ionic, or hydrogen bonds of polymer network or the covalent, ionic, hydrogen, metallic or van der Waals bonds of continuous phase of the surface of the substrate.

Item 17. The composition of any one of items 15 or 16, wherein the surface of the substrate comprises a material selected from the group consisting of: agarose, crosslinked alginate, crosslinked or non-crosslinked poly-hydroxyethyl-methacrylate (PHEMA), crosslinked or non-crosslinked poly-N-(2-Hydroxypropyl) methacrylamide (PHPMA), polydimethylsiloxane (PDMS), crosslinked or non-crosslinked polystyrene (PS), crosslinked silicone hydrogel, polyurethane (PU), silicone rubber, epoxy, epoxy-coated steel, glass, ceramic, plastic, metal, membrane materials, a derivative of any of the foregoing, and a combination of any two or more of the foregoing.

Item 18. The composition of any one of the preceding items, wherein the hydrophilic hydrogel element comprises a zwitterionic hydrogel.

Item 19. The composition of any one of the preceding items, wherein the hydrophilic hydrogel element comprises a polymer comprising repeating subunits, and the repeating subunits of the polymer are zwitterionic.

Item 20. The composition of any one of the preceding items, wherein the hydrophilic hydrogel element comprises a crosslinked or non-crosslinked polymer.

Item 21. The composition of any one of the preceding items, wherein the hydrophilic hydrogel element comprises a natural or synthetic polymer or network.

Item 22. The composition of any one of the preceding items, wherein the hydrophilic hydrogel element comprises one or more of crosslinked poly-acrylic acid, crosslinked poly(vinyl alcohol), non-crosslinked poly(vinyl alcohol), crosslinked poly(vinylpyrrolidone), non-crosslinked poly(vinylpyrrolidone), silicone-containing hydrogel, crosslinked polyacrylamide, crosslinked poly-(N-isopropyl-acrylamide), non-crosslinked poly-(N-isopropyl-acrylamide), crosslinked poly-methyl-methacrylate, poly-hydroxyethyl-methacrylate (PHEMA), crosslinked polyethylene glycol (PEG), crosslinked poly(ethylene glycol) methacrylate (PEGMA), crosslinked poly(ethylene glycol) diacrylate (PEGDA), polypropylene glycol, crosslinked zwitterionic poly-(sulfobetaine methacrylate) (PSBMA), crosslinked zwitterionic 2-methacryloyloxyethyl phosphorylcholine (PMPC), crosslinked zwitterionic poly-carboxybetaine methacrylate (PCBMA), crosslinked zwitterionic poly-carboxybetaine acrylamide (PCBAA), non-crosslinked zwitterionic PCBAA, crosslinked alginate, crosslinked chitosan, gelatin, collagen, fibrin, agarose, hyaluronic acid, cellulose, polypeptides, or a derivative of one or more of the foregoing.

Item 23. The composition of any one of the preceding items, wherein: the hydrophilic hydrogel element comprises a polymer having a structure of formula I,

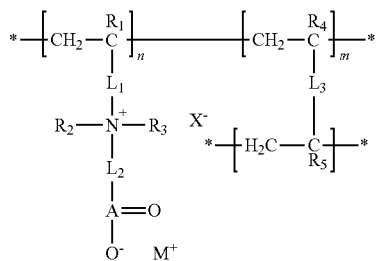

I $R_1$, $R_2$, $R_3$, $R_4$, and $R_5$ are each independently selected from hydrogen, alkyl, and aryl groups; $L_1$ is a linker that covalently couples a cationic center to the polymer backbone; $L_2$ is a linker that covalently couples the cationic center to an anionic group; $A(=O)O^-$ is the anionic group; A is C, S, SO, P, or PO; $X^-$ is a counter ion associated with the cationic center; $M^+$ is a metal ion, an ammonium ion, or an organic ion; $L_3$ is a linker that covalently couples two polymer backbones; n is an integer in the range of 2 to about 100,000; m is a positive non-zero integer; and m/n is in the range of 0.1%-99.9%.

Item 24. The composition of item 23, wherein:
$R_1$, $R_4$, and $R_5$ are each independently selected from the group consisting of hydrogen, fluorine, trifluoromethyl, $C_1$-$C_5$ alkyl, and $C_6$-$C_{12}$ aryl groups; $R_2$ and R3 are independently selected from the group consisting of alkyl and aryl, or taken together with the nitrogen to which they are attached form a cationic center; $L_1$, is a linker that covalently couples the cationic center $[N^+(R_2)(R_3)]$ to a polymer backbone $[-(CH_2-CR_1)_n-]$; and $L_2$ is a linker that covalently couples an anionic center $[A(=O)-O^-]$ to the cationic center.

Item 25. The composition of any one of the preceding items, wherein: the hydrophilic hydrogel element comprises a polymer having a structure of formula II,

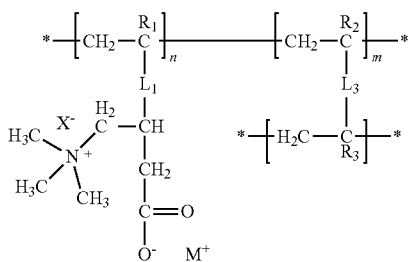

II $R_1$, $R_2$, and $R_3$ are each independently selected from hydrogen, alkyl, and aryl groups; $L_1$ is a linker that covalently couples the polymer sidechain to the polymer backbone; $X^-$ is a counter ion associated with the cationic center; $M^+$ is a metal ion, an ammonium ion, or an organic ion; $L_3$ is a linker that covalently couples two polymer backbones; n is an integer in the range of 2 to about 100,000; m is a positive non-zero integer; and m/n is in the range of 0.1%-99.9%.

Item 26. The composition of item 25, wherein:
$R_1$, $R_2$, and $R_3$ are each independently selected from the group consisting of hydrogen, fluorine, trifluoromethyl, $C_1$-$C_6$ alkyl, and $C_6$-$C_{12}$ aryl groups; $L_1$ is $-C(=O)O-(CH_2)_z-$ or $-C(=O)NH-(CH_2)_z-$; and z is an integer from 1 to 20.

Item 27. The composition of any one of the preceding items, wherein: the hydrophilic hydrogel element comprises a polymer having a structure of formula III,

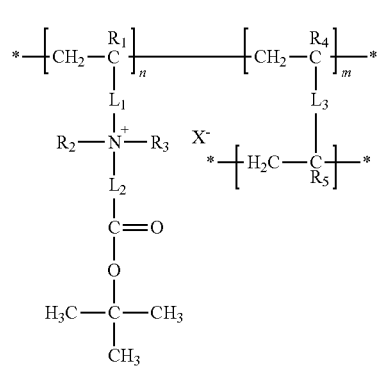

III $R_1$, $R_2$, $R_3$, $R_4$, and $R_5$ are each independently selected from hydrogen, alkyl, and aryl groups; $L_1$ is a linker that covalently couples a cationic center to the polymer backbone; $L_2$ is a linker that covalently couples the cationic center to an anionic group; $X^-$ is a counter ion associated with the cationic center; $L_3$ is a linker that covalently couples two polymer backbones; n is an integer in the range of 2 to about 100,000; m is a positive non-zero integer; and m/n is in the range of 0.1%-99.9%.

Item 28. The composition of item 27, wherein:
$R_1$, $R_4$, and $R_5$ are each independently selected from the group consisting of hydrogen, fluorine, trifluoromethyl, $C_1$-$C_6$ alkyl, and $C_6$-$C_{12}$ aryl groups; $R_2$ and $R_3$ are independently selected from the group consisting of alkyl and aryl, or taken together with the nitrogen to which they are attached form a cationic center; $L_1$ is a linker that covalently couples the cationic center $[N^+(R_2)(R_3)]$ to a polymer backbone $[-(CH_2-CR_1)_n-]$; and $L_2$ is a linker that covalently couples an anionic center $[C(=O)-O^-]$ to the cationic center.

Item 29. The composition of any one of the preceding items, wherein the hydrophilic hydrogel element comprises two substantially parallel surfaces, and the distance between the two substantially parallel surfaces is about 1 nm to about 5 cm.

Item 30. A device, comprising the composition of any one of items 8 to 29, wherein a surface of the device is at least partially covered by the hydrophilic hydrogel element.

Item 31. The device of item 30, wherein the device is a medical device.

Item 32. The medical device of item 31, wherein the medical device is an implantable medical device or a surgical instrument.

Item 33. The medical device of item 32, wherein the medical device is a blood or tissue contacting device.

Item 34. The medical device of item 32, wherein the medical device is a stent, artificial blood vessel, catheter, tubing, or dialysis device.

Item 35. A water-immersible device, comprising the composition of any one of items 8 to 29, wherein a surface of the water-immersible device is at least partially covered by the hydrophilic hydrogel element.

Item 36. The water-immersible device of item 35, wherein the water-immersible device is a component of a watercraft, dock, lock, dam, water-treatment plant, underwater cable, offshore drill, or offshore well, or an instrument or tool for operating or maintaining any one of the foregoing.

Item 37. The water-immersible device of item 36, wherein the water-immersible device is the hull of a watercraft.

Item 38. A method for applying a hydrophilic polymer hydrogel to a surface, comprising: contacting the surface with a hydrophobic glue, to produce a glue-coated surface; and contacting the glue-coated surface with a hydrophilic hydrogel element.

Item 39. The method of item 38, wherein the hydrophobic glue comprises cyanoacrylate, ethyl cyanoacrylate, butyl cyanoacrylate, isobutyl cyanoacrylate, octyl cyanoacrylate, 2-octyl cyanoacrylate, another cyanoacrylate derivative, metal adhesive, an epoxy-based adhesive or derivative thereof, a polyurethane-based adhesive or derivative thereof, or a styrene-butadiene adhesive or derivative thereof.

Item 40. The method of item 38 or 39, wherein the surface comprises agarose, alginate, poly-hydroxyethyl-methacrylate (PHEMA), polydimethylsiloxane (PDMS), polyurethane (PU), polystyrene (PS), PVC panel, silicone rubber, silicone hydrogel, epoxy, epoxy-coated steel, glass, ceramic, plastic, metal, wood, or a derivative of any of the foregoing or a combination of any two or more of the foregoing.

Item 41. The method of any one of items 38 to 40, wherein the hydrophobic glue comprises a curable polymer and the method further comprises curing the curable polymer.

Item 42. The method of item 41, wherein curing the curable polymer comprises heating, drying, evaporating a solvent, and/or irradiation with microwave, infrared, visible, and/or ultraviolet radiation.

Item 43. A reverse coating method for making a hydrogel-coated material, comprising: fixing a hydrogel in a desired shape, producing a shaped hydrogel component; contacting the shaped hydrogel component with a flowable and curable or solidifiable substrate, wherein contacting the shaped hydrogel component with the flowable substrate results in at least a portion of the flowable substrate entering the hydrogel of the shaped hydrogel component; and curing or solidifying the substrate.

Item 44. The method of item 43, wherein the flowable substrate is a liquid, suspension, colloid, or powder.

Item 45. The method of item 43 or 44, wherein curing or solidifying the substrate comprises heating or cooling the substrate, drying the substrate, evaporating solvent, or irradiating the substrate with microwave, infrared, visible, or ultraviolet radiation.

Item 46. The method of any one of items 43 to 45, wherein the flowable substrate comprises plastic, silicone, metal, ceramics, or small or macro molecules capable of polymerization.

Item 47. The method of item 43, wherein fixing the hydrogel in a desired shape comprises forming the hydrogel on a surface or in a mold.

Item 48. The method of any one of items 43 to 47, wherein the hydrogel is a zwitterionic hydrogel.

Item 49. The method of item 48, wherein the hydrogel comprises a polymer comprising repeating subunits, and the repeating subunits are zwitterionic.

Item 50. The method of any one of items 43 to 49, wherein the hydrogel comprises a crosslinked or non-crosslinked polymer.

Item 51. The method of any one of items 43 to 50, wherein the hydrogel comprises a natural or synthetic polymer or network.

Item 52. The method of any one of items 43 to 51, wherein the hydrogel comprises one or more of crosslinked polyacrylic acid, crosslinked poly(vinyl alcohol), non-crosslinked poly(vinyl alcohol), crosslinked poly(vinylpyrrolidone), non-crosslinked poly(vinylpyrrolidone), crosslinked polyacrylamide, crosslinked poly-(N-isopropyl-acrylamide) (PNIPAAm), non-crosslinked poly-(N-isopropyl-acrylamide), crosslinked poly-methyl-methacrylate, crosslinked polyethylene glycol (PEG), crosslinked poly(ethylene glycol) methacrylate (PEGMA), crosslinked poly(ethylene glycol) diacrylate (PEGDA), crosslinked polypropylene glycol, crosslinked zwitterionic poly-(sulfobetaine methacrylate) (PSBMA), crosslinked zwitterionic 2-methacryloyloxyethyl phosphorylcholine (PMPC), crosslinked zwitterionic poly-carboxybetaine methacrylate (PCBMA), crosslinked zwitterionic poly-carboxybetaine acrylamide (PCBAA), non-crosslinked zwitterionic PCBAA, crosslinked alginate, crosslinked chitosan, gelatin, collagen, fibrin, agarose, hyaluronic acid, cellulose, polypeptides, or a derivative of one or more of the foregoing.

Item 53. The method of any one of items 43 to 52, wherein the hydrogel comprises two, substantially parallel surfaces, and the distance between the two, substantially parallel surfaces is about 1 μm to about 5 cm.

Item 54. A device comprising a surface at least partially coated with a hydrogel produced according to the method of any one of items 43 to 53.

Item 55. The device of item 54, wherein the device is selected from: a medical device, a research device, and a marine device.

Item 56. The device of item 55 wherein the medical device is an implantable medical device, a surgical instrument, a blood or tissue contacting device, a stent, an artificial blood vessel, a catheter, tubing, or a dialysis device.

Item 57. The device of item 55 wherein the research device is tubing, glassware, or a molded plastic container.

Item 58. The device of item 55 wherein the marine device is a component of a watercraft, dock, lock, dam, water-treatment plant, underwater cable, offshore drill, or offshore well, or an instrument or tool for operating or maintaining any one of the foregoing.

Item 59. The device of item 58, wherein the marine device is the hull of a watercraft.

Item 60. A polymer having structural formula II:

$$*-[CH_2-\underset{\underset{L_1}{|}}{\overset{\overset{R_1}{|}}{C}}]_n- \quad -[CH_2-\underset{\underset{L_3}{|}}{\overset{\overset{R_2}{|}}{C}}]_m-* \quad \text{II}$$

with sidechain: $H_3C-\underset{H_3C}{\overset{}{N^+}}\diagdown_{CH_3}\overset{X^-}{\phantom{N}}\underset{H_2}{C}-CH-CH_2-C(=O)-O^-\ M^+$ and $*-[H_2C-\underset{R_3}{\overset{}{C}}]-*$ where $R_1$, $R_2$, and $R_3$ are each independently selected from hydrogen, alkyl, and aryl groups; $L_1$ is a linker that covalently couples the polymer sidechain to the polymer backbone; $X^-$ is a counter ion associated with the cationic center: $M^+$ is a metal ion, an ammonium ion, or an organic ion; $L_3$ is a linker that covalently couples two polymer backbones; n is an integer in the range of 2 to about 100,000; m is a positive non-zero integer; and m/n is in the range of 0.1%-99.9%.

Item 61. The polymer of item 60, where $R_1$, $R_2$, and $R_3$ are each independently selected from the group consisting of hydrogen, fluorine, trifluoromethyl, $C_1$-$C_6$ alkyl, and $C_6$-$C_{12}$ aryl groups; $L_1$ is —C(=O)O—(CH$_2$)$_z$— or —C(=O)NH—(CH$_2$)$_z$—; and z is an integer from 1 to 20.

Item 62. The composition of any of the preceding items, wherein: the hydrophilic hydrogel element comprises a polymer having a structure of formula I, which is a polymerization product of: 1) one or more zwitterionic carboxybetaine monomers, sulfobetaine monomers, and phosphobetaine monomers and 2) crosslinkers, together, or a polymerization product of one or more zwitterionic carboxybetaine monomers, sulfobetaine monomers, and phosphobetaine monomers polymerized first and later crosslinked.

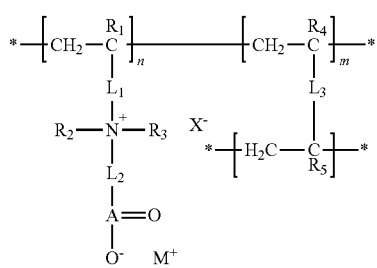

I $R_1$, $R_2$, $R_3$, $R_4$, and $R_5$ are each independently selected from hydrogen, alkyl, and aryl groups; $L_1$ is a linker that covalently couples a cationic center to the polymer backbone; $L_2$ is a linker that covalently couples the cationic center to an anionic group; A(=O)O$^-$ is the anionic group; A is C, S, SO, P, or PO; X$^-$ is a counter ion associated with the cationic center; M$^+$ is a metal ion, an ammonium ion, or an organic ion; $L_3$ is a linker that covalently couples two polymer backbones; n is an integer in the range of 2 to about 100,000; m is a positive non-zero integer; and m/n is in the range of 0.1%-99.9%.

Item 63. The composition of item 62, wherein:
$R_1$, $R_4$, and $R_5$ are each independently selected from the group consisting of hydrogen, fluorine, trifluoromethyl, $C_1$-$C_6$ alkyl, and $C_6$-$C_{12}$ aryl groups; $R_2$ and $R_3$ are independently selected from the group consisting of alkyl and aryl, or taken together with the nitrogen to which they are attached form a cationic center; $L_1$ is a linker that covalently couples the cationic center [N$^+$(R$_2$)(R$_3$)] to a polymer backbone [—(CH$_2$—CR$_1$)$_n$—]; and $L_2$ is a linker that covalently couples an anionic center [A(=O)—O$^-$] to the cationic center.

Item 64. The composition of any one of the preceding items, wherein: the hydrophilic hydrogel element comprises a polymer having a structure of formula II, which is a polymerization product of: 1) zwitterionic carnitine derived monomers and 2) crosslinkers, together, or a polymerization product of zwitterionic carnitine derived monomers polymerized first and later crosslinked.

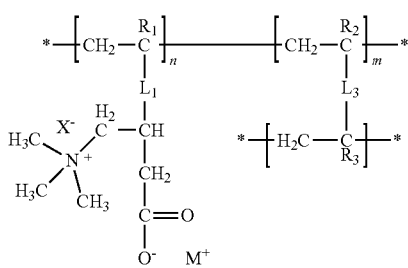

II $R_1$, $R_2$, and $R_3$ are each independently selected from hydrogen, alkyl, and aryl groups; $L_1$ is a linker that covalently couples the polymer sidechain to the polymer backbone; X$^-$ is a counter ion associated with the cationic center; M$^+$ is a metal ion, an ammonium ion, or an organic ion; $L_3$ is a linker that covalently couples two polymer backbones; n is an integer in the range of 2 to about 100,000; m is a positive non-zero integer; and m/n is in the range of 0.1%-99.9%.

Item 65. The composition of item 64, wherein:
$R_1$, $R_2$, and $R_3$ are each independently selected from the group consisting of hydrogen, fluorine, trifluoromethyl, $C_1$-$C_6$ alkyl, and $C_6$-$C_{12}$ aryl groups; $L_1$ is —C(=O)O—(CH$_2$)$_z$— or —C(=O)NH—(CH$_2$)$_z$—; and z is an integer from 1 to 20.

Item 66. The composition of any one of the preceding items, wherein: the hydrophilic hydrogel element comprises a polymer having a structure of formula III, which is a polymerization product of zwitterionic carboxybetaine ester monomers with crosslinkers which is a polymerization product of: 1) zwitterionic carboxybetaine ester monomers and 2) crosslinkers, together, or a polymerization product of zwitterionic carboxybetaine ester monomers polymerized first and later crosslinked.

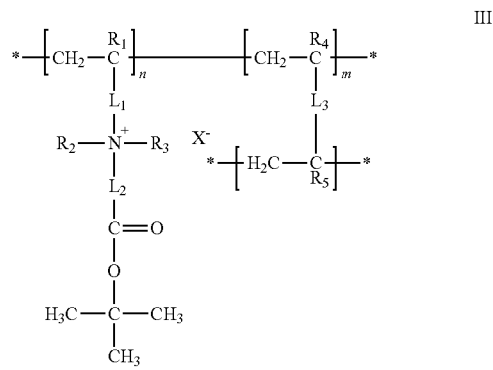

III $R_1$, $R_2$, $R_3$, $R_4$, and $R_5$ are each independently selected from hydrogen, alkyl, and aryl groups; $L_1$ is a linker that covalently couples a cationic center to the polymer backbone; $L_2$ is a linker that covalently couples the cationic center to an anionic group; X$^-$ is a counter ion associated with the cationic center; $L_3$ is a linker that covalently couples two polymer backbones; n is an integer in the range of 2 to about 100,000; m is a positive non-zero integer; and m/n is in the range of 0.1%-99.9%.

Item 66. The composition of item 67, wherein:
$R_1$, $R_4$, and $R_5$ are each independently selected from the group consisting of hydrogen, fluorine, trifluoromethyl, $C_1$-$C_6$ alkyl, and $C_6$-$C_{12}$ aryl groups; $R_2$ and $R_3$ are independently selected from the group consisting of alkyl and aryl, or taken together with the nitrogen to which they are attached form a cationic center; $L_1$ is a linker that covalently couples the cationic center [N$^+$(R$_2$)(R$_3$)] to a polymer backbone [—(CH$_2$—CR$_1$))$_n$—]; and $L_2$ is a linker that covalently couples an anionic center [C(=O)—O$^-$] to the cationic center.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A composition comprising a hydrophilic hydrogel element and a substrate, wherein:
the hydrophilic hydrogel element comprises a polymer network or a continuous phase, wherein:
the hydrophilic hydrogel element comprises a polymer having a structure of formula II

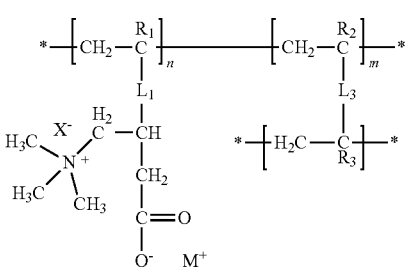

$R_1$, $R_2$, and $R_3$ are each independently selected from hydrogen, alkyl, and aryl groups;
$L_1$ is a linker that covalently couples the polymer side-chain to the polymer backbone;
$X^-$ is a counter ion associated with the cationic center;
$M^+$ is a metal ion, an ammonium ion, or an organic ion;
$L_3$ is a linker that covalently couples two polymer backbones;
n is an integer in the range of 2 to about 100,000;
m is a positive non-zero integer; and
m/n is in the range of 0.1%-99.9%;
the substrate comprises a surface comprising a polymer network or a continuous phase; and
the polymer network or the continuous phase of the hydrophilic hydrogel element and the polymer network or the continuous phase of the surface are entangled, wherein the entanglement is physical in nature and the polymer network or the continuous phase of the hydrophilic hydrogel element and the polymer network or the continuous phase of the surface of the substrate cannot be disentangled without breaking covalent, ionic, or hydrogen bonds of either the polymer network or the continuous phase of the hydrogel or the covalent, ionic, or hydrogen bonds of polymer network or the covalent, ionic, hydrogen, metallic or van der Waals bonds of continuous phase of the surface of the substrate; and
the porosity of the hydrophilic hydrogel element is greater than the porosity of the substrate.

2. The composition of claim 1, wherein the surface of the substrate comprises a material selected from the group consisting of: agarose, crosslinked alginate, crosslinked or non-crosslinked poly-hydroxyethyl-methacrylate (PHEMA), crosslinked or non-crosslinked poly-N-(2-Hydroxypropyl) methacrylamide (PHPMA), polydimethylsiloxane (PDMS), crosslinked or non-crossliked polystyrene (PS), crosslinked silicone hydrogel, polyurethane (PU), silicone rubber, epoxy, epoxy-coated steel, glass, ceramic, plastic, metal, membrane materials, a derivative of any of the foregoing, and a combination of any two or more of the foregoing.

3. The composition of claim 1, wherein the hydrophilic hydrogel element comprises a crosslinked or non-crosslinked polymer.

4. The composition of claim 1, wherein the hydrophilic hydrogel element further comprises one or more of crosslinked poly-acrylic acid, crosslinked poly(vinyl alcohol), non-crosslinked poly(vinyl alcohol), crosslinked poly(vinylpyrrolidone), non-crosslinked poly(vinylpyrrolidone), silicone-containing hydrogel, crosslinked polyacrylamide, crosslinked poly-(N-isopropyl-acrylamide), non-crosslinked poly-(N-isopropyl-acrylamide), crosslinked poly-methylmethacrylate, poly-hydroxyethyl-methacrylate (PHEMA), crosslinked polyethylene glycol (PEG), crosslinked poly (ethylene glycol) methacrylate (PEGMA), crosslinked poly (ethylene glycol) diacrylate (PEGDA), polypropylene glycol, crosslinked zwitterionic poly-(sulfobetaine methacrylate) (PSBMA), crosslinked zwitterionic 2-methacryloyloxyethyl phosphorylcholine (PMPC), crosslinked zwitterionic poly-carboxybetaine methacrylate (PCBMA), crosslinked zwitterionic poly-carboxybetaine acrylamide (PCBAA), non-crosslinked zwitterionic PCBAA, crosslinked alginate, crosslinked chitosan, gelatin, collagen, fibrin, agarose, hyaluronic acid, cellulose, polypeptides, or a derivative of one or more of the foregoing.

5. The composition of claim 1, wherein:
$R_1$, $R_2$, and $R_3$ are each independently selected from the group consisting of hydrogen, fluorine, trifluoromethyl, $C_1$-$C_6$ alkyl, and $C_6$-$C_{12}$ aryl groups;
$L_1$ is —C(=O)O—$(CH_2)_z$- or —C(=O)NH—$(CH_2)_z$-; and
z is an integer from 1 to 20.

6. A device, comprising the hydrophilic hydrogel element of claim 1, wherein a surface of the device is at least partially covered by the hydrophilic hydrogel element.

7. The device of claim 6, wherein the device is a medical device.

8. The medical device of claim 7, wherein the medical device is an implantable medical device or a surgical instrument.

9. The medical device of claim 8, wherein the medical device is a blood or tissue contacting device.

10. The medical device of claim 8, wherein the medical device is a stent, artificial blood vessel, catheter, tubing, or dialysis device.

11. A water-immersible device, comprising the hydrophilic hydrogel element of claim 1, wherein a surface of the water-immersible device is at least partially covered by the hydrophilic hydrogel element.

12. The water-immersible device of claim 11, wherein the water-immersible device is a component of a watercraft, dock, lock, dam, water-treatment plant, underwater cable, offshore drill, or offshore well, or an instrument or tool for operating or maintaining any one of the foregoing.

13. The water-immersible device of claim 12, wherein the water-immersible device is the hull of a watercraft.

* * * * *